(12) United States Patent
Cance et al.

(10) Patent No.: US 8,404,669 B2
(45) Date of Patent: Mar. 26, 2013

(54) KINASE MODULATING COMPOUNDS AND USES THEREOF FOR TREATMENT OF CANCER

(75) Inventors: William G. Cance, Gainesville, FL (US); Elena Kurenova, Gainesville, FL (US); Vita Golubovskaya, Gainesville, FL (US); David A. Ostrov, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 767 days.

(21) Appl. No.: 12/283,826

(22) Filed: Sep. 15, 2008

(65) Prior Publication Data

US 2009/0239850 A1 Sep. 24, 2009

Related U.S. Application Data

(63) Continuation-in-part of application No. PCT/US2008/003451, filed on Mar. 14, 2008.

(60) Provisional application No. 61/069,248, filed on Mar. 12, 2008, provisional application No. 60/918,615, filed on Mar. 16, 2007.

(51) Int. Cl.
*A01K 43/40* (2006.01)
*A61K 31/44* (2006.01)

(52) U.S. Cl. ........................... 514/183; 514/352

(58) Field of Classification Search .................. None
See application file for complete search history.

(56) References Cited

U.S. PATENT DOCUMENTS

| | | | |
|---|---|---|---|
| 2003/0114473 A1 | 6/2003 | Pease et al. | |
| 2005/0009853 A1* | 1/2005 | Kath et al. | 514/275 |
| 2005/0037963 A1 | 2/2005 | Guan et al. | |
| 2009/0053148 A1* | 2/2009 | Kandimalla et al. | 424/45 |

FOREIGN PATENT DOCUMENTS

| | | | |
|---|---|---|---|
| WO | 2005/007672 A2 | 1/2005 | |
| WO | WO 2005/007672 | * | 1/2005 |
| WO | WO-2005/049852 A3 | 11/2005 | |

OTHER PUBLICATIONS

Roman et al. Imexon and gemcitabine are synergistic against human pancreatic cancer cells in vitro and in vivo. Experimental and Molecular Therapeutics, 50: Novel Agents 2. Abstract #5884.*
Garces et al., "Vascular endothelial growth factor receptor-3 and focal adhesion kinase bind and suppress apoptosis in breast cancer cells", Cancer Research, Feb. 1, 2006, 66: 1446-1454; abstract, p. 1447, para 4.
Golubovskaya et al.,"Direct interaction of the N-terminal domain of focal adhesion kinase with the N-terminal transactivation domain of p53", J Biol Chem, Jul. 1, 2005, 280:25008-25021; abstract.
Hayashi et al., "The focal adhesion targeting (FAT) region of focal adhesion kinase is a four-helix bundle that binds paxillin" Nature Structural Biology, Feb. 2002,9:101-106; abstract.
International Preliminary Report on Patentability issued Sep. 22, 2009 for PCT/US2008/003451.
International Search Report and Written Opinion issued Aug. 19, 2008 for PCT/US2008/003451.
Z Gesamte Inn Med.; The effect of intratumorally administered isotonic suprastin solution on inoculation tumors of mice; Nov. 15, 1963; 18(): 1033-5.
Beierle E A. et al. "Inhibition of VEGFR-3 binding to FAK induces apoptosis in human neuroblastoma cells", Journal of Surgical Research, vol. 130, No. 2, Feb. 1, 2006, pp. 179-180 XP024952895.
Kurenova Elena et al. "Focal adhesion kinase suppresses apoptosis by binding to the death domain of receptor-interacting protein.", Molecular and Cellular Biology, May 2004, vol. 24, No. 10, pp. 4361-4371. LNKD-PUBMED: 15121855.
Garces, Christopher et al. "Vascular Endothelial Growth Factor Receptor-3 and Focal Adhesion Kinase Bind and Suppress Apoptosis in Breast Cancer Cells.", Cancer Research, 66 (3), Feb. 1, 2006, pp. 14446-1454.
Extended Search Report for European Patent Application No. 08726863.7.

* cited by examiner

*Primary Examiner* — Brandon Fetterolf
*Assistant Examiner* — Anna Pagonakis
(74) *Attorney, Agent, or Firm* — Edwards Wildman Palmer LLP; Jeffrey D. Hsi

(57) ABSTRACT

The invention relates to protein binding inhibitor compounds and methods of identifying and using them. The invention further relates to pharmaceutical compositions and methods for treating a variety of diseases and disorders, including cell proliferative disorders, especially cancer.

11 Claims, 29 Drawing Sheets

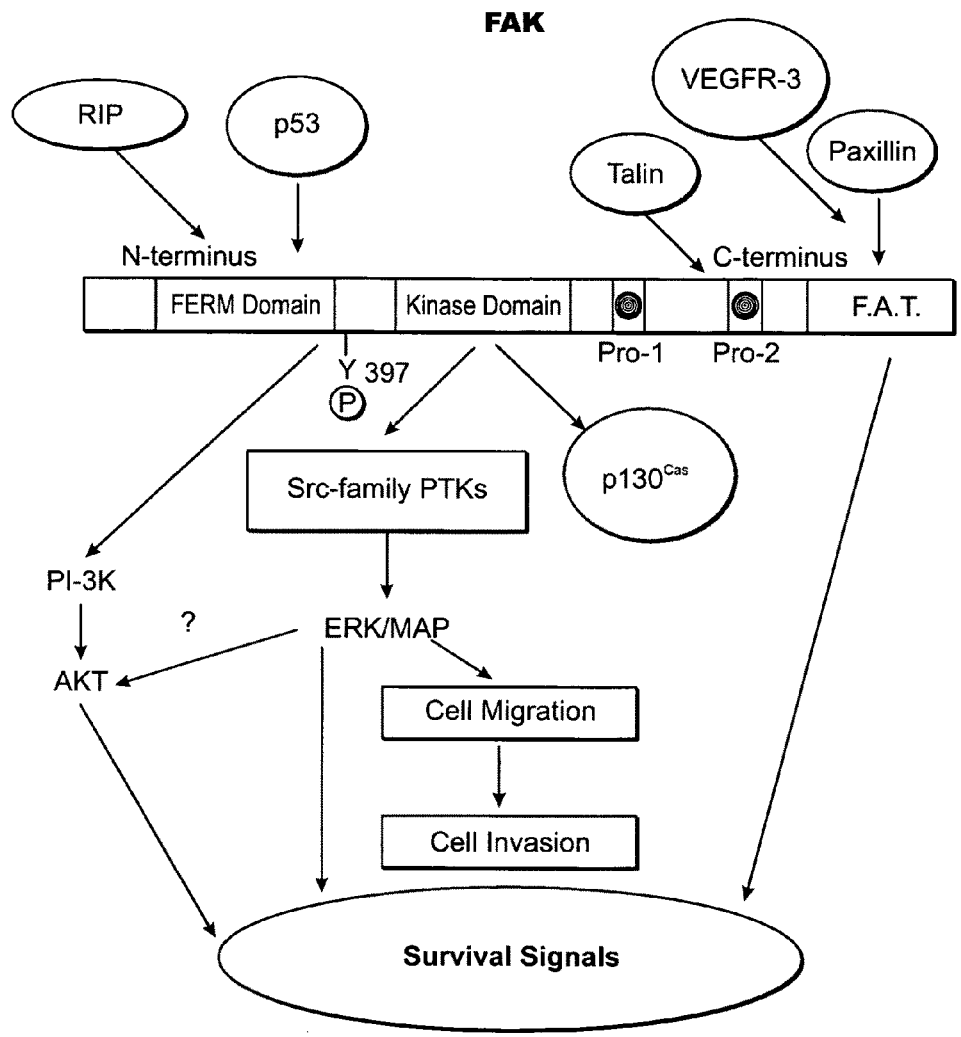
FIG. 1.1

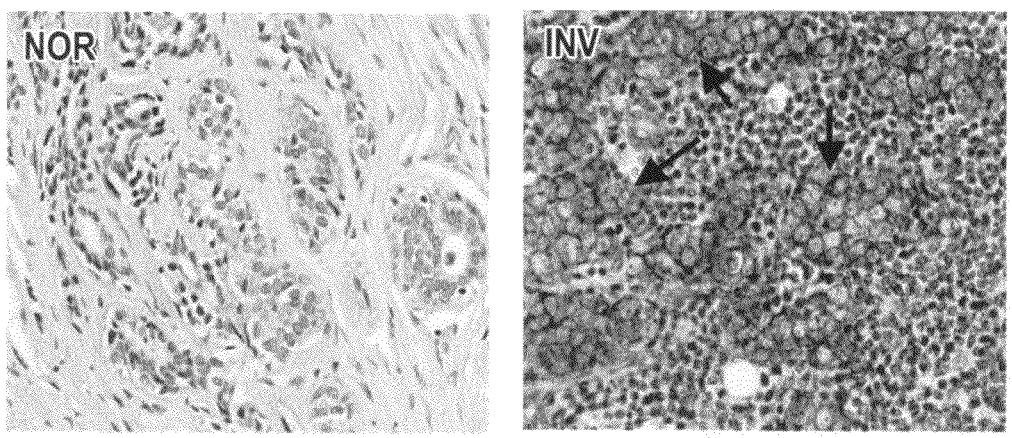
FIG. 1.2

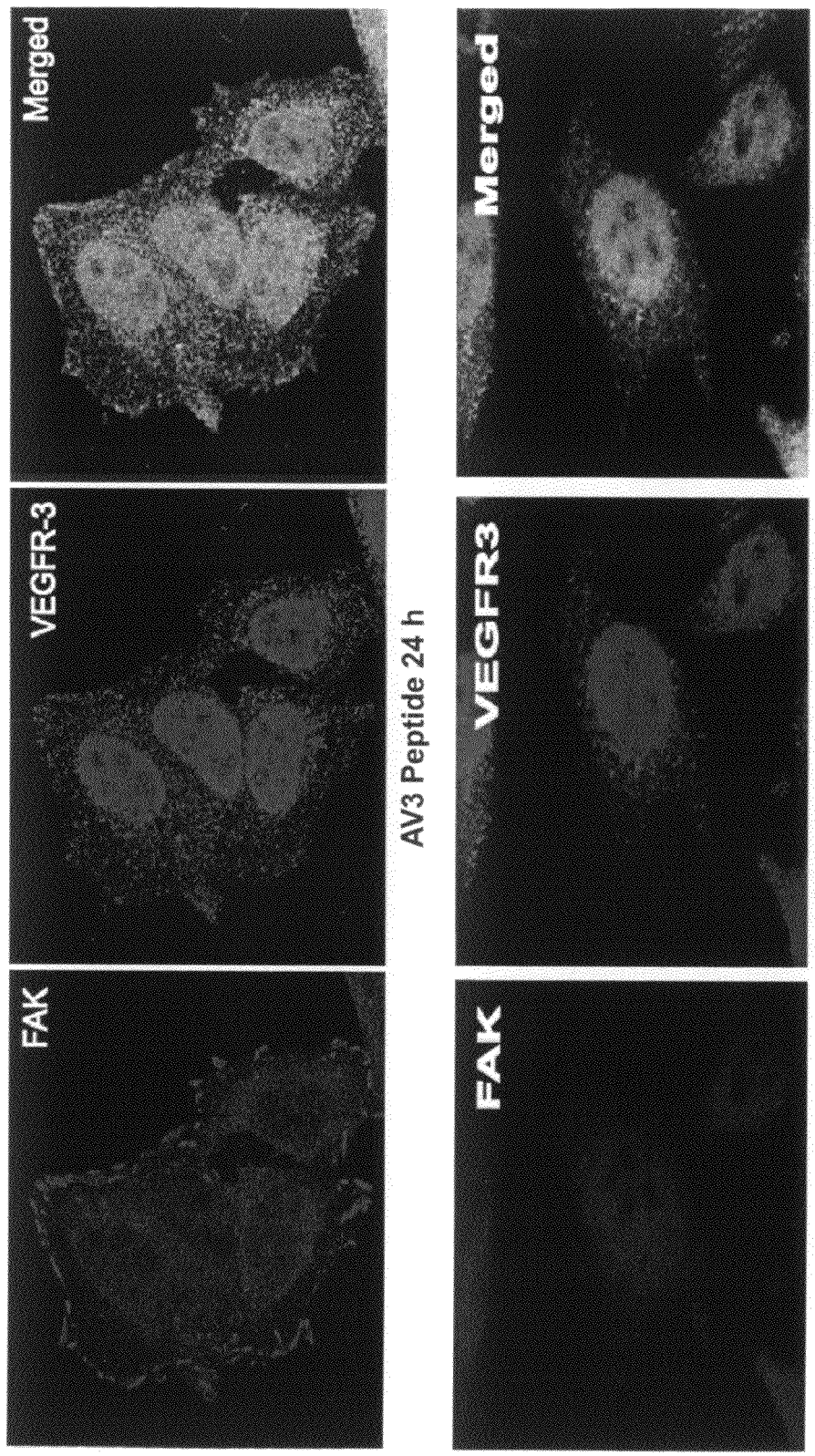
FIG. 1.3A

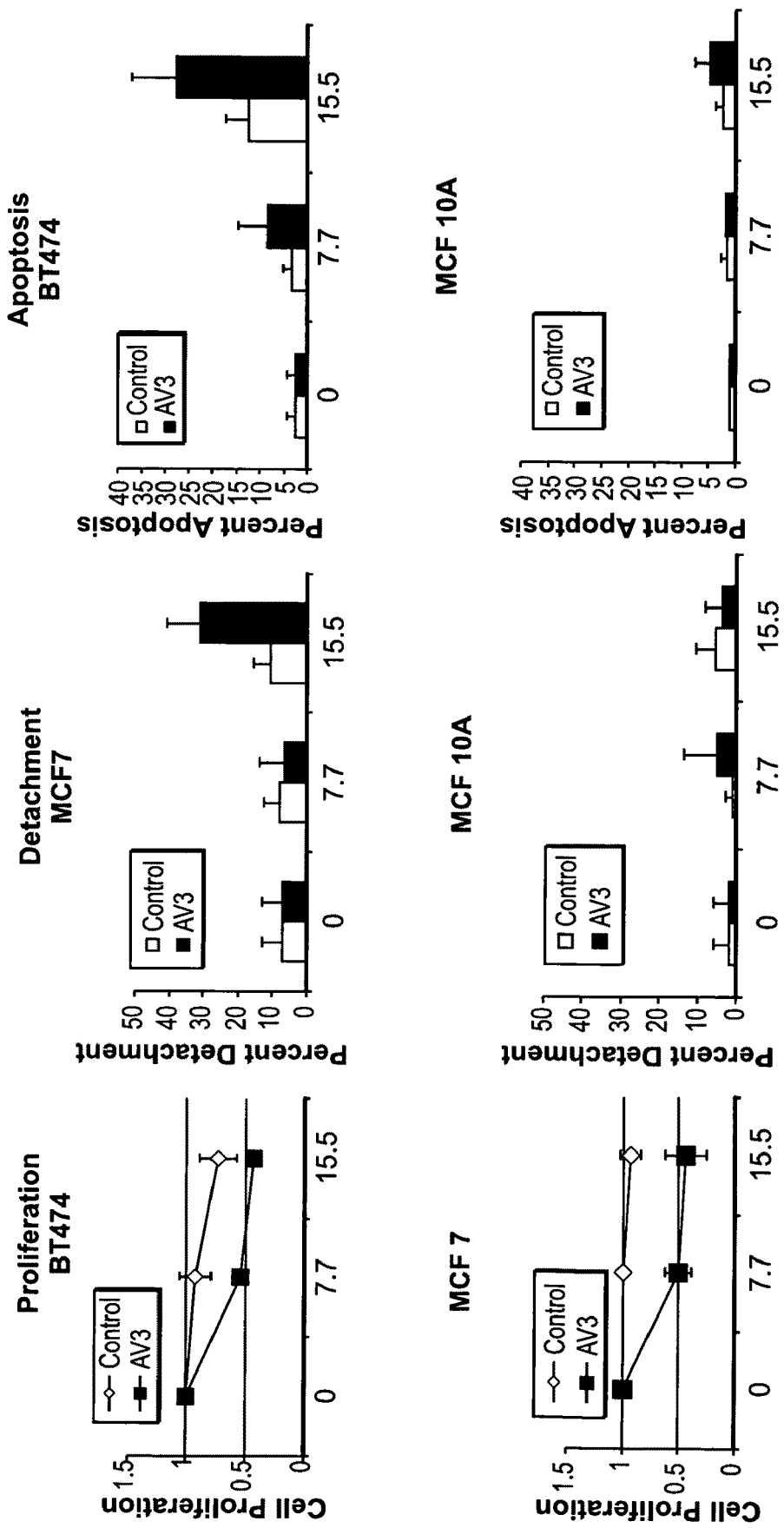
FIG. 1.3B

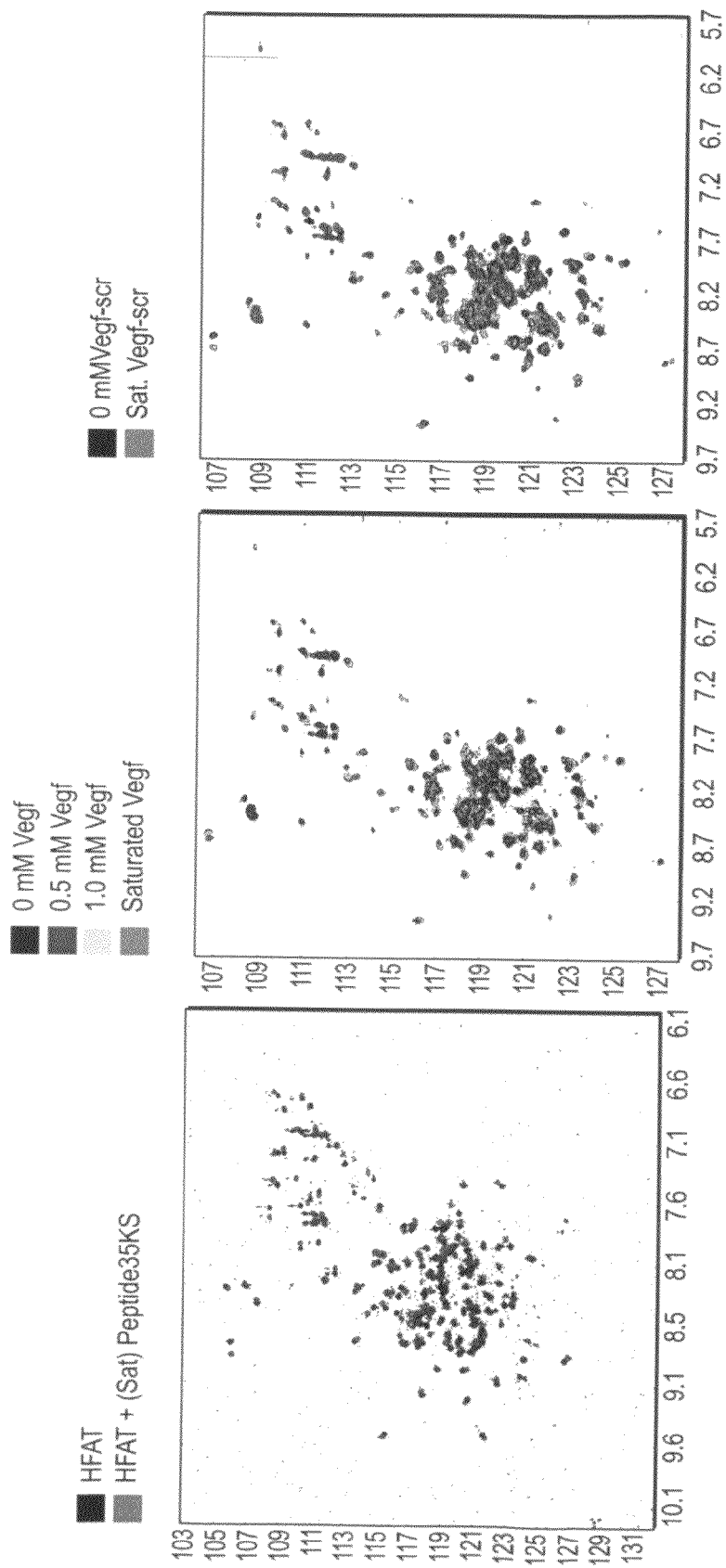
FIG. 1.4

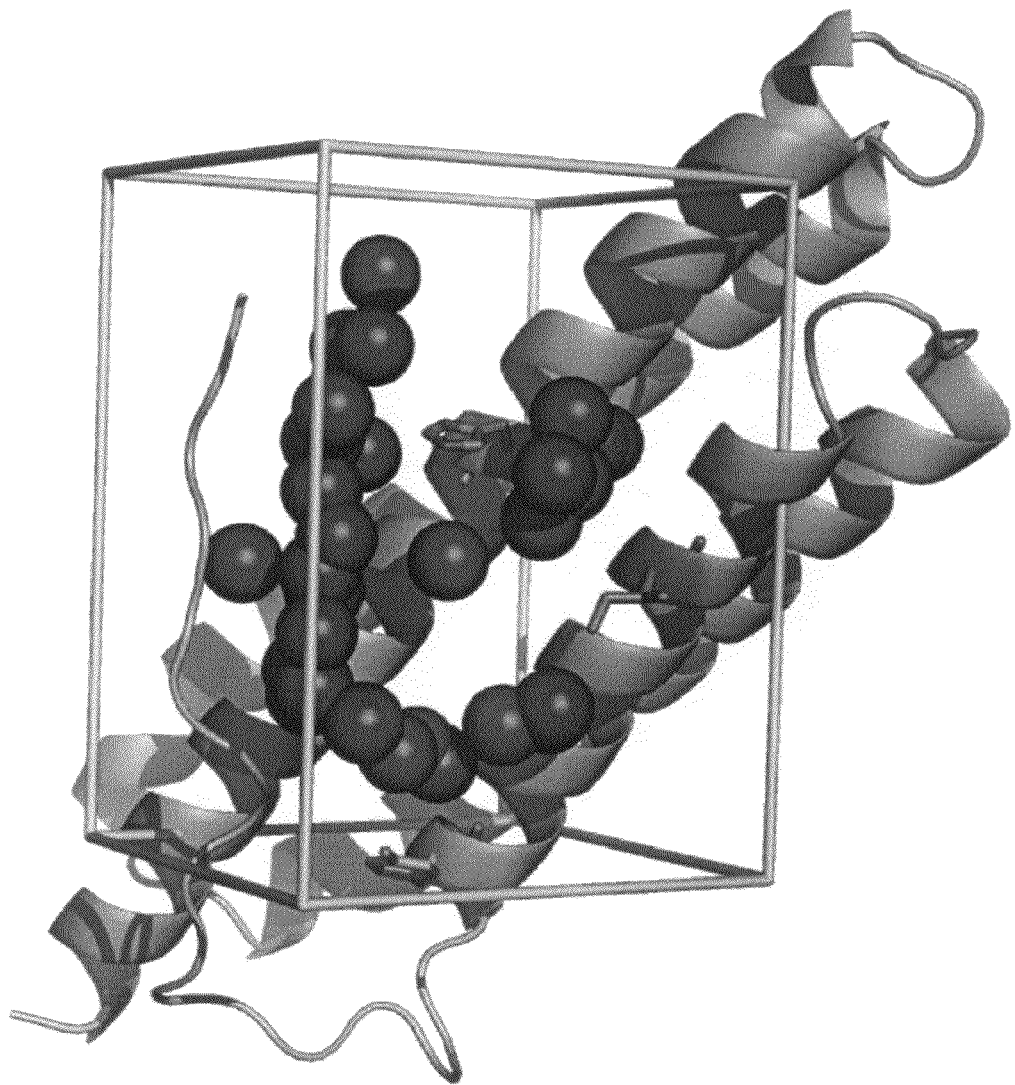
FIG. 1.5

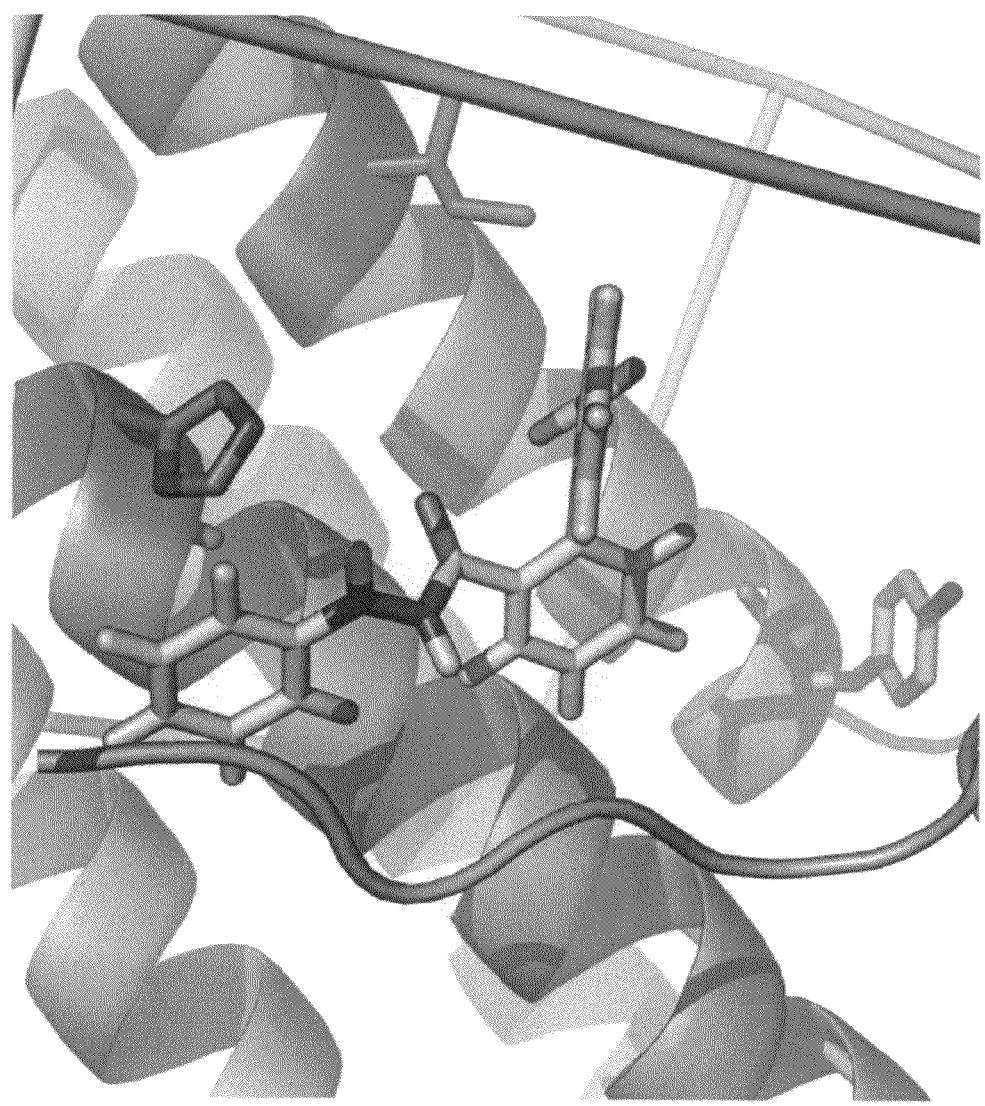
FIG. 1.6

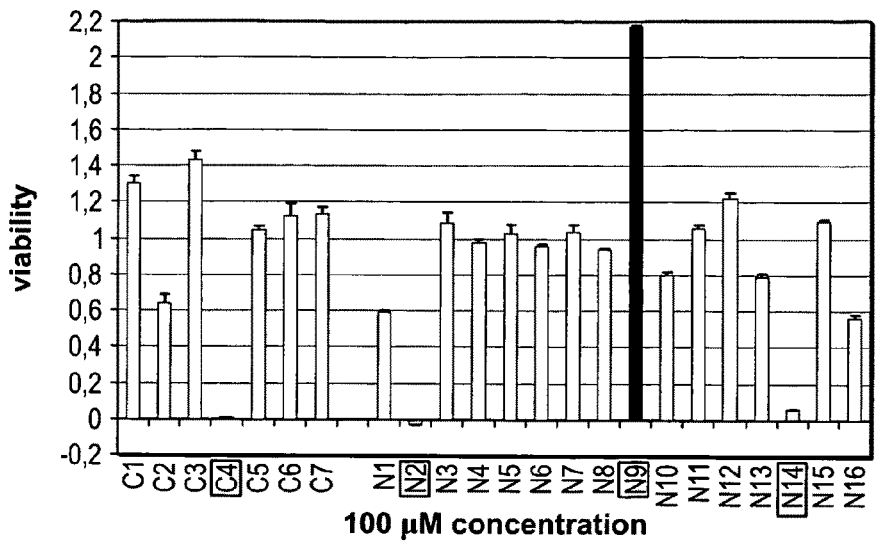
FIG. 1.7A
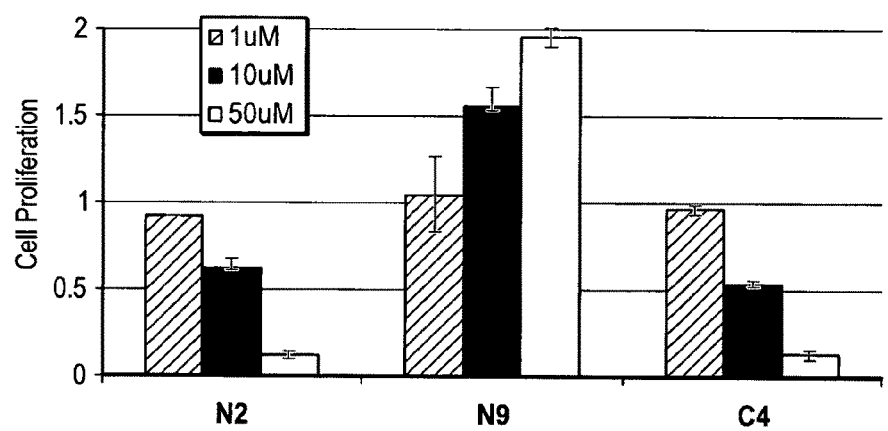
FIG. 1.7B
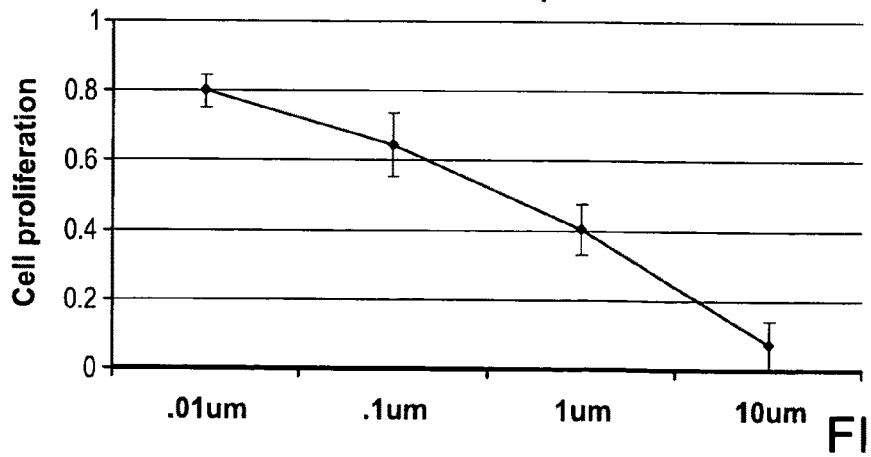
FIG. 1.7C

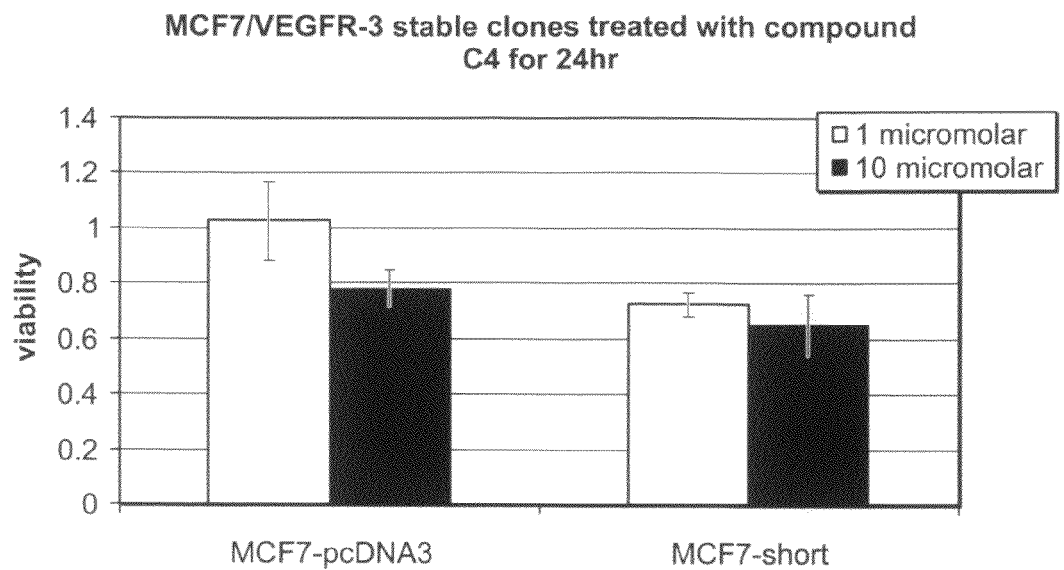
FIG. 1.8A
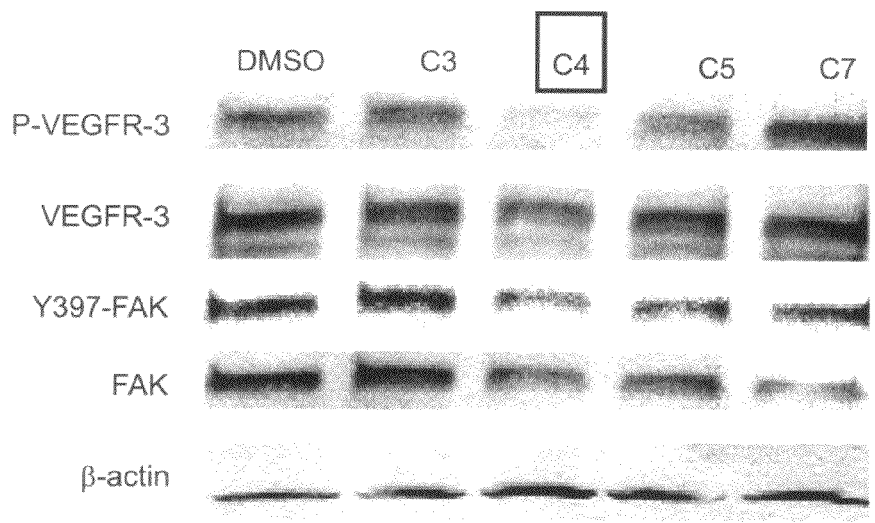
FIG. 1.8B

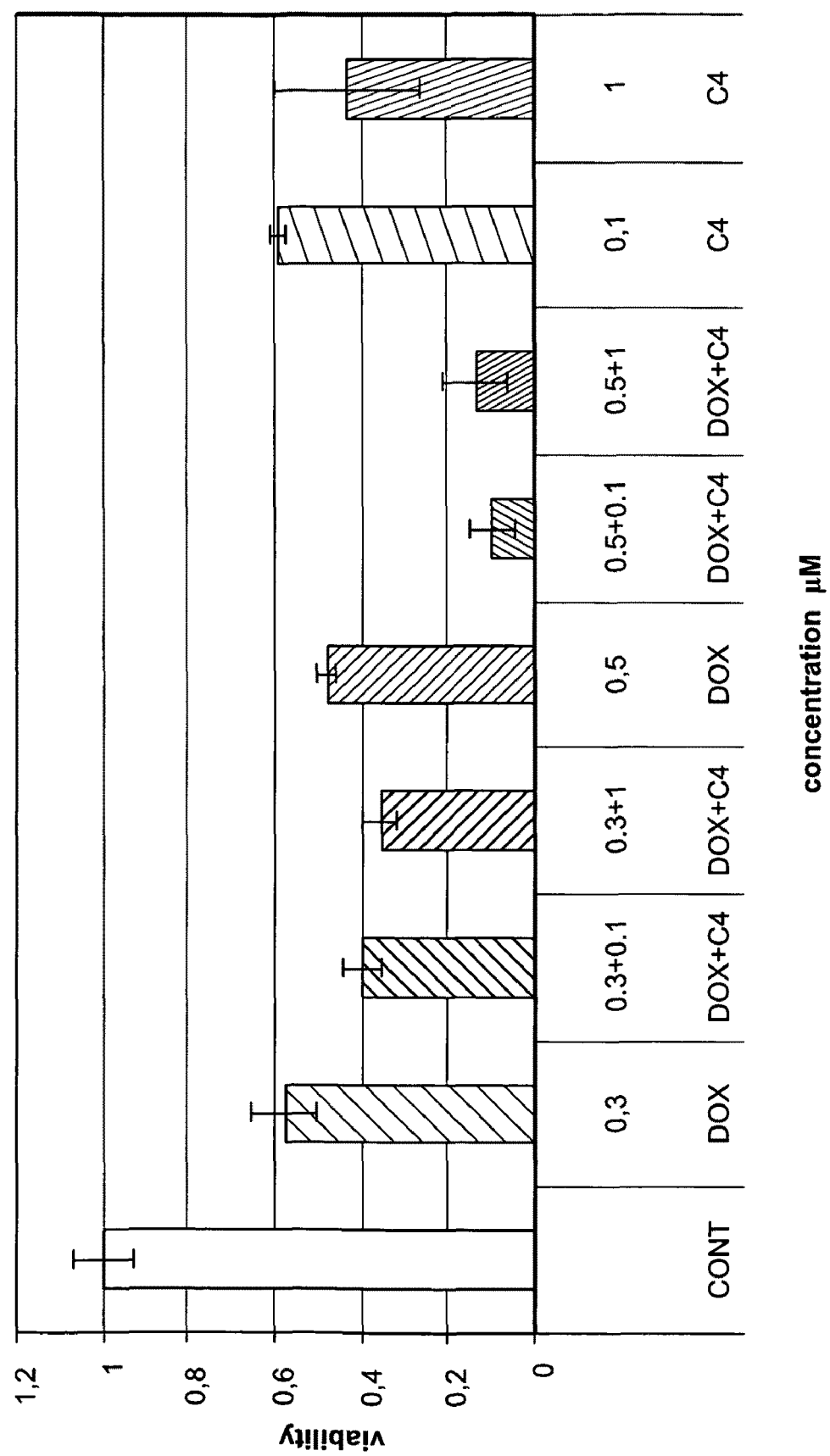
FIG. 1.9

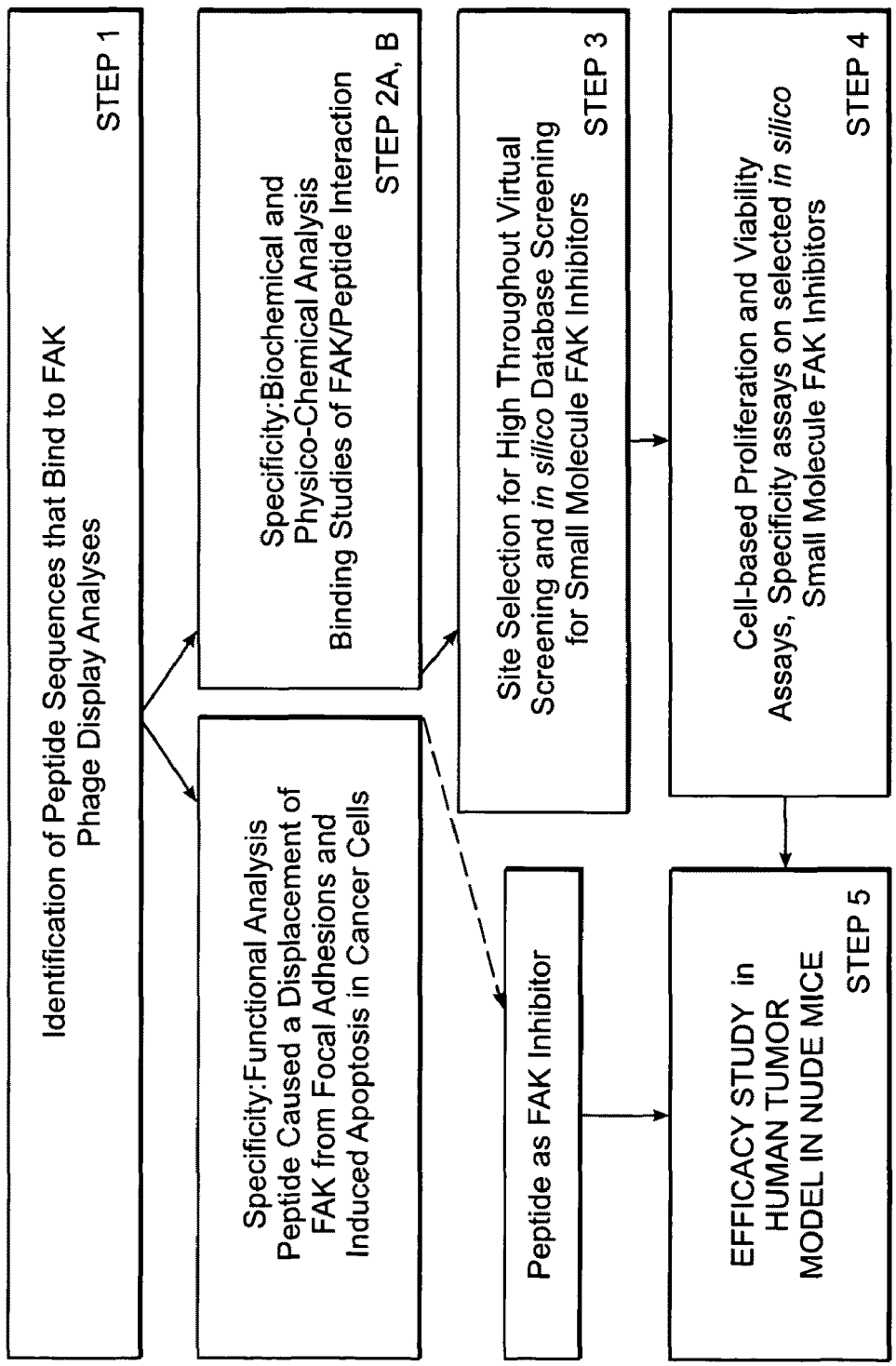
FIG. 1.10

KINASE MODULATING COMPOUNDS AND USES THEREOF FOR TREATMENT OF CANCER

CROSS REFERENCE TO RELATED APPLICATIONS

This application claims priority as a continuation-in-part application of PCT International Application PCT/US2008/003451, filed Mar. 14, 2008, which claims benefit of U.S. Provisional Patent Application No. 60/918,615 filed Mar. 16, 2007 and U.S. Provisional Patent Application No. 61/069,248, filed Mar. 12, 2008, the contents of each are hereby incorporated by reference in their entirety.

STATEMENT OF RIGHTS TO INVENTIONS MADE UNDER FEDERALLY SPONSORED RESEARCH

This work was supported in part by a National Institutes of Health/NCI Grant, Grant No. 2-R01-CA65910-09-13. The government has certain rights in the invention.

BACKGROUND OF THE INVENTION

Focal Adhesion Kinase (FAK) is an important survival molecule that is upregulated in a broad range of solid tumors and is expressed at very low levels in normal tissues, creating a therapeutic window and making this protein a highly attractive target for the treatment of cancer, as suggested by our lab [1] and recently by other leading authors in the field [2.3]. See also WO 2005/049852, the contents of which are incorporated by reference. We have identified the key-binding partners of FAK and peptides from the binding sites that cause apoptosis in cancer but not normal cells. Based on these findings as well as correlative structural and functional data, we suggest that blocking FAK-protein interactions will lead to apoptosis and tumor cell death. We have well-documented data that targeting FAK interactions is important for cell survival, and we have used atomic resolution structural data of specific binding sites to identify small molecule lead compounds. We have screened small molecule libraries and identified several lead compounds that disrupt binding of FAK to key signaling molecules and induce apoptosis in breast, colon, pancreatic, lung, as well as melanoma cancer cell lines. Some of these compounds caused apoptosis at low nanomolar concentrations. We also have shown that lead compounds increase the sensitivity of cancer cells to standard chemotherapy drugs.

Our data suggest that peptides and small molecule inhibitors of FAK can be identified as lead compounds to provide the basis for targeted novel cancer therapeutic agents. Such compounds will effectively reduce activation of both molecules involved in survival signaling and will lead to cancer cell death and sensitivity to chemotherapy. We anticipate that our approach (targeting FAK protein-protein interactions) is amenable to more successful drug discovery and development than the typical method of targeting the kinase activity by targeting ATP binding site of tyrosine kinases. Experience shows that it is especially difficult in the case of FAK, as several large pharmaceutical companies have failed to develop specific inhibitors of FAK that target kinase activity due to cross-reactivity with other essential tyrosine kinases.

The market for novel drug therapy targeting cancers of the breast, colon, pancreas, and thyroid is extensive. According to the American Cancer Society, it is estimated that 425,000 new cases of these cancers will be diagnosed this year in this country alone. Cancer drug therapy is an existing major product line of several pharmaceutical companies, and the development of drugs targeting FAK would be a natural complement to their existing products.

FAK is overexpressed in many cancer types compared to other kinase targets. Compounds that target FAK could be prescribed for many cancer types including breast, colon, pancreas, thyroid, lung, and melanoma.

Several groups are exploring the targeting of FAK as potential cancer therapeutics. The targeting of FAK typically has been focused on the kinase domain of FAK. This approach has proven unsuccessful as disruption of the kinase domain does not specifically interfere with the signaling downstream of FAK and other related tyrosine kinases have been affected by the drugs. Delineated herein is a novel approach that investigates the protein-protein interactions that are very specific for downstream signaling of FAK. Furthermore, targeting different binding partners of FAK might be relevant to different types of tumors.

Our laboratory was the first to clone human Focal Adhesion Kinase in 1993 and demonstrate its upregulation in different human tumors [4.5]. Based on knowledge of FAK biology in normal and tumor cells, we have identified the protein-protein interactions of FAK as targets for small-molecule-based tumor therapy. Phage display analyses revealed many potential FAK binding partners, some of which we already discovered by different approaches (e.g., p53) [6] and some we characterized based on phage display data (e.g., VEGFR3) [7]. Many of the selected peptides caused loss of viability and apoptosis in cancer but not in normal cells in vitro. These results suggest that it may occur by mimicking binding sites for key partners of FAK. We are focusing on three key structural interactions of FAK and specific binding sites. The advantage of our approach is twofold: we have well-defined data that targeting FAK interactions is important for cell survival, and we have used atomic resolution structural data of specific binding sites to identify small molecule lead compounds[8-10]. We are utilizing these data for structural analyses of FAK binding to these small molecules. We have also developed a novel computational technique that can be applied to a wide variety of biomedically relevant target proteins [11, 12]. This method, called NCIDOCK, utilizes the atomic coordinates for the target protein as the basis for large-scale molecular docking experiments in which approximately 140,000 small molecules are positioned into specific structural features. Each compound is scored for its estimated binding energy to the target, and then ranked to generate a list of candidate lead compounds. We then request the top-ranked small molecules for functional testing.

We have performed preliminary screening of a chemical library of 240,000 such compounds for each of three selected binding sites of key partners of FAK and identified a series of small molecules that we have evaluated for inhibition of FAK function, followed by application of our extensive experience in FAK biology and our already evaluated model systems to perform multiple cell-based assays (viability, proliferation, motility and invasion, cell cycle and apoptosis) for the analysis of biological activity of the lead compounds. We examined cancer cell lines (e.g., breast, colon, pancreatic, lung, or melanoma human) with these selected FAK inhibitors and have reproducibly shown a significant decrease of tumor cell viability and increase in tumor cell death in vitro.

SUMMARY OF THE INVENTION

In one aspect, the invention provides a method of treating a subject suffering from or susceptible to a cell proliferative disorder comprising administering to subject in need thereof a therapeutically effective amount of a compound capable of modulating FAK protein-protein binding interactions. In one embodiment, the compound is capable of binding to or interacting with a binding pocket that affects FAK binding with human p53 peptide. In another embodiment, the compound is capable of binding to or interacting with a binding pocket that affects FAK binding with receptor interacting protein RIP or vascular endothelial growth factor receptor 3 VEGFR-3.

In one embodiment, the compound is capable of binding to or interacting with a binding pocket defined by structure coordinates of human p53 peptide. In another embodiment, the compound is capable of binding to or interacting with a binding pocket defined by structure coordinates of receptor interacting protein RIP or vascular endothelial growth factor receptor 3 VEGFR-3.

In one aspect, the compound is capable of modulating the binding interaction between human p53 and FAK-NT. In one aspect, the compound is capable of modulating the binding interaction between human p53 and aminos acids 206-405 of FAK-NT. In one aspect, the compound is capable of modulating binding interaction at one or more of the following residues of FAK: R86, E93, V95, W97, R127, F147, Q150, D154, E158, Y251, F253, E256, C257, F258, K259, P332, I336, N339.

In one aspect the compound is human p53 peptide, or fragment thereof. In another aspect, the compound comprises the amino acid sequence that is amino acids 43-73 of human p53. In another aspect, the compound comprises the amino acid sequence that is amino acids 65-71 of human p53. In another aspect, the compound comprises the amino acid sequence QMSGAPH (SEQ ID NO: 3). In another aspect the compound is a p53 peptide fragment comprising the amino acid sequence QMSGAPH (SEQ ID NO: 3). In another aspect, the compound comprises one of the following amino acid sequences: (i) QMSAAPA (SEQ ID NO: 4), (ii) RMPEAAP (SEQ ID NO: 5), or (iii) RVSGAPA (SEQ ID NO: 6).

In one aspect, the compound is capable of binding with human p53 peptide, or fragment thereof. In another aspect, the compound is capable of binding with the amino acid sequence that is amino acids 43-73 of human p53. In another aspect, the compound is capable of binding with the amino acid sequence that is amino acids 65-71 of human p53. In another aspect, the compound is capable of binding with the amino acid sequence QMSGAPH (SEQ ID NO: 3). In another aspect, the compound is capable of binding with a p53 peptide fragment comprising the amino acid sequence QMSGAPH (SEQ ID NO: 3). In another aspect, the compound is capable of binding with a compound comprising one of the following amino acid sequences: (i) QMSAAPA (SEQ ID NO: 4), (ii) RMPEAAP (SEQ ID NO: 5), or (iii) RVSGAPA (SEQ ID NO: 6).

In one aspect, the invention provides a method of treating a subject suffering from or susceptible to a cell proliferative disorder. The method includes administering to a subject in need thereof a therapeutically effective amount of a FAK binding inhibitor compound.

In another aspect, the invention provides a method of treating a subject suffering from or susceptible to a cell proliferative disorder. The method includes administering to a subject in need thereof a therapeutically effective amount of a compound capable of modulating FAK protein-protein binding interactions by directly modulating the FAK binding partner's binding ability.

In another embodiment, the invention provides a method of treating a subject suffering from or susceptible to a cell proliferative disorder. The method includes administering to a subject identified as in need thereof a therapeutically effective amount of a FAK inhibitor compound or a FAK binding partner inhibitor compound.

In another aspect, the invention provides a method of treating a subject suffering from or susceptible to a cell proliferative disorder, including cancer. The method includes administering to a subject in need thereof a therapeutically effective amount of a compound capable of binding to a the FAT domain of FAK or a FAK protein binding partner.

In another aspect, the invention provides a method of treating a subject suffering from or susceptible to cancer, comprising administering to the subject an effective amount of a compound capable of disrupting FAK binding (including with FAK-binding partners), such that the subject is treated.

In another aspect, the invention provides a method of treating a subject suffering from or susceptible to a disorder comprising administering to subject in need thereof a therapeutically effective amount of a compound capable of modulating proliferation, wherein the compound stimulates proliferation. In other aspects, the method comprises stimulating FAK protein-protein binding interactions.

In another aspect, the invention provides a method for identifying a compound that modulates FAK protein-protein binding interaction, the method comprising obtaining a crystal structure of a FAK protein or FAK protein binding partner (e.g., VEGFR-3, RIP, p53) or obtaining information relating to the crystal structure of a FAK protein or FAK protein binding partner, and modeling a test compound into or on the FAK protein or FAK protein binding partner structure to determine whether the compound modulates the interaction of a FAK protein-protein binding. In certain embodiments, the step of modeling comprises modeling or determining the ability of the compound to bind to or associate with a binding pocket defined by structure coordinates of the FAT domain of FAK or a FAK protein binding partner.

Yet another aspect of the invention is a method for identifying a compound that inhibits cell proliferation. The method includes contacting a focal adhesion targeting domain (FAT) complex with a test compound, and evaluating the ability of the test compound to modulate (e.g., inhibit), the FAT domain of FAK, inhibit cell proliferation, induce apoptosis, or modulate FAK binding with a FAK protein binding partner.

Yet another aspect of the invention is a method for identifying a compound that modulates the activity of FAK, the method comprising using the atomic coordinates of the FAT domain of FAK, to generate a three-dimensional structure (e.g., in silico) of a molecule comprising a binding pocket, and employing the three-dimensional structure to identify a compound that modulates the activity of the FAT domain of FAK or modulate FAK binding with a FAK protein binding partner.

In another aspect, the invention provides a packaged composition including a therapeutically effective amount of a FAK inhibitor or FAK protein-protein binding interaction inhibitor compound and a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In one aspect, the invention provides a kit for treating a cell proliferative disorder in a subject is provided and includes a compound herein, a pharmaceutically acceptable esters, salts, and prodrugs thereof, and instructions for use. In further aspects, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In certain embodiments, the invention provides: a kit for treating a cell proliferative disorder in a subject, the kit comprising a compound capable of modulating (e.g., inhibiting) FAK activity or FAK protein-protein binding interactions.

In another aspect, the invention relates to a three-dimensional structure of a FAT domain of FAK, or a FAK protein binding partner, each alone or combinations thereof.

Thus, the present invention provides molecules or molecular complexes that comprise either one or both of these binding pockets or homologues of either binding pocket that have similar three-dimensional shapes.

The invention also provides a pharmaceutical compositions of the compounds described herein, comprising a compound capable of modulating the activity of the FAT domain of FAK or modulate FAK binding with a FAK protein binding partner, or a pharmaceutically acceptable ester, salt, or prodrug thereof, together with a pharmaceutically acceptable carrier.

In another aspect, the invention provides a machine readable storage medium which comprises the structural coordinates of a binding pocket defining the FAT domain of FAK or modulate FAK binding with a FAK protein binding partner, or a homologous binding pocket.

In another aspect, the invention provides a computer for producing a three-dimensional representation of a molecule or molecular complex, wherein said molecule or molecular complex comprises a binding pocket defined by structure coordinates of the FAT domain of FAK or a FAK protein-protein binding partner; or b) a three-dimensional representation of a homologue of said molecule or molecular complex, wherein said homologue comprises a binding pocket that has a root mean square deviation from the backbone atoms of said amino acids of not more than about 2.0 angstroms. The computer includes: (i) a machine-readable data storage medium comprising a data storage material encoded with machine-readable data, wherein said data comprises the structure coordinates of the FAT domain of FAK or a FAK protein-protein binding partner; (ii) a working memory for storing instructions for processing said machine-readable data; (iii) a central-processing unit coupled to said working memory and to said machine-readable data storage medium for processing said machine readable data into said three-dimensional representation; and (iv) a display coupled to said central-processing unit for displaying said three-dimensional representation.

The invention also provides methods for designing, evaluating and identifying compounds which bind to the aforementioned binding pockets. Other embodiments of the invention are disclosed infra.

In other aspects, the computer delineated here includes those:

wherein the binding pocket defined by structure coordinates of the FAT domain of FAK or a FAK protein-protein binding partner is defined by structure coordinates of the FAT domain of FAK in Table 2;

wherein the binding pocket defined by structure coordinates of the FAT domain of FAK or a FAK protein-protein binding partner is a representation based on structure coordinates of the FAT domain of FAK in Table 2;

Another aspect is a method for identifying a compound that modulates the interaction of FAK binding or FAK protein-protein interaction binding, the method comprising preparing a three-dimensional representation of a binding pocket having the spatial orientation of a binding pocket in the three-dimensional structure coordinates of Table 2; and modeling a test compound into or on the three-dimensional representation of a binding pocket to determine whether the compound modulates the interaction of FAK, FAK binding partners or domains thereof.

In other aspects, the methods delineated here includes those:

wherein the modeling comprises preparing a three-dimensional representation of a test compound and evaluating the binding interactions of the test compound and binding pocket;

wherein the modeling comprises preparing a three-dimensional representation of a test compound and evaluating the binding interactions of the test compound and binding pocket;

wherein the test compound is further assessed in vitro or in vivo;

wherein the binding pocket comprises one or more of the FAK FAT domain amino acids that interact with compound C4 in the three-dimensional structure coordinates of Table 2; and wherein the binding pocket comprises one of the FAK FAT domain amino acids that interact with compound C4 in the three-dimensional structure coordinates of Table 2.

BRIEF DESCRIPTION OF THE DRAWINGS

The present invention is further described below with reference to the following non-limiting examples and with reference to the following figures, in which:

FIG. 1. Is a poster panel describing development of anti-cancer agents focusing on Focal Adhesion Kinase mechanistic pathway.

DETAILED DESCRIPTION OF THE INVENTION

Figure 2:
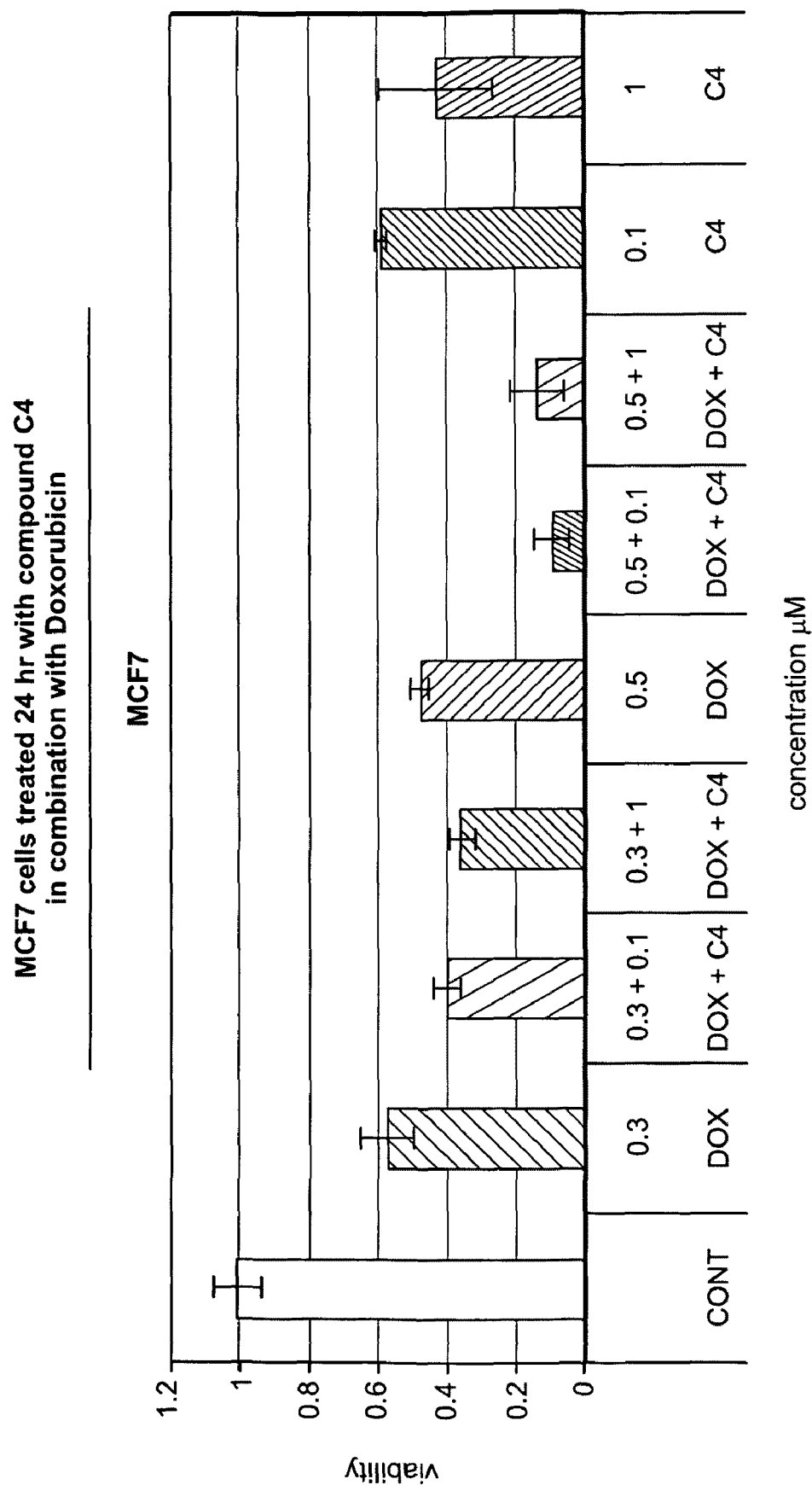
FIG. 2. depicts of results of test compound C4 in combination with doxorubicin as an anticancer combination.
Figure 3:
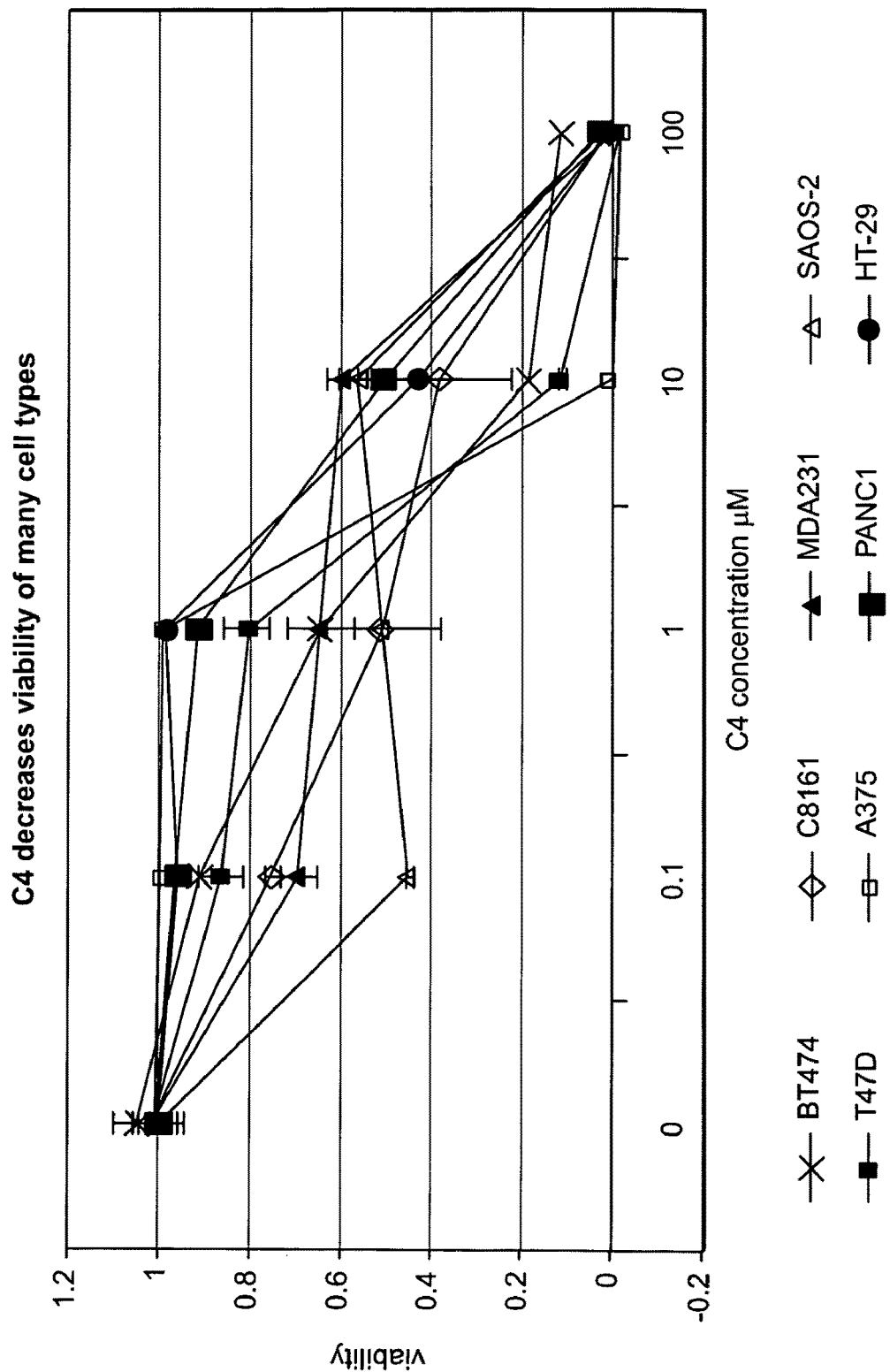
FIG. 3. depicts effect of C4 on cell viability.
Figure 4:
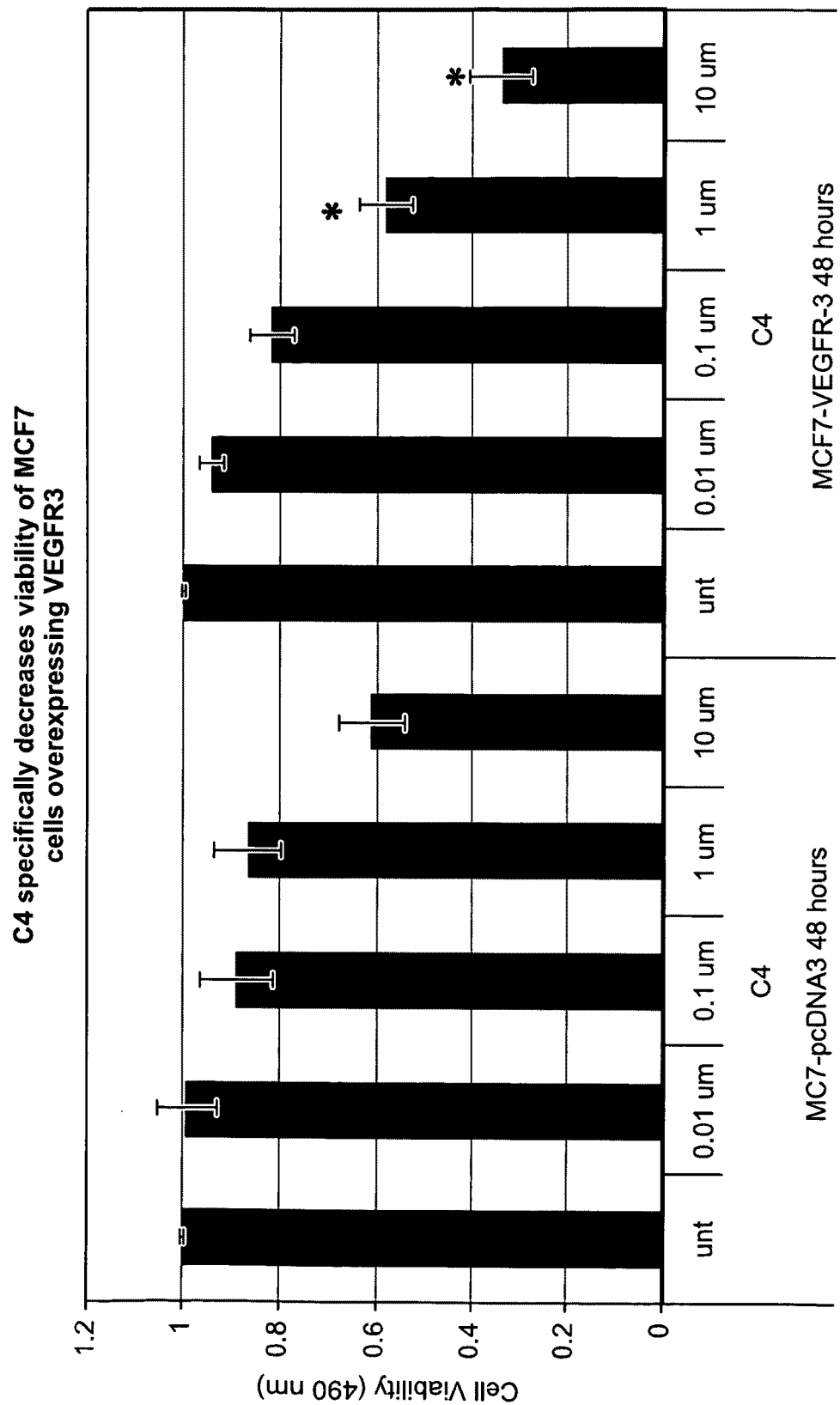
FIG. 4. depicts effect of C4 on MCF7 cell viability.
Figure 5:
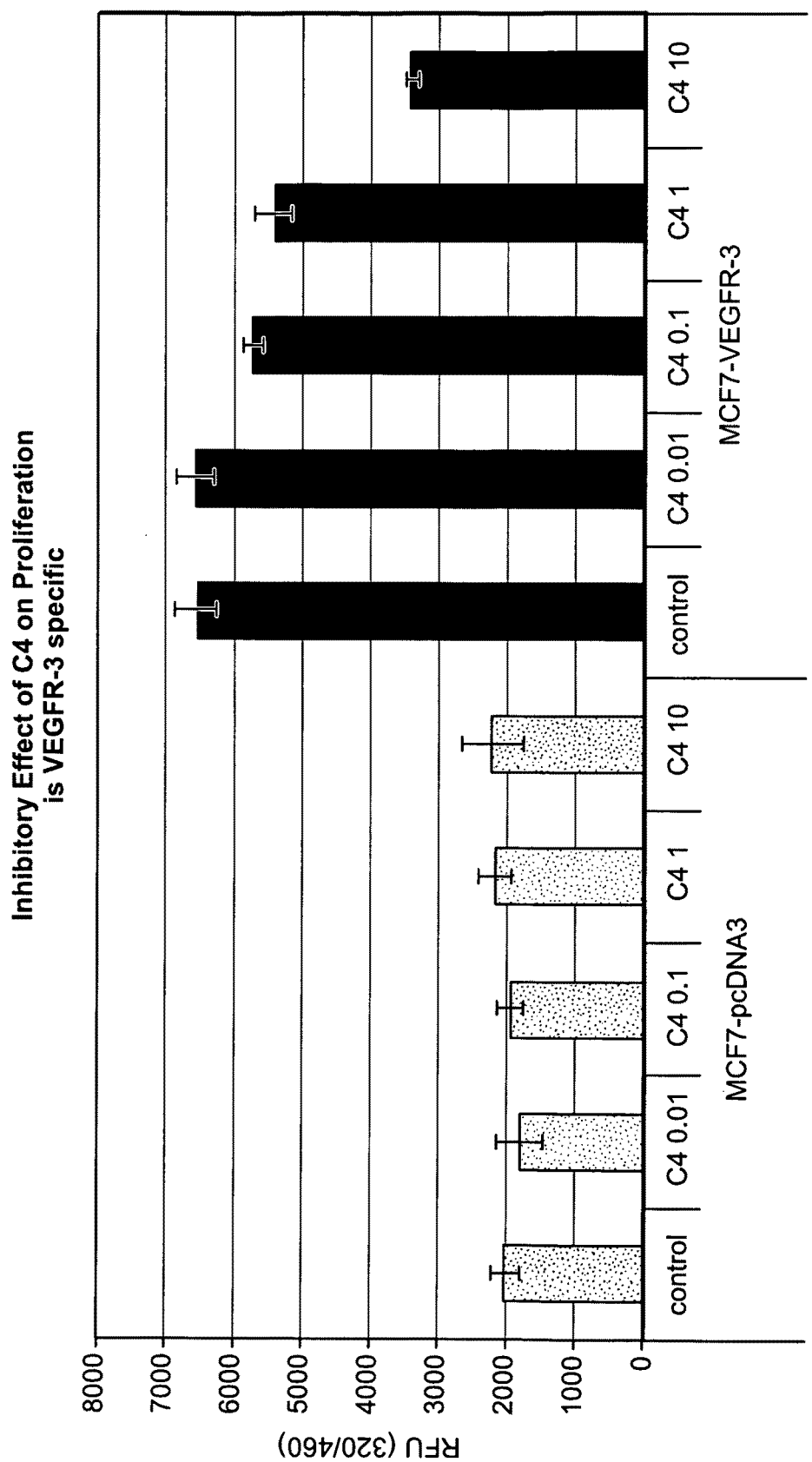
FIG. 5. depicts effect of C4 on VEGFR-3 specificity.
Figure 6:
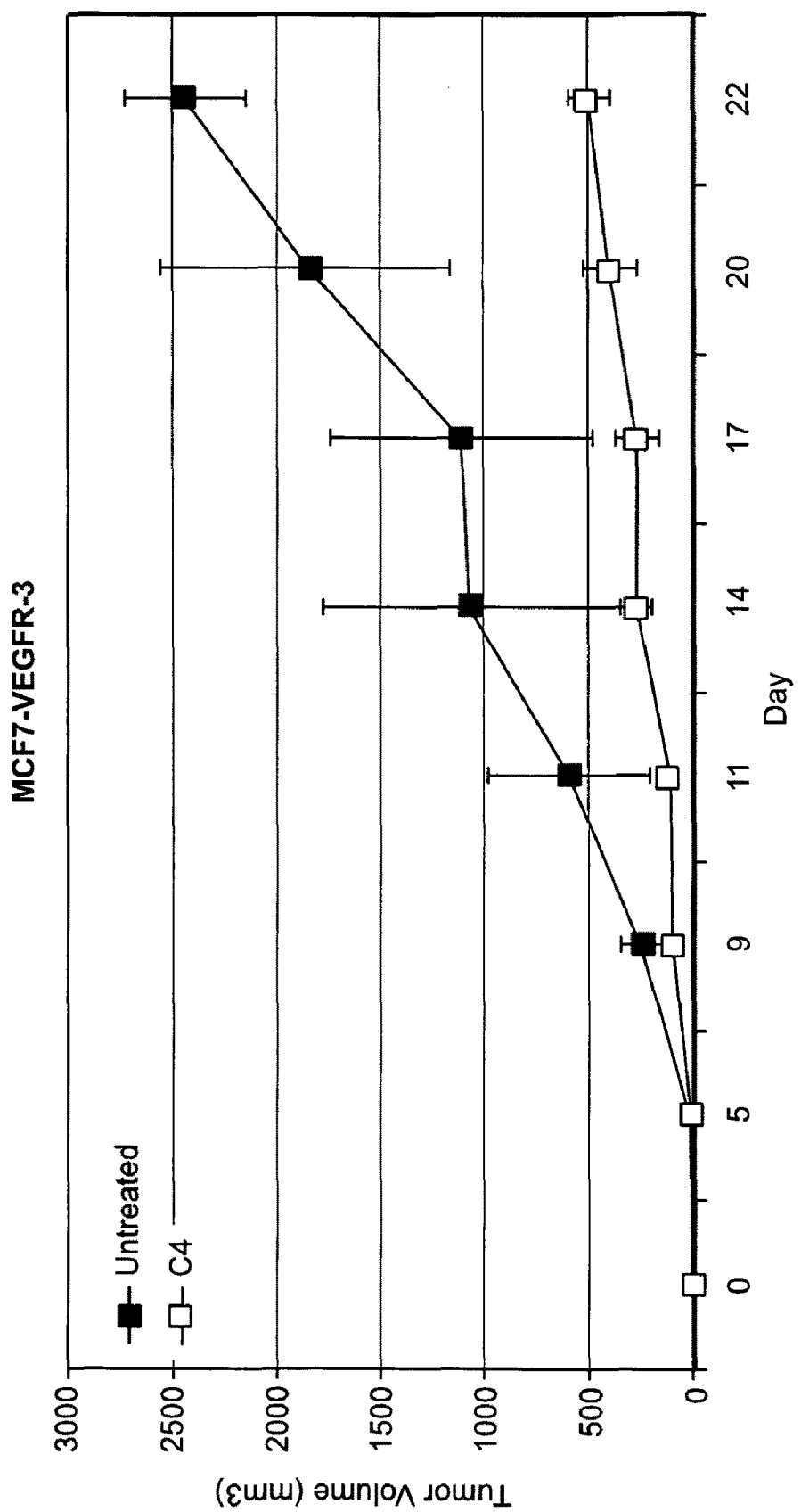
FIG. 6. depicts effect of C4 on tumor growth in vivo.
Figure 7:
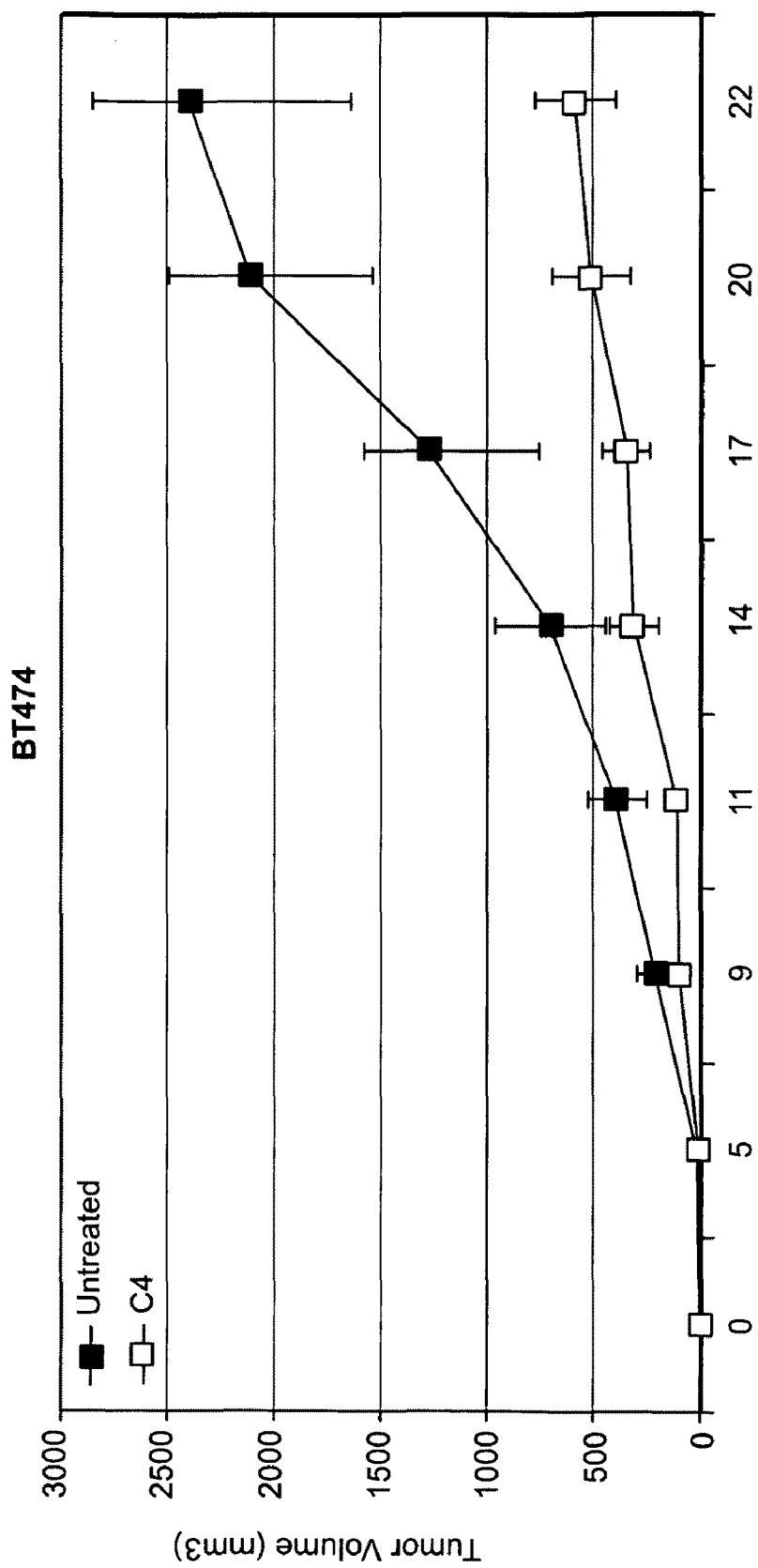
FIG. 7. depicts effect of C4 on tumor growth in vivo.
Figure 8:
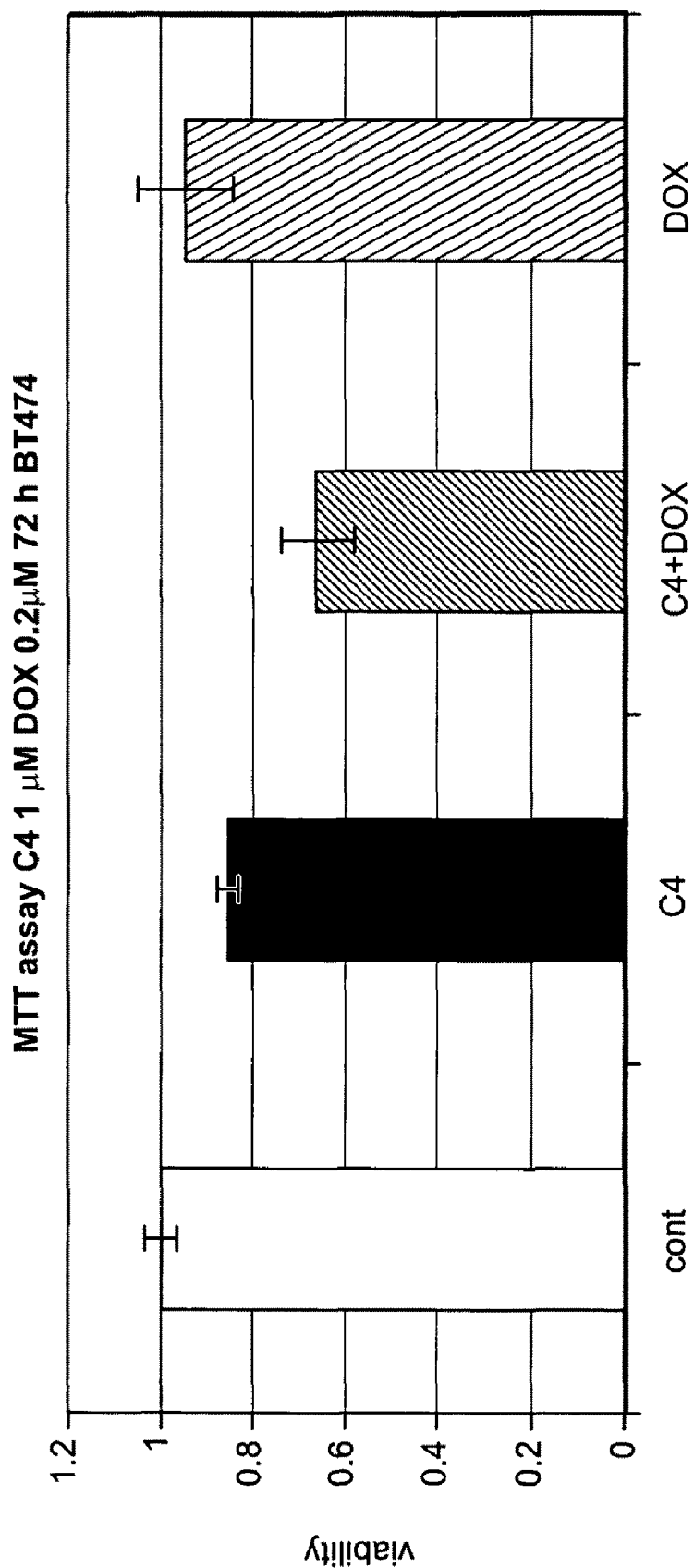
FIG. 8. depicts effect of C4 in combination with doxorubicin on cell viability.
Figure 9:
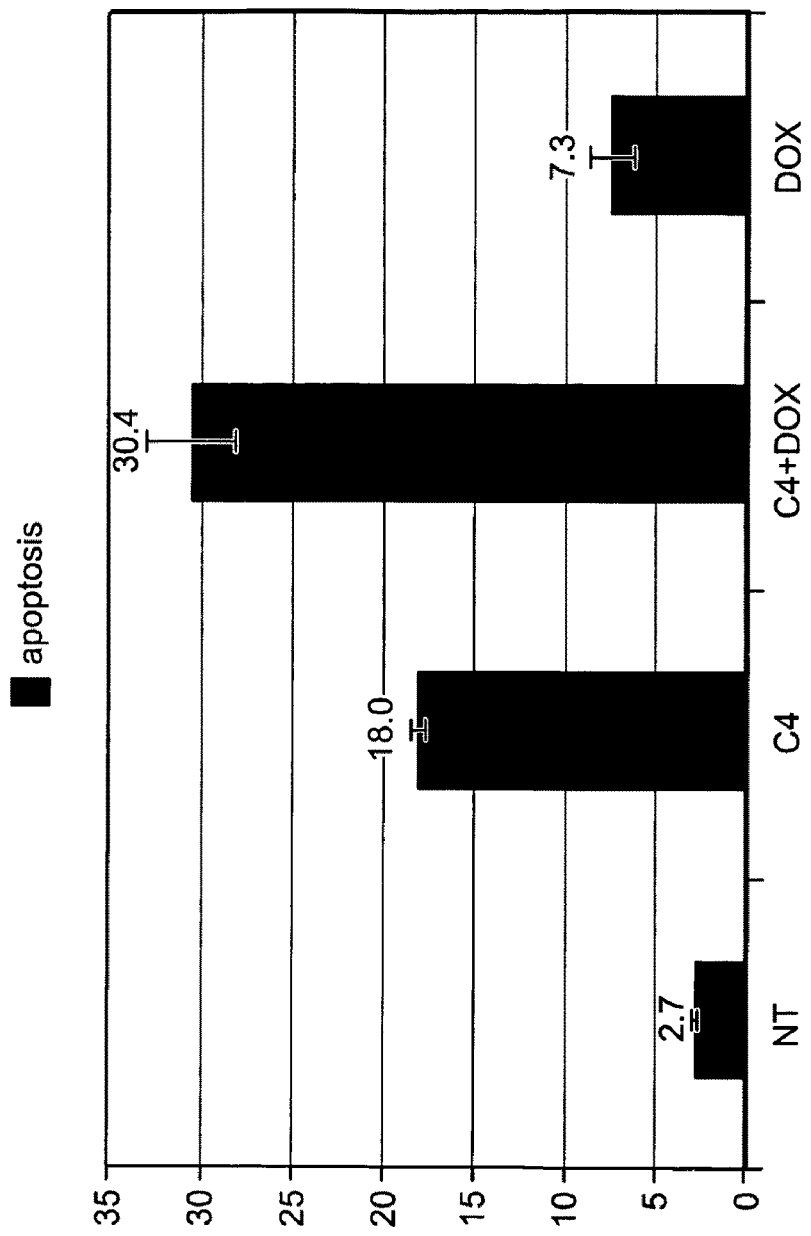
FIG. 9. depicts effect of C4 in combination with doxorubicin on cell apoptosis.
Figure 10:
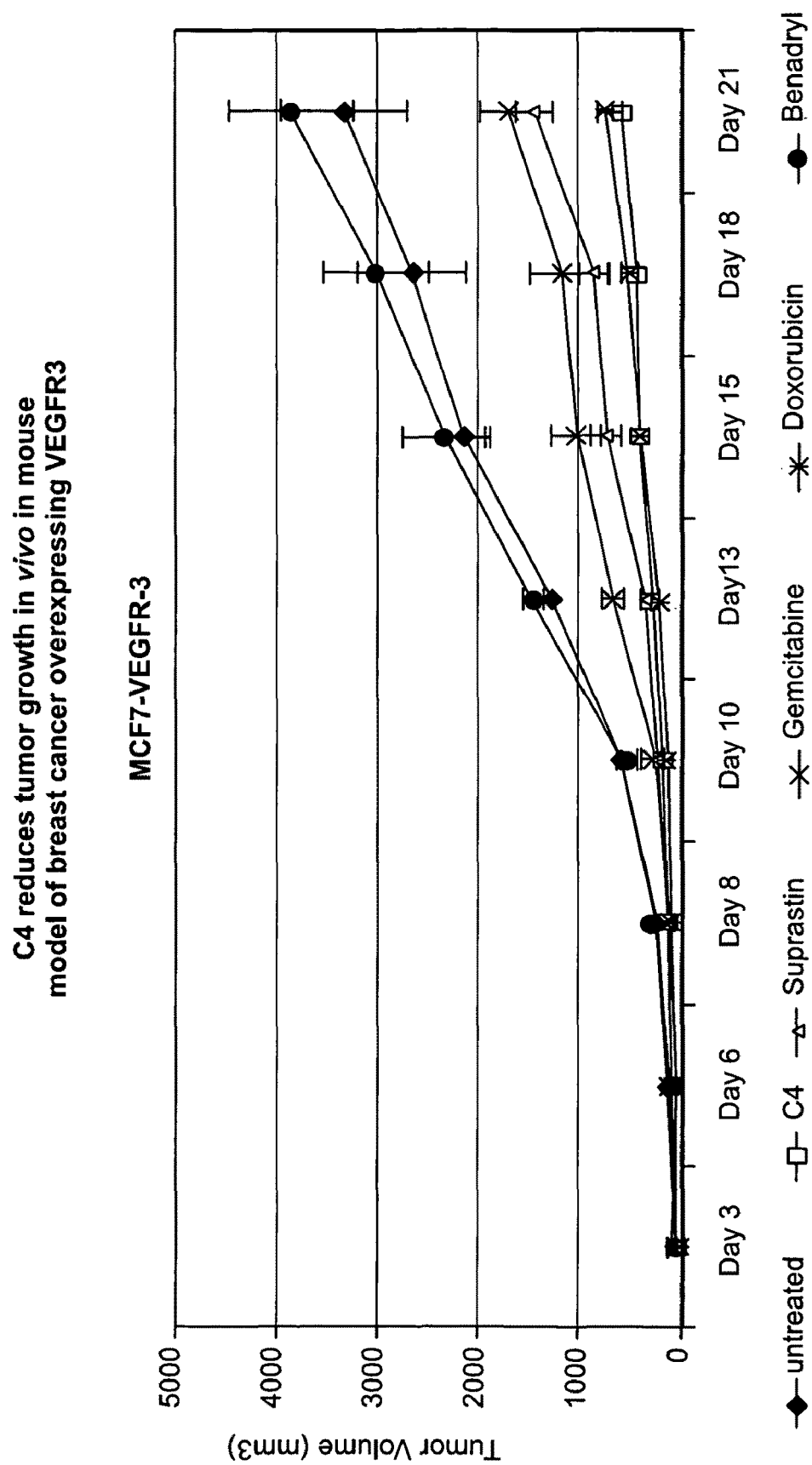
FIG. 10. depicts effect of C4 on tumor growth in vivo.
Figure 11:
FIG. 11. depicts C4 sensitizing effect on pancreatic cancer cells.
Figure 12:
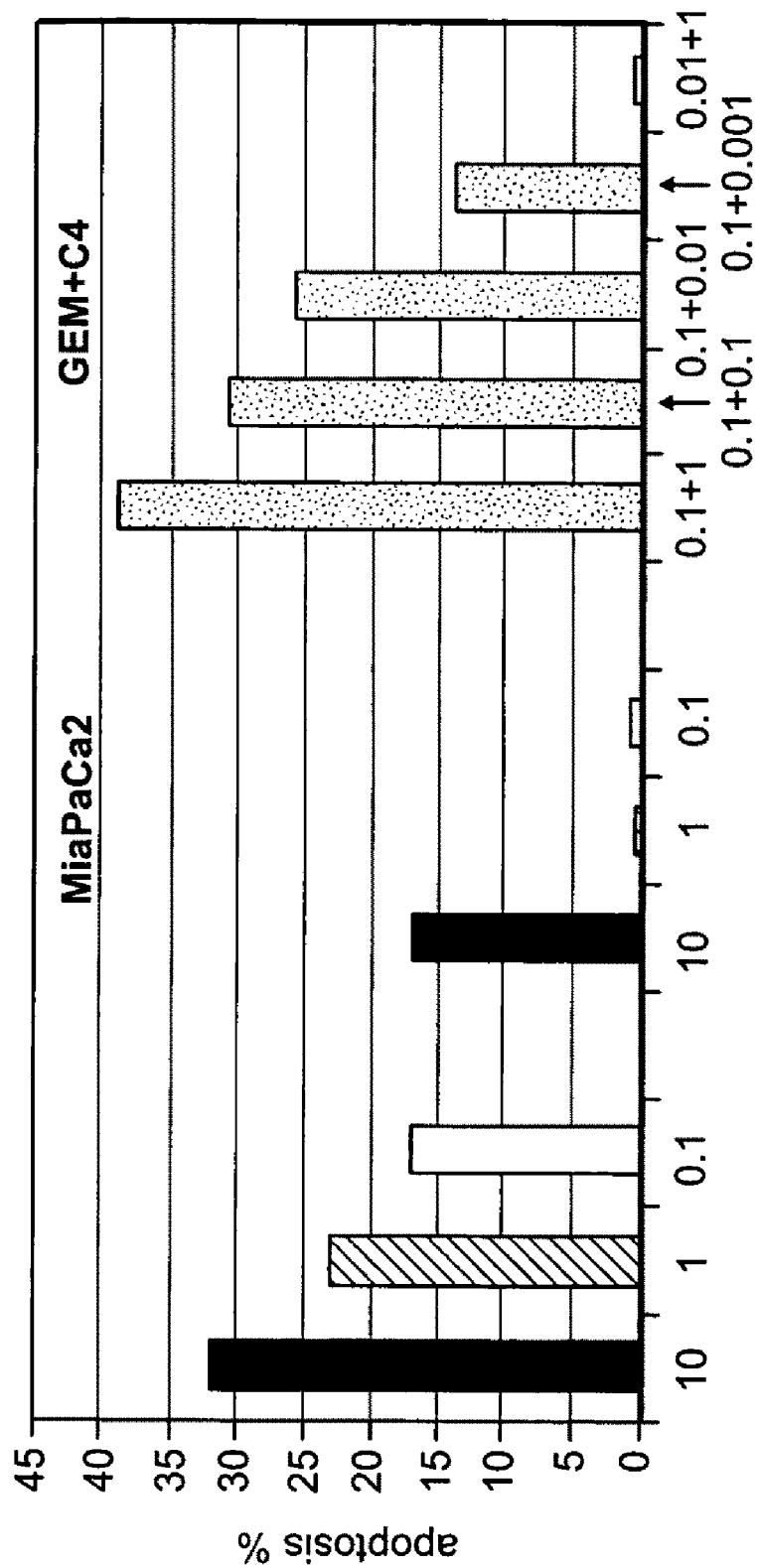
FIG. 12. depicts C4 sensitizing effect on pancreatic cancer cells.
Figure 13:
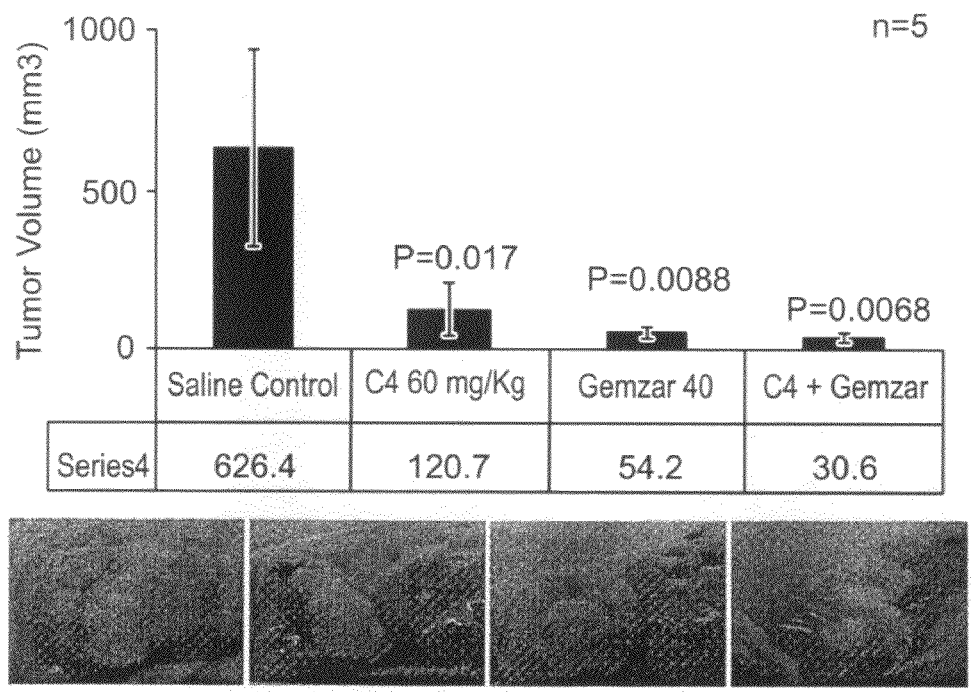
FIG. 13. depicts C4 effect in vivo on pancreatic cancer cells.
Figure 14:
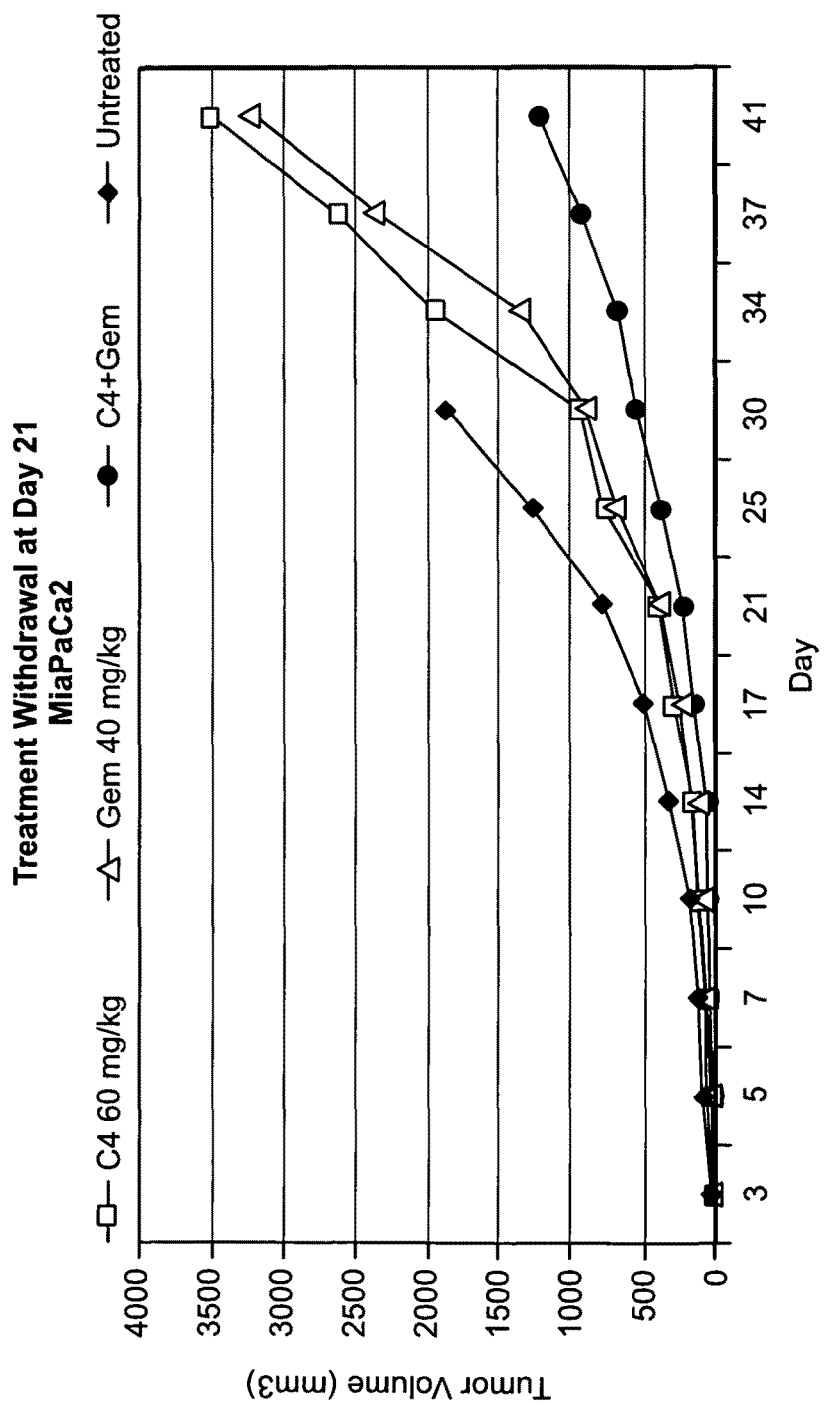
FIG. 14. depicts C4 effect in vivo on pancreatic cancer cells.
Figure 15:
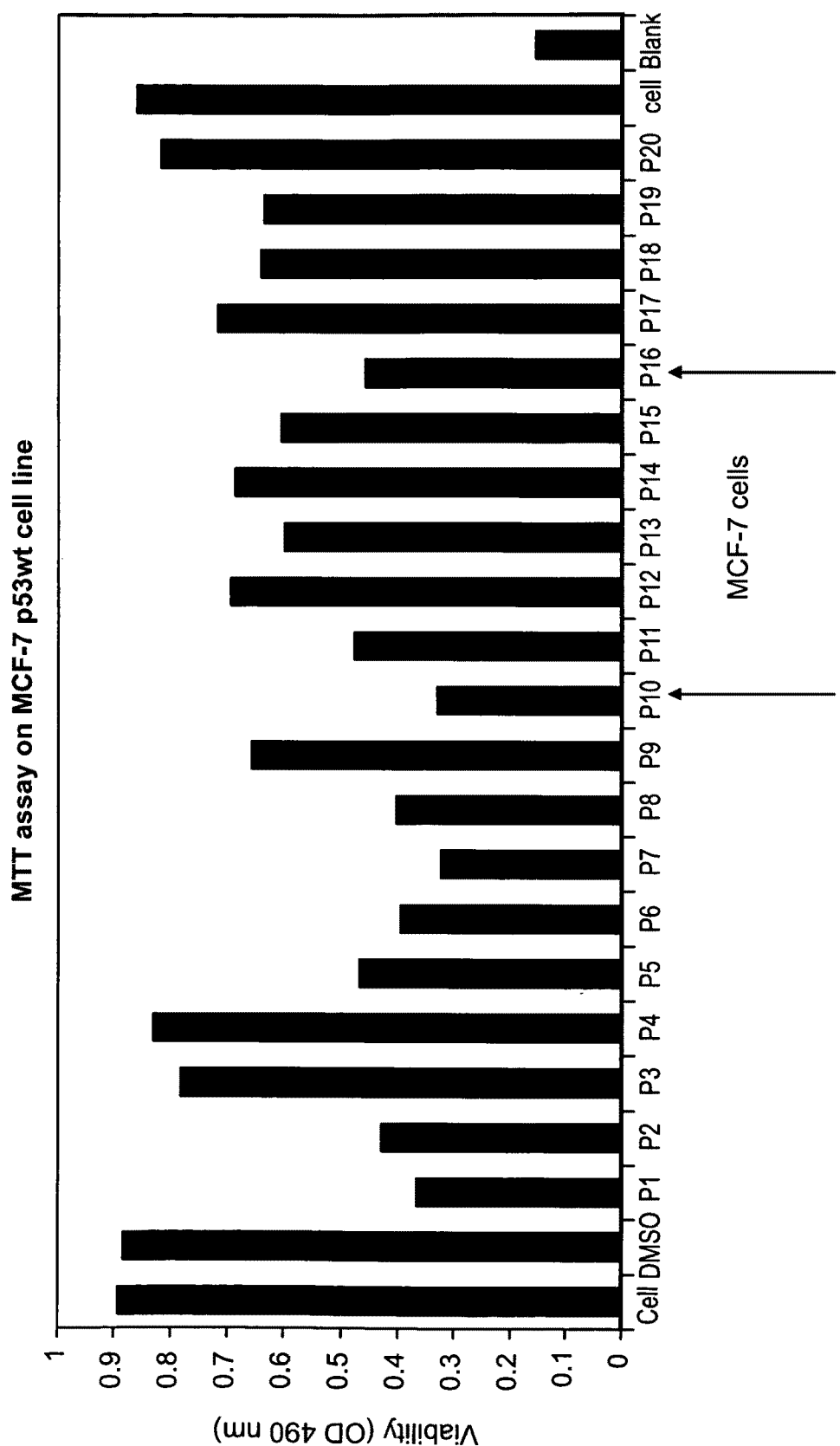
FIG. 15. depicts MTT assay results for P-compounds on MCF-7 p53 (wild type) cell line.
Figure 16:
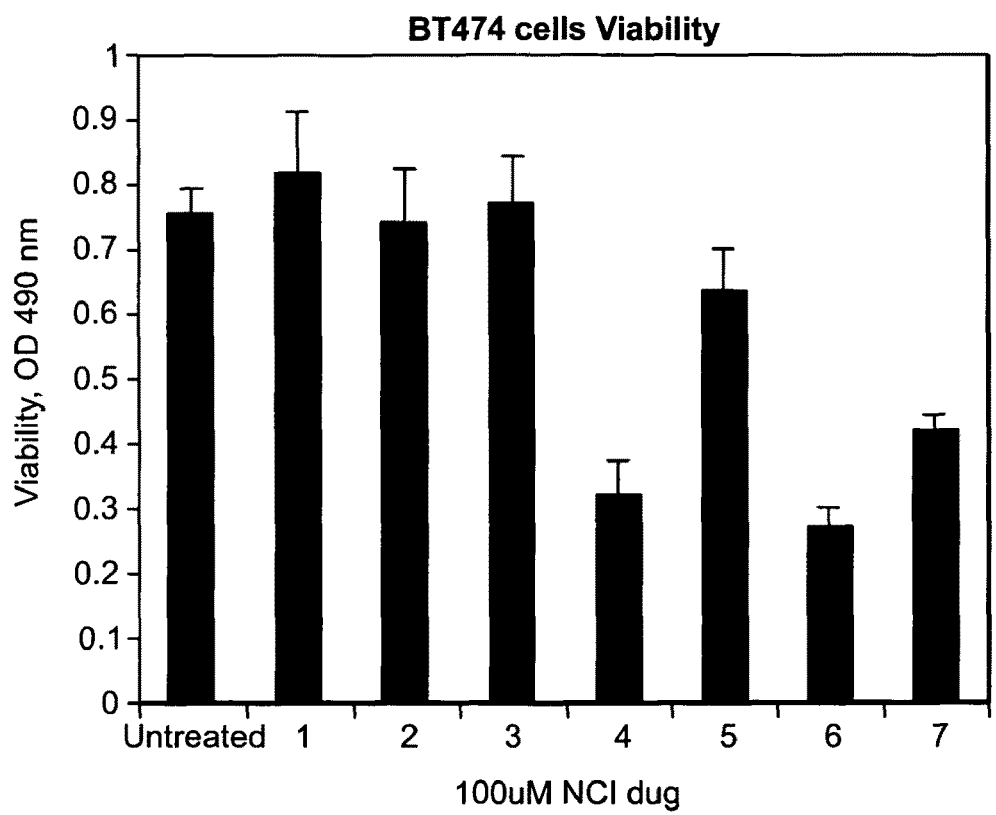
FIG. 16. depicts BT474 cell viability against D-compounds.
Figure 17:
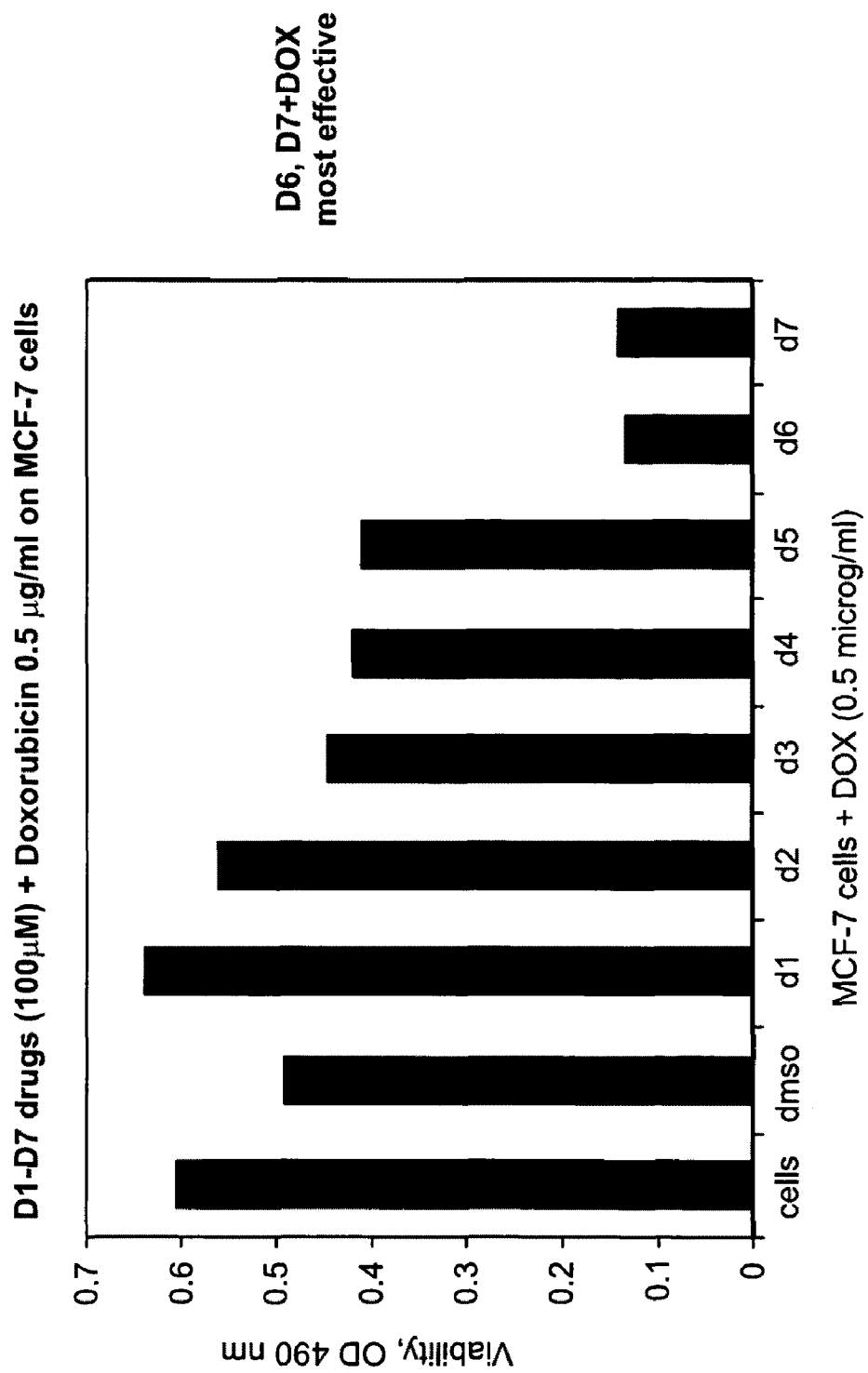
FIG. 17. depicts MCF-7 cell viability against D-compounds with doxorubicin.
Figure 18A:
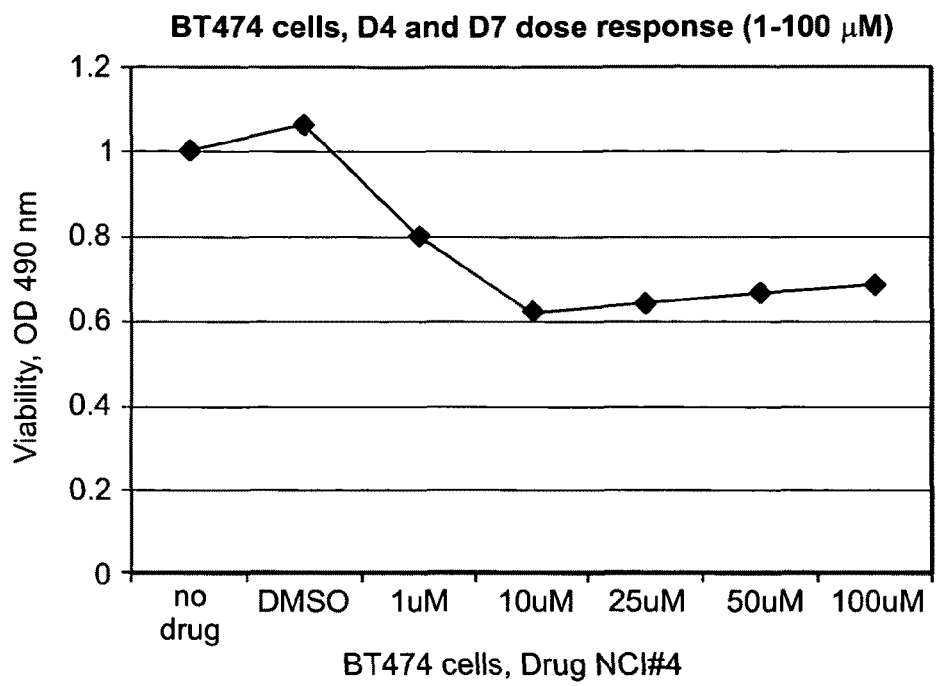
FIG. 18 depicts BT474 cell viability against doses of compounds D4 (A) and D7 (B).
Figure 18B:
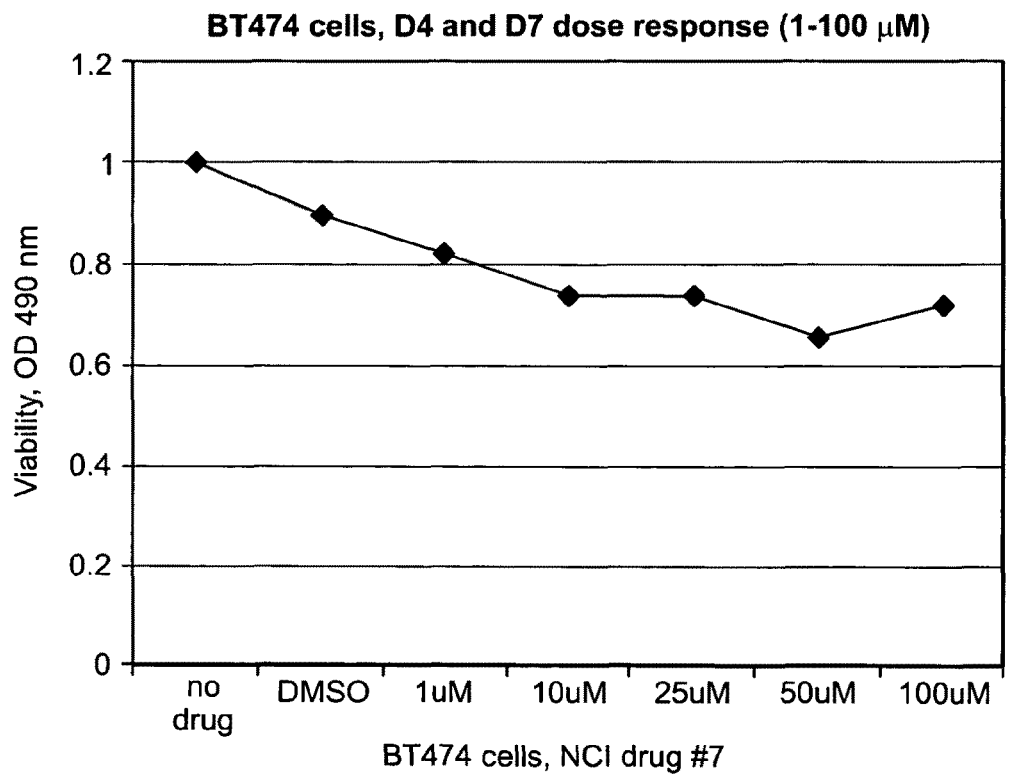

The present inventors have now discovered a therapeutic strategy that addresses inhibition of FAK by targeting FAK protein-protein binding interactions with FAK binding partners. Such interactions are relevant for modulation of apoptosis and cell proliferation, particularly in certain cancer types where FAK mechanisms play a significant role.

The present invention relates, at least in part, to the discovery that the FAK protein-protein interactions are useful as targets (e.g., selective) for tumor therapy. Phage display analyses reveal potential FAK binding partners. Disruption of these binding interactions cause loss of viability and apoptosis in cancer but not in normal cells in vitro.

1. DEFINITIONS

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a cell proliferative disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "cell proliferative disorder" includes disorders involving the undesired or uncontrolled proliferation of a cell. Examples of such disorders include, but are not limited to, tumors or cancers (e.g., lung (small cell and non-small cell), thyroid, prostate, pancreatic, breast or colon), sarcoma or melanoma.

The language "a FAK protein-protein binding partner" refers to a protein (including those delineated herein) that bind with FAK (e.g., full length, N-terminus, C-terminus, carboxy terminus, kinase domain, FERM domain, FAT domain).

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, halo$C_1$-$C_8$alkyl, halo$C_1$-$C_8$alkoxy, $C_1$-$C_8$alkanoyl, C2-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result.

The term "obtaining" as in "obtaining a compound capable of modulating FAK or FAK protein-protein interaction partner binding" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a cell proliferative disorder.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a cell proliferative disorder or who could otherwise benefit from the administration of a compound of the invention of the invention, such as human and non-human animals. Preferred humans include human patients suffering from or prone to suffering from a cell proliferative disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to a cell proliferative disorder" is meant to include subjects at risk of developing disorder of cell proliferation, e.g., cancer, i.e., subjects suffering from viral infection with cancer viruses, subjects that have been exposed to ionizing radiation or carcinogenic compounds, subjects having a family or medical history of cancer, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention of the invention refers to an amount of an agent which is effective, upon single or multiple dose administration to the patient, in inhibiting cell proliferation and/or symptoms of a cell proliferative disorder, or in prolonging the survivability of the patient with such a cell proliferative disorder beyond that expected in the absence of such treatment.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. COMPOUNDS OF THE INVENTION

In one aspect, the invention provides compounds capable of modulating (e.g., inhibiting or stimulating) (directly or indirectly) FAK binding activity. In another aspect is a combination of a compound capable of modulating (e.g., inhibiting or stimulating) (directly or indirectly) FAK binding activity and an additional therapeutic agent, e.g., a chemotherapeutic agent.

In one embodiment, the invention provides a compound capable of modulating FAK protein-protein binding; and pharmaceutically acceptable esters, salts, and prodrugs thereof.

Certain preferred compounds include compounds specifically delineated herein:

Inhibitor:

C1: 2-[2-(anilinocarbamoyl)phenyl]benzoic acid;

C2: N'-[(4-chlorophenyl)methyl]-N,N-dimethyl-N'-pyridin-2-yl-ethane-1,2-diamine;

C3: pyridin-2-ylmethanamine;

C4: N'-[(4-chlorophenyl)methyl]-N,N-dimethyl-N'-pyridin-2-yl-ethane-1,2-diamine (NSC 409949; Sigma C1915, Suprastin; chloropyramine hydrochloride);
C5: 1-(3-fluorophenyl)-3-naphthalen-2-yl-urea (NSC 216201);
C6: N-[4-[(3-fluorophenyl)carbamoylamino]phenyl]acetamide;
C7: N-[4-[(4-fluorophenyl)carbamoylamino]phenyl]acetamide;
C8: N-[(6-nitrobenzo[1,3]dioxol-5-yl)methylideneamino]benzamide;
C10: 0-(4-chlorophenyl)-3-methyl-7-(5-methylpyridin-2-yl)-8-oxa-1,7,9-triazabicyclo[4.4.0]deca-2,4,9-triene;
C11: 2-(1,7-diazabicyclo[4.3.0]nona-2,4,6,8-tetraen-8-yl)acetic acid;
C12: 2-(4-methyl-1,7-diazabicyclo[4.3.0]nona-2,4,6,8-tetraen-8-yl)acetic acid;
C27: usinic acid derivative 4,4a-dihydro-4A(phenylthio), racemate (NSC250435);
N2: 2-chloro-10-[3-(4-methylpiperazin-1-yl)propyl]phenothiazine;
N9: 4,6-diphenyl-1,3,5-thiadiazinane-2-thione;
N14: (9,9-dimethylacridin-10-yl)-(2-dimethylaminoethylsulfanyl)methanone; methanesulfonic acid;
N16: 3-(4-chlorophenyl)-4-hydroxy-naphthalene-1,2-dione;
N1: N-pyridin-4-ylpyridin-4-amine;
N7: 2-(1H-benzoimidazol-2-ylmethyl)-1H-benzoimidazole;
N8: 7-oxa-2,10-diazabicyclo[4.4.0]deca-2,4,11-trien-9-one;
N11: 1-(3-Thienylmethyl)-1.lambda.~5~,3,5,7-tetraazatricyclo[3.3.1.1~3,7~]decane;
N15: N-(pyridin-4-ylmethylideneamino)-4,5-dihydro-1H-imidazol-2-amine;

```
peptide-35 (WHWQWTPWSIQP);    (SEQ ID NO: 1)

peptide-AV3 (WHWRPWTPCKMF)    (SEQ ID NO: 2)
```

Stimulator:
C9: N-[1-(4-chlorophenyl)propyl]-N-ethyl-pyridin-2-amine;
P2: 1-benzyl-15,3,5,7-tetraazatricyclo [3.3.1.1~3,7~]decane;
P4: 1-(4-chlorophenyl)-2-(15,3,5,7-tetraazatricyclo[3.3.1.1~3,7~]dec-1-yl)ethanone;
P7: 1-(4-methoxyphenyl)-2-(15,3,5,7-tetraazatricyclo[3.3.1.1~3,7~]dec-1-yl)ethanone;
P8: 1-(4-iodophenyl)-2-(15,3,5,7-tetraazatricyclo[3.3.1.1~3,7~]dec-1-yl)ethanone oxime;
P10: 1-(2-naphthyl)-2-(15,3,5,7-tetraazatricyclo[3.3.1.1~3,7~]dec-1-yl)ethanone
D4: methyl N-[5-(cyclopropanecarbonyl)-3H-benzoimidazol-2-yl]carbamate;
D5: (4,6-Dimethyl-pyrimidin-2-yl)-(5-nitro-1H-benzoimidazol-2-yl)-amine;
D6: 1-(2-chloro-4-methoxy-phenyl)-3-(5-chloro-2-methoxy-phenyl) urea;

The invention also relates to the pharmaceutically acceptable salts and esters of the above-mentioned compounds.

In one aspect, the "P" compounds (e.g., P2, P4, P7, P8, P10) target (e.g., bind, modulate) the human p53, and more particularly, the binding sites delineated herein (e.g., an amino acid sequence that comprises amino acids 65-71 of human p53; an amino acid sequence that comprises QMSGAPH (SEQ ID NO: 3)). In one aspect, the "D" compounds (e.g., D4, D5, D6) target (e.g., bind, modulate) the binding region (e.g., groove) on FAK involved with interaction with p53.

In one aspect, the "C" compounds (e.g., C1, C2, C3, C4, C5, C6, C7, C8, C10, C11, C12, C27) target (e.g., bind, modulate) the FAK-VEGFR3 binding site on the focal adhesion targeting (FAT) domain of the FAK C-terminus.

In one aspect, the "N" compounds (e.g., N2, N9, N14, N16, N1, N7, N8, N11, N15)) target (e.g., bind, modulate) the FAK-RIP binding site.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

According to another embodiment, the invention provides compounds which associate with or bind to a FAK binding pocket or a FAK protein-protein binding partner binding pocket (including binding sites where FAK binds with the partner or other binding sites in the partner) produced or identified by the methods described herein.

In another aspect, the invention provides polypeptides useful for screening for compounds useful for treatment of proliferative disorders. Such polypeptides include for example FAK, domains of FAK, domains of FAK binding partners. Such polypeptides can be a fusion protein, e.g., a binding pocket moiety fused with a detectable reporter moiety such as green fluorescent protein, or labeled with a detectable tag such as a fluorescent label, a radiolabel, and the like. Such a fusion protein can be used in screening for compounds capable of modulating FAK or a FAK protein-protein binding partner.

3. USES OF THE COMPOUNDS OF THE INVENTION

The compounds delineated herein are useful in methods for modulating FAK-mediated disease and disorders and symptoms thereof. FAK is also associated with conditions such as cancer, obesity and hypertension, ischemia-reperfusion injury, inflammation, rheumatoid arthritis, and cataracts. It is theorized that reducing or increasing FAK level and modulating its activity will benefit patients suffering from these conditions.

FAK modulation technology can be the basis of therapies aimed at a number of unmet disease targets. Certain compounds are identified as FAK binding compounds useful for addressing disease (e.g., cancer). Additionally, a small molecule FAK agonist/promoter is idnetified that could be useful in upregulating FAK. This agonist/promoter has the potential to reduce collateral damage caused by transient interruption of blood supply. FAK also appears to be involved in cirrhosis, obesity and hypertension, inflammation, rheumatoid arthritis, and cataracts.

In one embodiment, the invention provides a method of treating a FAK-mediated disease or disorder in a subject comprising administering to the subject identified as in need thereof a compound capable of inhibiting the binding interaction of focal adhesion kinase (FAK) with a second protein. In aspects, the disease or disorder is obesity, hypertension, ischemia-reperfusion injury, inflammation, rheumatoid arthritis, or cataracts. In other aspects, the disease or disorder is ovarian cancer. In other aspects, the compound is any compound delineated herein.

In one embodiment, the invention provides methods for treating a subject for a cell proliferative disorder, by administering to the subject an effective amount of a compound capable of disrupting FAK binding with a FAK protein-protein binding partner. A cell proliferative disorder includes cancer (e.g., wherein the cancer is breast, colon, pancreatic, thyroid, lung, or melanoma). In certain embodiments, the subject is a mammal, e.g., a primate, e.g., a human.

In this embodiment, the compounds of the invention may either directly or indirectly modulate the activity of FAK, FAK binding partner, or specific domains thereof. A cell undergoing uncontrolled proliferation can be contacted with a compound of the invention to inhibit cell proliferation or induce apoptosis. Contacting cells or administering the compounds of the invention to a subject is one method of treating a cell or a subject suffering from or susceptible to unwanted or undesired cell proliferation or a cell proliferative disorder.

In one embodiment, a method of treating a subject suffering from or susceptible to unwanted or undesired cell proliferation or a cell proliferative disorder includes administering to a subject in need thereof a therapeutically effective amount of a compound capable of directly or indirectly modulate the activity of FAK, FAK binding partner, or specific domains thereof, to thereby treat the subject suffering from or susceptible to unwanted or undesired cell proliferation or a cell proliferative disorder. Exemplary compounds include compounds described herein.

Thus, in one embodiment, the invention provides methods for treating a subject for a cell proliferative disorder, by administering to the subject an effective amount of a compound capable of binding to a binding pocket of FAK or a FAK binding partner.

In other aspects, the cell proliferative disorder is cancer of the breast, colon, pancreatic, thyroid, lung, or melanoma. In other aspects, the cell proliferative disorder is ovarian. In other aspects, the cell proliferative disorder is cancer of the blood, brain, leukemia, chronic lymphocytic leukemia, chronic myeloid leukemia, colorectal, gastrointestinal stromal tumor, kidney, lymphoma, or multiple myeloma.

In certain embodiments, the methods of the invention include administering to a subject a therapeutically effective amount of a compound of the invention in combination with another pharmaceutically active compound. Examples of pharmaceutically active compounds include compounds known to treat cell proliferative disorders, e.g., anticancer agent, antiproliferative agent, chemotherapeutic. Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In certain embodiments, the compound of the invention can be used in combination therapy with conventional cancer chemotherapeutics. Conventional treatment regimens for leukemia and for other tumors include radiation, drugs, or a combination of both. In addition to radiation, the following drugs, usually in combinations with each other, are often used to treat acute leukemias: vincristine, prednisone, methotrexate, mercaptopurine, cyclophosphamide, and cytarabine. Other examples include, for example, doxorubicin, cisplatin, taxol, 5-fluorouracil, etoposid, etc., which demonstrate advantages (e.g., chemosensitization of cells) in combination with the compounds described herein. In chronic leukemia, for example, busulfan, melphalan, and chlorambucil can be used in combination. Most conventional anti-cancer drugs are highly toxic and tend to make patients quite ill while undergoing treatment. Vigorous therapy is based on the premise that unless every cancerous cell is destroyed, the residual cells will multiply and cause a relapse. The compounds of the invention can also administered in combination with chemotherapy agents such as doxorubicin or gemcitabine. In particular, the compound C4 is useful in combination with doxorubicin or gemcitabine, or combinations thereof.

In certain aspects, the compounds delineated herein can be used in combination with the following chemotherapy agents (or combinations thereof) for treating breast cancer: Anthracyclines: including doxorubicin (Adriamycin), epirubicin (Ellence), and liposomal doxorubicin (Doxil); Taxanes: including docetaxel (Taxotere), paclitaxel (Taxol), and protein-bound paclitaxel (Abraxane); Cyclophosphamide (Cytoxan); Capecitabine (Xeloda) and 5 fluorouracil (5 FU); Vinorelbine (Navelbine); Gemcitabine (Gemzar); Trastuzumab (Herceptin).

In aspects, the compounds delineated herein can be used in combination with the following chemotherapy agent combinations for treating breast cancer:
  CMF: cyclophosphamide (Cytoxan), methotrexate (Amethopterin, Mexate, Folex), and 5-fluorouracil (Fluorouracil, 5-FU, Adrucil);
  CAF (FAC): cyclophosphamide, doxorubicin (Adriamycin), and 5-fluorouracil;
  AC: doxorubicin (Adriamycin) and cyclophosphamide;
  EC: epirubicin (Ellence) and cyclophosphamide;
  TAC: docetaxel (Taxotere), doxorubicin (Adriamycin), and cyclophosphamide;
  AC→T: doxorubicin (Adriamycin) and cyclophosphamide followed by paclitaxel (Taxol) or docetaxel (Taxotere);
  A→CMF: doxorubicin (Adriamycin), followed by CMF;
  A CEF (FEC): cyclophosphamide, epirubicin, and 5-fluorouracil (with or without docetaxel);
  TC: docetaxel (Taxotere) and cyclophosphamide; or
  GT: gemcitabine (Gemzar) and paclitaxel (Taxol).

In aspects, the compounds delineated herein can be used in combination with the following chemotherapy agents (or combinations thereof) for treating breast cancer: carboplatin (Paraplatin), cisplatin (Platinol), vinorelbine (Navelbine), capecitabine (Xeloda), pegylated liposomal doxorubicin (Doxil), and albumin-bound paclitaxel (Abraxane).

In certain aspects, the compounds delineated herein can be used in combination with the following chemotherapy agents (or combinations thereof) for treating pancreatic cancer: Gemcitabine (Gemzar); Fluorouracil (5-FU); Capecitabine (Xeloda); bevacizumab, vatalanib, cetuximab, and erlotinib.

In certain aspects, the compounds delineated herein can be used in combination with the following chemotherapy agents (or combinations thereof) for treating lung cancer: carboplatin, cisplatin, docetaxel, etoposide, gemcitabine, irinotecan, paclitaxel, vinorelbine, pemetrexed, erlotinib, topotecan, bevacizumab; or combinations of bevacizumab and carboplatin or paclitaxel.

In certain aspects, the compounds delineated herein can be used in combination with the following chemotherapy agents (or combinations thereof) for treating ovarian cancer: combination of paclitaxel (Taxol) and carboplatin or cisplatin.

In certain aspects, the compounds delineated herein can be used in combination with the following chemotherapy agents (or combinations thereof) for treating colon cancer: AIO regimen (folic acid, fluorouracil [5-FU], and irinotecan); LV5FU2 regimen (leucovorin and 5-FU); FOLFOX4 regimen (oxaliplatin, leucovorin, and 5-FU); FOLFOX6 regimen (oxaliplatin, leucovorin, and 5-FU); FOLFIR1 regimen (folic acid, 5-FU, and irinotecan); or Saltz regimen (irinotecan, 5-FU, and leucovorin); Levamisole regimen (5-FU and levamisole); Mayo Clinic or NCCTG regimen (5-FU and low-dose leucovorin); Roswell Park or NSABP regimen (5-FU and high-dose leucovorin).

In certain aspects, the compounds delineated herein can be used in combination with the following chemotherapy agents (or combinations thereof) for treating the various cancers listed below:

| Cancer Type | Oral Chemotherapy |
|---|---|
| Blood cancers | cyclophosphamide |
| Breast cancer | capecitabine, cyclophosphamide, methotrexate |
| Brain tumors | temozolomide |
| Leukemias | methotrexate |
| Chronic lymphocytic leukemia | chlorambucil |
| Chronic myeloid leukemia | imatinib* |
| Colorectal cancer | capecitabine, methotrexate |
| Gastrointestinal stromal tumor | sunitinib*, imatinib* |
| Kidney cancer | sorafenib*, sunitinib* |
| Lung cancer | erlotinib*, gefitinib*, methotrexate, etoposide |
| Lymphomas | chlorambucil |
| Multiple myeloma | melphalan |
| Ovarian cancer | cyclophosphamide, melphalan |

*Non-chemotherapy targeted therapies

Determination of a therapeutically effective anti-proliferative amount or a prophylactically effective anti-proliferative amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of cell proliferative disorders in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

The identification of those patients who are in need of prophylactic treatment for cell proliferative disorders is well within the ability and knowledge of one skilled in the art. Certain of the methods for identification of patients which are at risk of developing cell proliferative disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a cell proliferative disorder by methods well known in the art (e.g., determining tumor size or screening for tumor markers where the cell proliferative disorder is cancer) and then administering a therapeutically effective amount of an inhibitor of cell proliferation (e.g., those described herein) according to the invention to the subject. After an appropriate period of time after the administration of the compound (e.g., 1 day, 1 week, 2 weeks, one month, six months), the extent of the cell proliferative disorder is determined again. The modulation (e.g., decrease) of the extent or invasiveness of the cell proliferative disorder indicates efficacy of the treatment. The extent or invasiveness of the cell proliferative disorder may be determined periodically throughout treatment. For example, the extent or invasiveness of the cell proliferative disorder may be checked every few hours, days or weeks to assess the further efficacy of the treatment. A decrease in extent or invasiveness of the cell proliferative disorder indicates that the treatment is efficacious. The method described may be used to screen or select patients that may benefit from treatment with an inhibitor of a cell proliferative disorder.

As used herein, "obtaining a biological sample from a subject," includes obtaining a sample for use in the methods described herein. A biological sample is described above.

Yet another aspect presents a method to identify a compound that modulates the interaction of FAK, FAK binding partner, or specific domains thereof. The method may include obtaining the crystal structure of FAK, FAK binding partner, or specific domains thereof (optionally apo form or complexed) or obtaining the information relating to the crystal structure of a FAK, FAK binding partner, or specific domains thereof (optionally apo form or complexed), in the presence and/or absence of the test compound. Compounds may then be computer modeled into or on the FAK, FAK binding partner, or specific domains thereof binding site of the crystal structure to predict stabilization of the interaction between the FAK, FAK binding partner, or specific domains thereof and the test compound. Once potential modulating compounds are identified, the compounds may be screened using cellular assays, such as the ones identified herein and competition assays known in the art. Compounds identified in this manner are useful as therapeutic agents.

In another aspect, a compound of the invention is packaged in a therapeutically effective amount with a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In another aspect, the invention provides methods for inhibiting cell proliferation. In one embodiment, a method of inhibiting cell proliferation (or a cell proliferative disorder) according to the invention includes contacting cells with a compound capable of modulating FAK, FAK binding partner, or specific domains thereof. In either embodiment, the contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a cell proliferative disorder in a subject include administering an effective amount of a compound of the invention (i.e., a compound described herein) to the subject. The administration may be by any route of administering known in the pharmaceutical arts. The subject may have a cell proliferative disorder, may be at risk of developing a cell proliferative disorder, or may need prophylactic treatment prior to anticipated or unanticipated exposure to a conditions capable of increasing susceptibility to a cell proliferative disorder, e.g., exposure to carcinogens or to ionizing radiation.

In one aspect, a method of monitoring the progress of a subject being treated with a compound herein includes determining the pre-treatment status (e.g., size, growth rate, or invasiveness of a tumor) of the cell proliferative disorder, administering a therapeutically effective amount of a compound herein to the subject, and determining the status (e.g., size, growth rate, or invasiveness of a tumor) of the cell proliferative disorder after an initial period of treatment with the compound, wherein the modulation of the status indicates efficacy of the treatment.

The subject may be at risk of a cell proliferative disorder, may be exhibiting symptoms of a cell proliferative disorder, may be susceptible to a cell proliferative disorder and/or may have been diagnosed with a cell proliferative disorder.

If the modulation of the status indicates that the subject may have a favorable clinical response to the treatment, the subject may be treated with the compound. For example, the subject can be administered therapeutically effective dose or doses of the compound.

In another aspect, methods for evaluating a test compound comprise contacting a FAK, FAK binding partner, or specific domains thereof with a test compound (complex), and evaluating the binding interaction following contact, wherein a change in the stability of the complex relative to a reference value is an indication that the test compound modulates the stability of the complex.

The FAK, FAK binding partner, or specific domains thereof complex may be modeled in silico, or may be a complex within a cell, isolated from a cell, recombinantly expressed, purified or isolated from a cell or recombinant expression system or partially purified or isolated from a cell or recombinant expression system.

Kits of the invention include kits for treating a cell proliferative disorder in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of an treatment for a cell proliferative disorder may be packaged with a kit for monitoring the progress of a subject being treated for a cell proliferative disorder according to the invention.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like.

The present method can be performed on cells in culture, e.g. in vitro or ex vivo, or on cells present in an animal subject, e.g., in vivo. Compound of the invention can be initially tested in vitro using cells from the respiratory tract from embryonic rodent pups (See e.g. U.S. Pat. No. 5,179,109—fetal rat tissue culture), or other mammalian (See e.g. U.S. Pat. No. 5,089,517—fetal mouse tissue culture) or non-mammalian animal models.

Alternatively, the effects of compound of the invention can be characterized in vivo using animals models.

4. PHARMACEUTICAL COMPOSITIONS

The invention also provides a pharmaceutical composition, comprising an effective amount of a compound of the and a pharmaceutically acceptable carrier. In a further embodiment, the effective amount is effective to treat a cell proliferative disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and performing agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form.

Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

6. SCREENING METHODS AND SYSTEMS

In another aspect, the invention provides a machine readable storage medium which comprises the structural coordinates of either one or both of the binding pockets identified herein, or similarly shaped, homologous binding pockets. Such storage medium encoded with these data are capable of displaying a three-dimensional graphical representation of a molecule or molecular complex which comprises such binding pockets on a computer screen or similar viewing device.

The invention also provides methods for designing, evaluating and identifying compounds which bind to the aforementioned binding pockets. Thus, the computer produces a three-dimensional graphical structure of a molecule or a molecular complex which comprises a binding pocket.

In another embodiment, the invention provides a computer for producing a three-dimensional representation of a molecule or molecular complex defined by structure coordinates of FAK, FAK binding partners or domains thereof, or a three-dimensional representation of a homologue of said molecule or molecular complex, wherein said homologue comprises a binding pocket that has a root mean square deviation from the backbone atoms of said amino acids of not more than 2.0 (more preferably not more than 1.5) angstroms In exemplary embodiments, the computer or computer system can include components which are conventional in the art, e.g., as disclosed in U.S. Pat. Nos. 5,978,740 and/or 6,183,121 (incorporated herein by reference). For example, a computer system can includes a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as has well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising a binding pocket may be used for a variety of purposes, such as drug discovery.

For example, the structure encoded by the data may be computationally evaluated for its ability to associate with chemical entities. Chemical entities that associate with a binding pocket of a FAK, FAK binding partner, or specific domains thereof, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding pocket of FAK, FAK binding partner, or specific domains thereof, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:

i) employing computational means to perform a fitting operation between the chemical entity and a binding pocket of the molecule or molecular complex; and ii) analyzing the results of the fitting operation to quantify the association between the chemical entity and the binding pocket. The term "chemical entity", as used herein, refers to chemical compounds, complexes of at least two chemical compounds, and fragments of such compounds or complexes.

The design of compounds that bind to or inhibit FAK, FAK binding partner, or specific domains thereof binding pockets according to this invention generally involves consideration of several factors. First, the entity must be capable of physically and structurally associating with parts or all of the FAK, FAK binding partner, or specific domains thereof-related binding pockets. Non-covalent molecular interactions important in this association include hydrogen bonding, van der Waals interactions, hydrophobic interactions and electrostatic interactions. Second, the entity must be able to assume a conformation that allows it to associate with the FAK, FAK binding partner, or specific domains thereof-related binding pocket(s) directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the binding pocket or homologues thereof.

The potential inhibitory or binding effect of a chemical entity on a FAK, FAK binding partner, or specific domains thereof-related binding pocket may be analyzed prior to its actual synthesis and testing by the use of computer modeling techniques. If the theoretical structure of the given entity suggests insufficient interaction and association between it and the target binding pocket, testing of the entity is obviated. However, if computer modeling indicates a strong interaction, the molecule may then be synthesized and tested for its ability to bind to a binding pocket. This may be achieved, e.g., by testing the ability of the molecule to inhibit FAK, FAK binding partner, or specific domains thereof activity, e.g., using assays described herein or known in the art. In this manner, synthesis of inoperative compounds may be avoided.

A potential inhibitor of a FAK, FAK binding partner, or specific domains thereof-related binding pocket may be computationally evaluated by means of a series of steps in which chemical entities or fragments are screened and selected for their ability to associate with the FAK, FAK binding partner, or specific domains thereof-related binding pockets.

One skilled in the art may use one of several methods to screen chemical entities or fragments for their ability to associate with a FAK, FAK binding partner, or specific domains thereof-related binding pocket. This process may begin by visual inspection of, for example, a FAK, FAK binding partner, or specific domains thereof-related binding pocket on the computer screen based on the FAK, FAK binding partner, or specific domains thereof structure coordinates described herein, or other coordinates which define a similar shape generated from the machine-readable storage medium. Selected fragments or chemical entities may then be positioned in a variety of orientations, or docked, within that binding pocket as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding pocket.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention [see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)].

Once a compound has been designed or selected, the efficiency with which that entity may bind to a binding pocket may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silico screening of virtual libraries of compounds, e.g., as described herein. Many thousands of compounds can be rapidly screened and the best virtual compounds can be selected for further screening (e.g., by synthesis and in vitro testing). Small molecule databases can be screened for chemical entities or compounds that can bind, in whole or in part, to a FAK, FAK binding partner, or specific domains thereof binding pocket. In this screening, the quality of fit of such entities to the binding site may be judged either by shape complementarity or by estimated interaction energy.

In one aspect, the methods delineated herein can further comprise procuring and testing the test compound in in vivo or in vitro assays. The relevant assays are known in the art and include those known for evaluation of FAK and FAK binding interactions and those delineated herein.

In one aspect, the computer or storage medium delineated herein includes the structure coordinates of FAK bound to a FAK-binding compound (e.g., a FAK/C4 complex; the coordinates of Table 2).

In another aspect, the methods of designing, evaluating or identifying compounds that bind to binding pockets delineated herein include the structure coordinates of FAK bound to a FAK-binding compound (e.g., a FAK/C4 complex; the coordinates of Table 2).

EXAMPLES

The invention is further illustrated by the following examples which are intended to illustrate but not limit the scope of the invention.

Example 1

Database of Small Molecules

The NCI/DTP maintains a repository of approximately 240,000 samples (i.e., the plated compound set) which are non-proprietary and offered to the research community for discovery and development of new agents for the treatment of cancer, AIDS, or opportunistic infections afflicting subjects with cancer or AIDS. The three-dimensional coordinates for the NCI/DTP plated compound set is obtained in the MDL SD format (http://www.chm.tu-dresden.de/edv/vamp65/REFERS/vr_03d.htm) and converted to the mol2 format by the DOCK utility program SDF2MOL2. Partial atomic charges, solvation energies and van der Waals parameters for the ligands are calculated using SYBDB and added to the plated compound set mol2 files.

Example 2

Database Screening To Identify Potential Small Molecule Inhibitors of FAK. In lieu of conducting high-throughput screening, a more rapid and economical structure-based approach combining molecular docking in silico with functional testing is used. A large chemical library of compounds with known three-dimensional structure is positioned in the structural pocket selected by SPHGEN (UCSF) on the crystal structure of human FAK (PDB code 1K05). This approach combines resources available through the NCI/DTP (atomic coordinates and small molecules) with improved molecular docking and scoring algorithms imposed in DOCK5.1 (UCSF). 20,000 small molecule compounds with drug-like characteristics (following the Lipinski rules) were docked into the FAT domain of the human FAK crystal structure in 100 different orientations using DOCK5.1. As an example, one such DOCKED ligand, representing the highest scoring compound, 2-[2-(anilinocarbamoyl)phenyl]benzoic acid, is shown (left). In this case, the small molecule is positioned in a region that is in close proximity to the LD paxillin binding epitope. The predicted binding energies of interaction between each compound and the human FAK FAT domain are estimated, with the top scoring compound given a DOCK score of −17.7 kcal per mol. The 20 compounds with the highest scores are requested for functional testing from the NCI/DTP.

The National Cancer Institute/Developmental Therapeutics Program (NCI/DTP) maintains a repository of approximately 220,000 samples (the plated compound set) that are nonproprietary and offered to the extramural research community free of charge. The three-dimensional coordinates for the NCI/DTP plated compound set was obtained in the MDL SD format and converted to the mol2 format by the DOCK utility program SDF2MOL2. Partial atomic charges, solvation energies, and van der Waals parameters for the ligands were calculated using SYBDB and added to the plated compound set mol2 file.

In Silico Molecular Docking of Potential FAK-CD Small Molecule Inhibitors. All docking calculations are performed with the DOCK, v5.1.0. The general features of DOCK include rigid orienting of ligands to receptor spheres, AMBER energy scoring, GB/SA solvation scoring, contact scoring, internal nonbonded energy scoring, ligand flexibility, and both rigid and torsional simplex minimization. Unlike previously distributed versions, this release incorporates automated matching, internal energy (used in flexible docking), scoring function hierarchy, and new minimizer termination criteria. The coordinates for the molecular model of the human FAK FAT domain are used in the molecular docking calculations. To prepare the site for docking, all water molecules are removed. Protonation of receptor residues is performed with Sybyl (Tripos, St. Louis, Mo.). The structure is explored using sets of spheres to describe potential binding pockets. The number of orientations per molecule is 100. Intermolecular AMBER energy scoring (vdw+columbic), contact scoring, and bump filtering are implemented in DOCK5.1.0. SETOR and GRASP are used to generate molecular graphic images.

As shown herein, these compounds have antiproliferative activity; without wishing to be bound by theory, it is believed that.

Example 3

Cell-based assays. Selected small molecules are evaluated in cell-based proliferation and apoptosis assays in model system of BT474 and MCF7 breast cancer cells and normal MCF10 cells. Other cells lines relevant for study are MiaPaCa-2 and PANC-1 (pancreatic cancer), A375 (melanoma), A549 (lung cancer), HT29 and COLO5 (colon cancer), SAOS (osteosarcoma), HCT116 p53(−/−) and HCT116 p53(+/+) (colon cancer) and C8186 (melanoma). The multiplex approach to analyze more than one parameter from the same culture well is used.

CellTiter 96 Aqueous One Solution Cell Proliferation Assay (Promega). The assay is performed by adding a small amount of the One Solution Reagent directly to culture wells, incubating for 1-4 hours and then recording absorbance at 490 nm with a spectrophotometric plate reader. The quantity of formazan product as measured by the amount of 490 nm absorbance is directly proportional to the number of living cells in culture;

The CellTiter-Blue Cell Viability Assay (Promega). Cell-Titer-Blue Reagent is added directly to each well (20µ reagent to each 100µ of medium in 96-well format), the plates are incubated at 37° C., and the fluorescent signal is measured ($560_{Ex}/590_{Em}$). This test can be combined with additional assays. The caspase activity is measured in the same wells by adding 120µ of the Apo-ONE Homogeneous Caspace-3/7 Assay Reagent (Promega). Cells are incubated for an additional hour at ambient temperature prior to recording fluorescence ($485_{Ex}/527_{Em}$);

Measurement of FAK-specific effect. The readout of a FAK-specific effect of selected in silico small molecules is specific displacement of FAK from the focal adhesions of the tumor cells. Tumor cells are doubly stained with FAK and paxillin using dual color techniques and extensive biochemical analyses of effects on FAK signaling are performed, essentially as previously published. See, Garces, C. A., et al., *Vascular Endothelial Growth Factor Receptor-3 and Focal Adhesion Kinase Bind and Suppress Apoptosis in Breast Cancer Cells*. Cancer Res % R 10.1158/0008-5472.CAN-05-1661, 2006. 66(3): p. 1446-1454; Xu, L.-h., et al., *The focal adhesion kinase suppresses transformation-associated, anchorage-independent apoptosis in human breast cancer cells*. J. Biol. Chem., 2000. 275: p. 30597-30604; Kurenova, E., et al., *Focal Adhesion Kinase Suppresses Apoptosis by Binding to the Death Domain of Receptor-Interacting Protein*. Mol. Cell. Biol., 2004. 24(10): p. 4361-4371.

Example 4

In a recent independent study we performed phage display assay with the N-terminal fragment of FAK (1-423 a.a.) and identified peptides relevant for protein-protein partner binding. We performed site-directed mutagenesis and mutated those amino acids. We then performed pull-down assay with human full length of FAK and demonstrated that wild type p53 proteins were able to bind FAK, while mutants had significantly lower background level of binding with FAK. Thus, we narrowed the region of FAK binding to specific areas in p53 or detected binding site of this novel binding. We conjugated these peptides to TAT to penetrate inside the cells and demonstrate FAK-dependent effect on survival.

Example 5

With phage display approach we have identified peptides that bind to the carboxy-terminus of FAK and cause apoptosis in breast cancer cells. One of these peptides contained sequence homologous to the vascular endothelial growth factor receptor 3 (VEGFR-3) protein. Recently we have shown that VEGFR3 binds to FAK (Cancer Res. 2006; 66:3:1446-1454). We have shown that VEGFR-3 is overexpressed in human breast tumors and cancer cell lines. In addition to its involvement with cell survival, VEGFR-3 is a primary factor in lymphatic angiogenesis. For the first time, we have shown the physical association of FAK and VEGFR-3. The association between the N-terminus of VEGFR-3, containing the peptide identified by phage display, and the C-terminus of FAK was detected by in vitro and in vivo binding studies. We then coupled a 12 amino-acid VEGFR-3 peptide, AV3, to a TAT cellular penetration sequence and showed that AV3, not control scrambled peptide, caused specific displacement of FAK from the focal adhesions and affected co-localization of FAK and VEGFR-3. In addition, AV3 peptide decreased proliferation, caused cell detachment and apoptosis in breast cancer cell lines, but not in normal breast cells. Thus, the FAK-VEGFR-3 interaction may have a potential use to develop novel molecular therapeutics to target the signaling between FAK and VEGFR-3 in human tumors. In order to determine the binding site on FAK, the C-terminal focal adhesion targeting sequence of FAK (FAT domain) has been expressed at high levels in *E. coli* and purified to greater than 95% homogeneity. This purified fragment retains the ability to bind peptide in vitro. NMR chemical shift mapping studies have localized the binding epitope of peptides onto the FAT domain of FAK. These studies show that selected peptides bind FAT at a site in the same structural pocket as paxillin binds. In silico modeling shows that peptide binding sites defined by the chemical shifts are appropriate for small drug-like molecule binding. We have performed preliminary screening of a chemical library of 20,000 such compounds and identified a series of small molecules for inhibition of FAK function.

Example 6

We have also shown that FAK overexpression suppresses apoptosis, thus providing a survival signal to human cancer cells. FAK is involved in multiple protein-protein interactions, serving not only as tyrosine kinase but also as scaffolding protein and may affect survival signaling through such interactions. Furthermore, our data shows that that the amino-terminus of FAK (FAK-NT) can induce apoptosis in breast cancer cells and can bind to a death domain containing serine-threonine kinase, Receptor Interacting Protein, (RIP). We use phage display approach to find peptides that can affect FAK functions and cause apoptosis in cancer cells. We have selected more than 40 peptide sequences, bound to FAK-NT. And we found certain of them affecting FAK functions and affecting proliferation of cancer cells.

Example 7

Investigation of compound C4 in various assays indicates that Compound C4 specifically dephosphorylates FAK and VEGFR-3, and disrupts their interaction, which leads to decrease in their colocalization in the cells (confirmed by immunofluorescence confocal microscopy and by FRET analysis), delay in cell proliferation, blockage at G1/S cell cycle transition and finally to apoptosis of cancer cells. In vitro experiments have shown that C4 decreases viability of many different types of cancer cells, including breast, colon, pancreatic, melanoma, lung, osteosarcoma. Furthermore, these compounds sensitized the cancer cells to chemotherapy. It is found that combination of C4 with Doxorubicin and Gemcitabine has an improved effect on decrease of cells viability and indicates that in combination these drugs can work at significantly lower concentration. In vivo mice experiments, utilizing subcutaneous xenograft models of breast and pancreatic cancers in nude mice have demonstrated that C4 has strong anticancer effect and reduced tumor growth up to 75% in comparison with nontreated tumors at concentration 60 mg/kg (daily intraperitoneal injections). Combination of C4 with Gemcitabine has much stronger anticancer effect than each of the drugs separately and has prolonged cytostatic effect on tumor growth after treatment withdrawal. Because the selected compound C4 is known as antihistamine receptor 1 drug Suprastin, we compared the effect of Suprastin on tumor growth in vivo with effect of other antihistamine receptor 1 drug Benadryl and found no any anticancer properties of this selected control drug. This indicates that any antihistamine effect appears to be surprising and distinct and unrelated to the anticancer effects. See, FIGS. 3-14.

These results indicate that C4: (i) decreases viability of many types of cancer cells; (ii) causes apoptosis in pancreatic and breast cancer cells in vitro; (iii) reduces motility and invasiveness of cancer cells; sensitizes pancreatic cancer and breast cancer cells to chemotherapy treatment in vitro; (v) reduces tumor growth in vivo in mouse model of breast cancer and pancreatic cancer; (vi) in combination with gemcitabine has prolonged cytostatic effect on pancreatic tumor growth after treatment withdrawal; (vii) decreases tumor growth better than doxorubicin, conventional chemotherapy for breast cancer; and (viii) in combination with gemcitabine or doxorubicin for cancer treatment can decrease the need for treatment doses of both drugs.

Example 8

Certain D-compounds (e.g., D4, D5, D6, D7) were examined and found to cause de-phosphorylation of Y397 and D4 in particular causes PARP down-regulation. As such, these compounds are useful as therapeutic agents.

Example 9

C4 Co-Crystallized with FAK FAT-Domain

Figure 19:
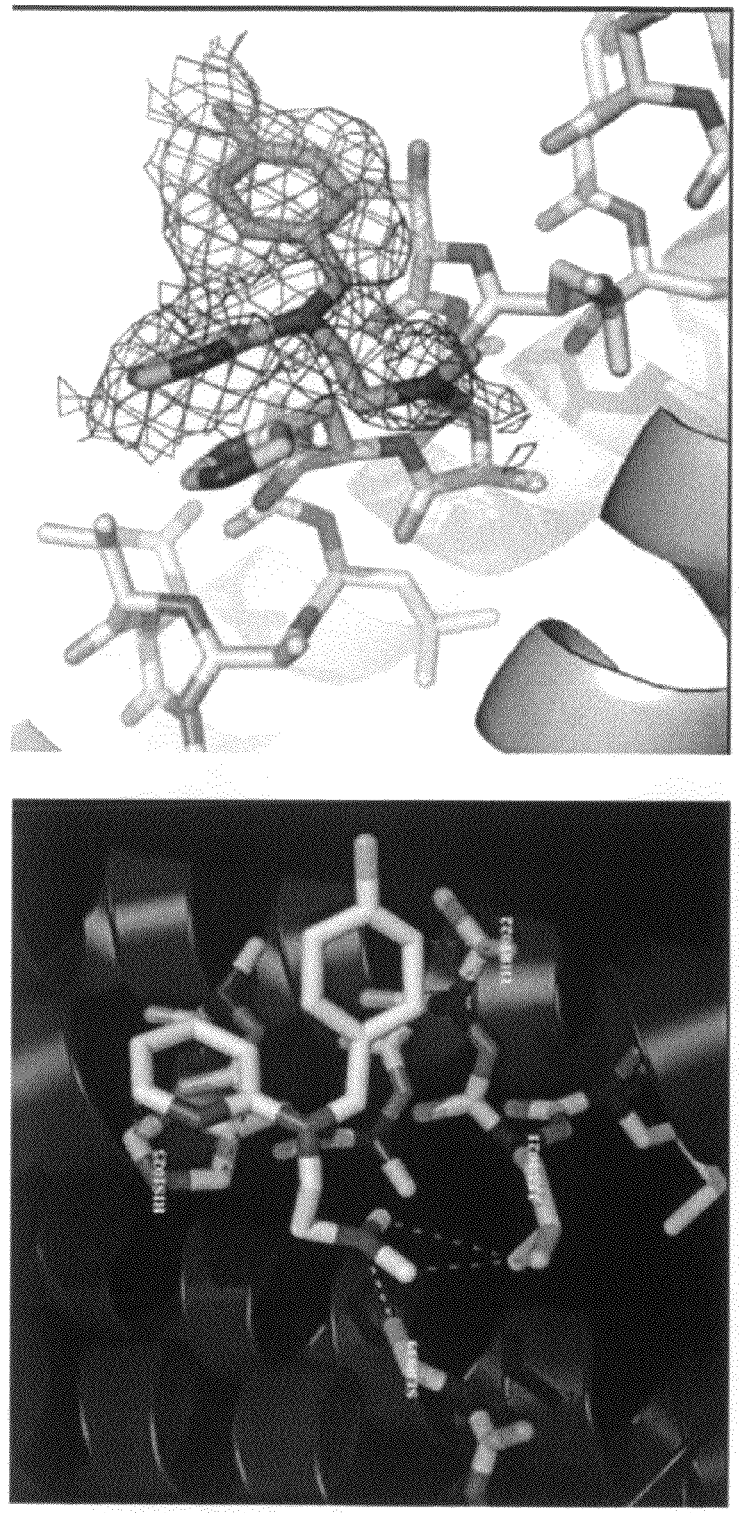
FIG. 19 depicts compound C4 co-crystallized with FAK FAT domain. Left: 2fo-fc electron density map at 1σ for C4 ligand bound to the Focal Adhesion Kinase FAT domain. Right: Calculated interactions between C4 and surrounding residues of FAK FAT domain.

To provide additional evidence for the mechanism of action of C4 and validate our computational docking methods, we undertook to co-crystallize this small molecule with the FAK FAT domain. The resulting data set diffracted to 1.99 Å and after refinement significant unaccounted-for density in the region of Histidine 1025 was revealed. FIG. 19 illustrates the binding mode of C4 with the Focal Adhesion Kinase FAT domain. A hydrogen bond is formed between the atom N3 of C4 and atom OG of serine 939. Hydrophobic interactions exist between C4 and residues S939, L1021, T1022, and H1025. A π-π interaction exists between the imidazole ring of H1025 and the C4 pyridine ring. Not shown in the image are two additional hydrogen bonds formed between C4 and a symmetry-related molecule within the crystal structure. These bonds exist between N1 and N2 of C4 and OD1 and OD2 of aspartic acid 1039. Thus we confirmed that selected small molecule C4 binds to FAK FAT domain and binding occurred in predicted by computer modeling site. See, FIG. 19. The C4 co-crystallized with FAK FAT domain. Left: 2fo-fc electron density map at 1σ for C4 ligand bound to the Focal Adhesion Kinase FAT domain. Right: Calculated interactions between C4 and surrounding residues of FAK FAT domain. Yellow line indicates hydrogen bond between Serine 939 hydroxyl group (donor) and C4 N3 (acceptor). Red lines indicate hydrophobic interactions between C4 and FAK calculated by LIGPLOT (Wallace et al). Note the π-stacking interaction between Histidine 1025 and C4 pyridine ring.

TABLE 1

| X-ray Data Collection and Refinement Statistics | |
|---|---|
| Data Collection | |
| Space group | P2₁2₁2₁ |
| Cell dimensions | a = 48.246, b = 50.289, c = 49.532, α = β = γ = 90 |
| Wavelength (Å) | 0.9322 |
| Resolution range (Å) | 30.0-1.99 (2.01-1.99) |
| Completeness (%) | 100.0 (100.0) |

TABLE 1-continued

| X-ray Data Collection and Refinement Statistics | |
|---|---|
| Average I/σ | 21.9 (3.5) |
| Unique Reflections | 8673 (213) |
| Redundancy | 5.9 (5.9) |
| Refinement | |
| Resolution range (Å) | 30.0-1.99 |
| Reflections used in refinement | 8625 |
| $R_{work}/R_{free}$ (%) | 24.2/24.9 |
| # FAT/Asymmetric Unit | 1 |
| Mean B-factor (Å²) | 25.86 |
| Ramachandran Plot Statistics | |
| Residues in most favored regions | 115 (99.1%) |
| Residues in additionally favored regions | 1 (0.9%) |
| Residues in generously allowed regions | 0 (0.0%) |
| Residues in disallowed regions | 0 (0.0%) |

Values in parentheses are for the highest resolution shell

REFERENCES

1. Xu, L. H., et al., *Attenuation of the expression of the focal adhesion kinase induces apoptosis in tumor cells*. Cell Growth Differ, 1996. 7(4): p. 413-8.
2. McLean, G. W., et al., *The role of focal-adhesion kinase in cancer—a new therapeutic opportunity*. Nat Rev Cancer, 2005. 5(7): p. 505-15.
3. van Nimwegen, M. J. and B. van de Water, *Focal adhesion kinase: A potential target in cancer therapy*. Biochem Pharmacol, 2006.
4. Weiner, T. M., et al., *Expression of focal adhesion kinase gene and invasive cancer*. Lancet, 1993. 342(8878): p. 1024-5.
5. Owens, L. V., et al., *Overexpression of the focal adhesion kinase (p125FAK) in invasive human tumors*. Cancer Research, 1995. 55(13): p. 2752-5.
6. Golubovskaya, V. M., R. Finch, and W. G. Cance, *Direct interaction of the N-terminal domain of focal adhesion kinase with the N-terminal transactivation domain of p53*. J Biol Chem, 2005. 280(26): p. 25008-21.
7. Garces, C. A., et al., *Vascular endothelial growth factor receptor-3 and focal adhesion kinase bind and suppress apoptosis in breast cancer cells*. Cancer Res, 2006. 66(3): p. 1446-54.

The disclosures of each and every patent, patent application and publication cited herein are hereby incorporated herein by reference in their entirety.

Focal Adhesion Kinase (FAK) is an important survival molecule that is upregulated in a broad range of solid tumors and is expressed at very low levels in normal tissues, creating a therapeutic window and making this protein a highly attractive target for the treatment of cancer, as suggested by our lab and recently by other leading authors in the field. We have identified the key-binding partners of FAK and peptides from the binding sites that cause apoptosis in cancer but not normal cells. Based on these findings as well as correlative structural and functional data, we suggest that blocking FAK-protein interactions will lead to apoptosis and tumor cell death. We have well-documented data that targeting FAK-protein interactions is important for cell survival and we have used atomic resolution structural data of specific binding sites to identify small molecule lead compounds. We have screened small molecule libraries and identified several lead compounds that disrupt binding of FAK to key signaling molecules and induce apoptosis in breast, colon, pancreatic, lung, as well as melanoma cancer cell lines. Some of these compounds caused apoptosis at low nanomolar concentrations. We also have shown that lead compounds increase the sensitivity of cancer cells to standard chemotherapy drugs.

Our data suggest that peptides and small molecule inhibitors of FAK-protein interaction can be identified as lead compounds to provide the basis for targeted novel cancer therapeutic agents. Such compounds will effectively reduce activation of both molecules involved in survival signaling and will lead to sensitivity to chemotherapy and cancer cell death. We anticipate that our approach (targeting FAK protein-protein interactions) is amenable to more successful drug discovery and development than the typical method of targeting the kinase activity by targeting ATP binding site of tyrosine kinases. Experience shows that it is especially difficult in the case of FAK due to cross-reactivity with other essential tyrosine kinases.

FIG. 1.1: Focal Adhesion Kinase (FAK) is a 125 kDa protein tyrosine kinase that is localized at contact points between cells and their extracellular matrix (ECM) and is a point of convergence of a number of signaling pathways associated with cell adhesion, invasion, motility, mitogenesis, angiogenesis and oncogenic transformation (FIG. 1.1). Our laboratory was the first to isolate FAK from human tumors, and we demonstrated that FAK mRNA was up regulated in invasive and metastatic human breast and colon cancer samples. FAK plays a major role in survival signaling, and has been linked to detachment-induced apoptosis, or anoikis. We have shown that FAK overexpression suppressed apoptosis, thus providing a survival signal to human cancer cells, and attenuation of FAK caused detachment and apoptosis in breast cancer cells.

FIG. 1.2. Marked upregulation of FAK expression in invasive breast cancer. FAK is massively upregulated in a number of solid human tumors, and is expressed at minimal levels in normal tissue (FIG. 1.2). This suggests there is a "therapeutic window" between normal cells and cancer that can be exploited by therapeutics.

It is still not clear exactly how FAK interacts with its signaling partners to resist activation of the apoptotic cascade. Amino- and Carboxy-terminus of FAK are critical regulators of FAK function. FAK-NT and FAK-CD can displace FAK from focal adhesions of tumor cells and trigger an apoptotic cascade in these cells.

While the emerging data strongly suggests that FAK is an excellent target for developmental therapeutics of cancer, specific small molecule kinase inhibitors of FAK have been difficult to obtain. Targeting the interactions of FAK with critical binding partners can induce apoptosis, we will focus on these protein-protein interactions as a prelude to the development of anti-FAK therapeutics. Studies with peptide inhibitors already have indicated that blockade of specific protein-protein interactions has therapeutic promise for treating a variety of diseases, including cancer. Small organic molecules are particularly attractive as inhibitors of intracellular protein-protein interactions because of the ability to modify their structures to achieve optimal target binding, and because of their ease of delivery in in vivo systems. Thus, there is potential to develop small molecule inhibitors of specific proteins like FAK.

Recently our lab described interaction of the N-terminus of FAK with the serine/threonine kinase RIP, tumor suppressor p53 and demonstrated binding of the C-terminal domain of FAK with the vascular endothelial growth factor receptor-3 VEGFR-3 protein (FIG. 1.1).

FIG. 1.3. Peptide-AV3 causes specific displacement of FAK from the focal adhesions (A), decreased proliferation, increased detachment and apoptosis in breast carcinoma cell lines (B). FAK and VEGFR-3 in BT474 cells were stained for FAK with a Texas Red-conjugated secondary antibody and VEGFR-3 with a Alexa Fluor 488-conjugated secondary antibody and then viewed with a Leica confocal microscope. After 24 hours of peptide-AV3 (black) treatment, staining was repeated, proliferation was measured by MTT assay, apoptosis was measured by Hoechst staining and TUNEL Assay. Control scrambled peptide-AV3S (white) was also used in all experiments. (FIG. 1.10, STEP 2A).

The association of FAK and VEGFR-3 was detected by in vitro and in vivo binding studies. We then showed that a 12-amino-acid VEGFR-3 peptide from the binding site(AV3) caused specific displacement of FAK from the focal adhesions and affected colocalization of FAK and VEGFR-3 in breast cancer cells (FIG. 1.3A). In addition, this peptide decreased proliferation and caused cell detachment and apoptosis in breast cancer cell lines but not in normal breast cells (FIG. 1.3B).

FIG. 1.4. HSQC Overlays of Peptide-35SK. Titration into human FAT domain and Peptide-AV3 and -AV3S peptides titrations into avian FAT domain. (FIG. 1.10, STEP 2B). NMR chemical shift mapping studies have localized the binding epitope of peptides onto FAK-CD (FIG. 1.4). These studies show that selected peptides bind FAK-CD at a site in the same structural pocket that paxillin binds. In silico modeling (FIG. 1.5) showed that peptide binding sites defined by the chemical shifts are appropriate for small drug-like molecule binding.

FIG. 1.5. Site selection for high throughout virtual screening of drug-like compounds to develop small molecule FAK inhibitors. NMR chemical shifts and the crystal structure of the FAT domain of human FAK provided the basis for definition of a structural pocket predicted to accommodate small molecule binding. The crystal structure is shown in cyan and salmon, and residues that undergo shifts upon peptide binding in NMR studies are shown in magenta (His1026 and Ile937). The catalytic tyrosine is shown in green. Red spheres indicate the site defined by the program SPHGEN (UCSF) with chemical and geometric features appropriate for specific small molecule binding. Grey bars demarcate the scoring grid utilized to calculate interactions between potential ligands and the targeted structural pocket. (FIG. 1.10, STEP 3).

FIG. 1.6. Large chemical libraries can be screened to identify drug-like small molecules with the potential to interact with FAK. The coordinates for the molecular model of the human FAK FAT domain and human FAK FERM domain were used in the molecular docking calculations. 240,000 small molecules (NCI/DTP) were each positioned in the structural pockets defined by NMR and crystallography (FIG. 1.5). and scored for their electrostatic and van der Waals interactions. All docking calculations were performed with the DOCK, v5.1.0. The one of the top scoring compounds is shown in yellow in the orientation posed by DOCK5.1 to yield the highest estimated binding score. More than 50 compounds with the highest scores were selected for functional testing from the NCI/DTP. (FIG. 1.10, STEP 3).

In the study, we functionally evaluate the top scoring small molecules in modulating FAK function at the biochemical and cellular levels (FIGS. 1.7-1.10). (FIG. 1.10, STEP 4).

FIG. 1.7. Viability and proliferation assay as a primary test for selected compounds on different cell lines. A. Breast carcinoma cell line BT474 as a primary test-line. Cells plated on 96 well plates, grown 24 h and treated 24 h with 100 mM small molecules, selected for AV3 binding site on FAK-CD (drugs C1-C7) and for big pocket on FAK N-terminus (drugs N1-N16). Data of MTT assay presented as ratio of OD treated to untreated cells. B, C. Analysis of the concentration- and cell line-dependent effects of some selected compounds on PANC-1 cancer cell line. Compound C4 selected against VEGFR3 binding site is selected as lead compound.

FIG. 1.8. VEGFR3-specific effect of compound C4. To prove the specificity of C4 effect on VEGFR3 we utilized stable clone overexpressing wt VEGFR3 in MCF7 cells with low basal expression of the receptor. We found reproducible decrease in viability (A) of VEGFR3 clone after treatment with low concentration of the drug (1 mM), in comparison to control clone transfected with the vector pcDNA3, which is resistant to this concentration of the drug. B. Treatment for 24 h with 10 mM compounds selected for FAT pocket caused dephosphorylation of VEGFR3 only in case of C4 treatment.

FIG. 1.9. Dual treatment of cancer cells with C4 compound and chemotherapeutic drugs. Analysis have revealed sensitivity of cancer cells to dual inhibition. At least additive effect is very pronounced when C4 is combined with doxorubicin treatment. Concentrations correspond to IC50 cell-specific concentration for all used drugs.

Our data suggest that small molecule inhibitors of FAK can be identified as lead compounds to provide the basis for specific novel cancer therapeutic agents. Such compounds will be valuable experimental tools for further analyses of FAK function. Furthermore, they might prove useful pharmaceutically to perturb FAK signaling in the context of human disease, e.g. in cancerous cells overexpressing FAK.

Our next steps will be:
1. Validation of the selected lead compounds in in vivo tumor models
2. Chemical synthesis of the derivatives lead compounds
3. Analysis of the derivatives in in vitro and in vivo using different cancer models.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

TABLE 2

(atomic coordinates disclosed as SEQ ID NO: 7)

| | |
|---|---|
| REMARK | coordinates from restrained individual B-factor refinement |
| REMARK | refinement resolution: 30.0-1.99 A |
| REMARK | starting r = 0.2496 free_r = 0.2627 |
| REMARK | final r = 0.2418 free_r = 0.2489 |
| REMARK | B rmsd for bonded mainchain atoms = 1.372 target = 1.5 |
| REMARK | B rmsd for bonded sidechain atoms = 2.679 target = 2.0 |
| REMARK | B rmsd for angle mainchain atoms = 2.082 target = 2.0 |
| REMARK | B rmsd for angle sidechain atoms = 3.968 target = 2.5 |
| REMARK | rweight = 0.1000 (with wa = 1.2007) |
| REMARK | target = mlf steps = 30 |
| REMARK | sg = P2(1)2(1)2(1) a = 48.246 b = 50.289 c = 49.532 alpha = 90.000 beta = 90.00 |
| REMARK | parameter file 1 : CNS_TOPPAR:protein_rep.param |
| REMARK | parameter file 2 : CNS_TOPPAR:water_rep.param |
| REMARK | parameter file 3 : C4C_AGT_par.txt |
| REMARK | parameter file 4 : CNS_TOPPAR:ion.param |
| REMARK | molecular structure file: fak_generate_easy.mtf |
| REMARK | input coordinates: fak_bgroup.pdb |
| REMARK | reflection file = ps.hkl |
| REMARK | ncs = none |
| REMARK | Anisotropic B-factor tensor Ucart of atomic model without isotropic compo |
| REMARK | B11 = 0.902 B22 = 0.563 B33 = −1.465 |
| REMARK | B12 = 0.000 B13 = 0.000 B23 = 0.000 |
| REMARK | Isotropic component added to coordinate array B: 1.409 |
| REMARK | bulk solvent: probe radius = 1, shrink value = 1 |
| REMARK | bulk solvent: density level = 0.4 e/$\text{A}^3$, B-factor = 46.1478 $\text{A}^2$ |
| REMARK | reflections with \|Fobs\|/sigma_F < 0.0 rejected |
| REMARK | reflections with \|Fobs\| > 10000 * rms(Fobs) rejected |
| REMARK | fft gridding factor = 0.3333, B factor offset = 0 $\text{A}^2$, Elimit = 8 |
| REMARK | theoretical total number of refl. in resol. range: 8676 (100.0%) |
| REMARK | number of unobserved reflections (no entry or \|F\| = 0): 51 (0.6%) |
| REMARK | number of reflections rejected: 0 (0.0%) |
| REMARK | total number of reflections used: 8625 (99.4%) |
| REMARK | number of reflections in working set: 8205 (94.6%) |
| REMARK | number of reflections in test set: 420 (4.8%) |
| CRYST1 | 48.246 50.289 49.532 90.00 90.00 90.00 P 21 21 21 |
| ATOM | 1 CB ASN A 921 −13.126 4.166 6.678 1.00 45.87 A C |
| ATOM | 2 CG ASN A 921 −13.711 2.826 6.279 1.00 43.00 A C |
| ATOM | 3 OD1 ASN A 921 −14.377 2.707 5.251 1.00 44.15 A O |
| ATOM | 4 ND2 ASN A 921 −13.465 1.807 7.094 1.00 43.61 A N |
| ATOM | 5 C ASN A 921 −14.977 5.792 7.124 1.00 46.68 A C |
| ATOM | 6 O ASN A 921 −15.075 5.878 5.900 1.00 48.40 A O |
| ATOM | 7 N ASN A 921 −14.560 3.888 8.651 1.00 49.70 A N |
| ATOM | 8 CA ASN A 921 −13.946 4.867 7.762 1.00 46.32 A C |
| ATOM | 9 N ASP A 922 −15.745 6.482 7.961 1.00 45.70 A N |
| ATOM | 10 CA ASP A 922 −16.977 7.125 7.518 1.00 42.69 A C |
| ATOM | 11 CB ASP A 922 −17.738 7.705 8.712 1.00 46.19 A C |
| ATOM | 12 CG ASP A 922 −19.056 8.338 8.311 1.00 48.18 A C |
| ATOM | 13 OD1 ASP A 922 −19.934 7.611 7.801 1.00 49.06 A O |
| ATOM | 14 OD2 ASP A 922 −19.214 9.561 8.507 1.00 50.40 A O |

TABLE 2-continued (atomic coordinates disclosed as SEQ ID NO: 7)

| ATOM | 15 | C | ASP | A | 922 | −16.691 | 8.220 | 6.496 | 1.00 | 39.97 | A | C |
|---|---|---|---|---|---|---|---|---|---|---|---|---|
| ATOM | 16 | O | ASP | A | 922 | −17.040 | 8.093 | 5.323 | 1.00 | 36.69 | A | O |
| ATOM | 17 | N | LYS | A | 923 | −16.054 | 9.294 | 6.950 | 1.00 | 36.22 | A | N |
| ATOM | 18 | CA | LYS | A | 923 | −15.768 | 10.436 | 6.090 | 1.00 | 34.63 | A | C |
| ATOM | 19 | CB | LYS | A | 923 | −15.092 | 11.553 | 6.888 | 1.00 | 39.76 | A | C |
| ATOM | 20 | CG | LYS | A | 923 | −15.127 | 11.347 | 8.394 | 1.00 | 43.88 | A | C |
| ATOM | 21 | CD | LYS | A | 923 | −15.052 | 12.673 | 9.134 | 1.00 | 47.41 | A | C |
| ATOM | 22 | CE | LYS | A | 923 | −13.630 | 13.209 | 9.164 | 1.00 | 48.42 | A | C |
| ATOM | 23 | NZ | LYS | A | 923 | −13.593 | 14.670 | 9.449 | 1.00 | 47.35 | A | N |
| ATOM | 24 | C | LYS | A | 923 | −14.892 | 10.032 | 4.909 | 1.00 | 31.99 | A | C |
| ATOM | 25 | O | LYS | A | 923 | −15.075 | 10.518 | 3.793 | 1.00 | 30.66 | A | O |
| ATOM | 26 | N | VAL | A | 924 | −13.941 | 9.139 | 5.163 | 1.00 | 27.70 | A | N |
| ATOM | 27 | CA | VAL | A | 924 | −13.050 | 8.651 | 4.117 | 1.00 | 24.87 | A | C |
| ATOM | 28 | CB | VAL | A | 924 | −11.953 | 7.735 | 4.691 | 1.00 | 24.73 | A | C |
| ATOM | 29 | CG1 | VAL | A | 924 | −11.170 | 7.076 | 3.566 | 1.00 | 26.49 | A | C |
| ATOM | 30 | CG2 | VAL | A | 924 | −11.027 | 8.525 | 5.604 | 1.00 | 24.26 | A | C |
| ATOM | 31 | C | VAL | A | 924 | −13.823 | 7.891 | 3.044 | 1.00 | 22.91 | A | C |
| ATOM | 32 | O | VAL | A | 924 | −13.601 | 8.087 | 1.849 | 1.00 | 20.80 | A | O |
| ATOM | 33 | N | TYR | A | 925 | −14.732 | 7.024 | 3.479 | 1.00 | 20.46 | A | N |
| ATOM | 34 | CA | TYR | A | 925 | −15.641 | 6.331 | 2.556 | 1.00 | 21.90 | A | C |
| ATOM | 35 | CB | TYR | A | 925 | −16.532 | 5.341 | 3.310 | 1.00 | 23.36 | A | C |
| ATOM | 36 | CG | TYR | A | 925 | −17.520 | 4.640 | 2.410 | 1.00 | 25.86 | A | C |
| ATOM | 37 | CD1 | TYR | A | 925 | −18.853 | 5.076 | 2.325 | 1.00 | 26.74 | A | C |
| ATOM | 38 | CE1 | TYR | A | 925 | −19.760 | 4.461 | 1.477 | 1.00 | 29.61 | A | C |
| ATOM | 39 | CD2 | TYR | A | 925 | −17.113 | 3.591 | 1.604 | 1.00 | 27.41 | A | C |
| ATOM | 40 | CE2 | TYR | A | 925 | −18.000 | 2.960 | 0.756 | 1.00 | 29.46 | A | C |
| ATOM | 41 | CZ | TYR | A | 925 | −19.322 | 3.396 | 0.686 | 1.00 | 30.35 | A | C |
| ATOM | 42 | OH | TYR | A | 925 | −20.189 | 2.725 | −0.159 | 1.00 | 32.59 | A | O |
| ATOM | 43 | C | TYR | A | 925 | −16.522 | 7.299 | 1.690 | 1.00 | 20.80 | A | C |
| ATOM | 44 | O | TYR | A | 925 | −16.630 | 7.134 | 0.468 | 1.00 | 19.62 | A | O |
| ATOM | 45 | N | GLU | A | 926 | −17.128 | 8.276 | 2.330 | 1.00 | 21.63 | A | N |
| ATOM | 46 | CA | GLU | A | 926 | −17.970 | 9.273 | 1.608 | 1.00 | 23.18 | A | C |
| ATOM | 47 | CB | GLU | A | 926 | −18.579 | 10.271 | 2.587 | 1.00 | 24.32 | A | C |
| ATOM | 48 | CG | GLU | A | 926 | −19.272 | 9.638 | 3.814 | 1.00 | 31.43 | A | C |
| ATOM | 49 | CD | GLU | A | 926 | −20.724 | 9.306 | 3.594 | 1.00 | 35.48 | A | C |
| ATOM | 50 | OE1 | GLU | A | 926 | −20.987 | 8.223 | 2.982 | 1.00 | 36.97 | A | O |
| ATOM | 51 | OE2 | GLU | A | 926 | −21.583 | 10.129 | 4.060 | 1.00 | 38.28 | A | O |
| ATOM | 52 | C | GLU | A | 926 | −17.153 | 10.077 | 0.607 | 1.00 | 21.48 | A | C |
| ATOM | 53 | O | GLU | A | 926 | −17.621 | 10.374 | −0.510 | 1.00 | 20.89 | A | O |
| ATOM | 54 | N | ASN | A | 927 | −15.950 | 10.479 | 1.006 | 1.00 | 21.04 | A | N |
| ATOM | 55 | CA | ASN | A | 927 | −15.117 | 11.251 | 0.062 | 1.00 | 20.73 | A | C |
| ATOM | 56 | CB | ASN | A | 927 | −13.976 | 12.004 | 0.768 | 1.00 | 21.56 | A | C |
| ATOM | 57 | CG | ASN | A | 927 | −14.469 | 13.097 | 1.719 | 1.00 | 25.38 | A | C |
| ATOM | 58 | OD1 | ASN | A | 927 | −15.590 | 13.607 | 1.620 | 1.00 | 27.55 | A | O |
| ATOM | 59 | ND2 | ASN | A | 927 | −13.618 | 13.457 | 2.647 | 1.00 | 27.52 | A | N |
| ATOM | 60 | C | ASN | A | 927 | −14.607 | 10.425 | −1.135 | 1.00 | 20.30 | A | C |
| ATOM | 61 | O | ASN | A | 927 | −14.593 | 10.918 | −2.250 | 1.00 | 19.02 | A | O |
| ATOM | 62 | N | VAL | A | 928 | −14.180 | 9.178 | −0.910 | 1.00 | 18.45 | A | N |
| ATOM | 63 | CA | VAL | A | 928 | −13.767 | 8.309 | −2.035 | 1.00 | 17.68 | A | C |
| ATOM | 64 | CB | VAL | A | 928 | −13.208 | 6.958 | −1.535 | 1.00 | 16.91 | A | C |
| ATOM | 65 | CG1 | VAL | A | 928 | −12.980 | 5.939 | −2.691 | 1.00 | 16.11 | A | C |
| ATOM | 66 | CG2 | VAL | A | 928 | −11.964 | 7.193 | −0.783 | 1.00 | 17.06 | A | C |
| ATOM | 67 | C | VAL | A | 928 | −14.973 | 8.074 | −2.935 | 1.00 | 19.10 | A | C |
| ATOM | 68 | O | VAL | A | 928 | −14.854 | 8.160 | −4.137 | 1.00 | 18.17 | A | O |
| ATOM | 69 | N | THR | A | 929 | −16.137 | 7.802 | −2.353 | 1.00 | 19.89 | A | N |
| ATOM | 70 | CA | THR | A | 929 | −17.338 | 7.551 | −3.163 | 1.00 | 21.64 | A | C |
| ATOM | 71 | CB | THR | A | 929 | −18.567 | 7.134 | −2.293 | 1.00 | 23.02 | A | C |
| ATOM | 72 | OG1 | THR | A | 929 | −18.280 | 5.889 | −1.641 | 1.00 | 26.17 | A | O |
| ATOM | 73 | CG2 | THR | A | 929 | −19.764 | 6.902 | −3.210 | 1.00 | 27.26 | A | C |
| ATOM | 74 | C | THR | A | 929 | −17.716 | 8.769 | −4.004 | 1.00 | 20.65 | A | C |
| ATOM | 75 | O | THR | A | 929 | −18.106 | 8.611 | −5.153 | 1.00 | 21.45 | A | O |
| ATOM | 76 | N | GLY | A | 930 | −17.608 | 9.976 | −3.429 | 1.00 | 18.56 | A | N |
| ATOM | 77 | CA | GLY | A | 930 | −17.935 | 11.230 | −4.142 | 1.00 | 18.61 | A | C |
| ATOM | 78 | C | GLY | A | 930 | −16.979 | 11.516 | −5.291 | 1.00 | 17.45 | A | C |
| ATOM | 79 | O | GLY | A | 930 | −17.398 | 11.908 | −6.373 | 1.00 | 16.87 | A | O |
| ATOM | 80 | N | LEU | A | 931 | −15.701 | 11.214 | −5.056 | 1.00 | 17.73 | A | N |
| ATOM | 81 | CA | LEU | A | 931 | −14.667 | 11.250 | −6.072 | 1.00 | 17.13 | A | C |
| ATOM | 82 | CB | LEU | A | 931 | −13.292 | 10.986 | −5.448 | 1.00 | 18.14 | A | C |
| ATOM | 83 | CG | LEU | A | 931 | −12.091 | 10.936 | −6.388 | 1.00 | 19.54 | A | C |
| ATOM | 84 | CD1 | LEU | A | 931 | −12.073 | 12.232 | −7.295 | 1.00 | 18.89 | A | C |
| ATOM | 85 | CD2 | LEU | A | 931 | −10.785 | 10.828 | −5.561 | 1.00 | 16.88 | A | C |
| ATOM | 86 | C | LEU | A | 931 | −14.941 | 10.265 | −7.212 | 1.00 | 17.99 | A | C |
| ATOM | 87 | O | LEU | A | 931 | −14.951 | 10.674 | −8.379 | 1.00 | 15.98 | A | O |
| ATOM | 88 | N | VAL | A | 932 | −15.205 | 8.990 | −6.895 | 1.00 | 16.23 | A | N |
| ATOM | 89 | CA | VAL | A | 932 | −15.531 | 8.023 | −7.973 | 1.00 | 17.73 | A | C |
| ATOM | 90 | CB | VAL | A | 932 | −15.656 | 6.590 | −7.413 | 1.00 | 18.10 | A | C |
| ATOM | 91 | CG1 | VAL | A | 932 | −16.092 | 5.570 | −8.498 | 1.00 | 17.29 | A | C |
| ATOM | 92 | CG2 | VAL | A | 932 | −14.327 | 6.203 | −6.787 | 1.00 | 17.67 | A | C |

TABLE 2-continued (atomic coordinates disclosed as SEQ ID NO: 7)

| ATOM | 93  | C   | VAL | A | 932 | −16.761 | 8.459  | −8.793  | 1.00 | 17.27 A | C |
|------|-----|-----|-----|---|-----|---------|--------|---------|------|---------|---|
| ATOM | 94  | O   | VAL | A | 932 | −16.793 | 8.334  | −10.042 | 1.00 | 16.14 A | O |
| ATOM | 95  | N   | LYS | A | 933 | −17.776 | 8.970  | −8.098  | 1.00 | 18.27 A | N |
| ATOM | 96  | CA  | LYS | A | 933 | −18.976 | 9.441  | −8.793  | 1.00 | 18.69 A | C |
| ATOM | 97  | CB  | LYS | A | 933 | −20.048 | 9.817  | −7.773  | 1.00 | 22.93 A | C |
| ATOM | 98  | CG  | LYS | A | 933 | −21.363 | 10.192 | −8.372  | 1.00 | 28.01 A | C |
| ATOM | 99  | CD  | LYS | A | 933 | −22.296 | 10.697 | −7.266  | 1.00 | 31.33 A | C |
| ATOM | 100 | CE  | LYS | A | 933 | −23.690 | 10.145 | −7.495  | 1.00 | 33.37 A | C |
| ATOM | 101 | NZ  | LYS | A | 933 | −24.648 | 10.997 | −6.723  | 1.00 | 34.14 A | N |
| ATOM | 102 | C   | LYS | A | 933 | −18.676 | 10.577 | −9.775  | 1.00 | 17.54 A | C |
| ATOM | 103 | O   | LYS | A | 933 | −19.157 | 10.556 | −10.887 | 1.00 | 16.77 A | O |
| ATOM | 104 | N   | ALA | A | 934 | −17.810 | 11.513 | −9.399  | 1.00 | 15.04 A | N |
| ATOM | 105 | CA  | ALA | A | 934 | −17.414 | 12.589 | −10.310 | 1.00 | 15.11 A | C |
| ATOM | 106 | CB  | ALA | A | 934 | −16.523 | 13.565 | −9.594  | 1.00 | 15.13 A | C |
| ATOM | 107 | C   | ALA | A | 934 | −16.721 | 12.012 | −11.557 | 1.00 | 15.24 A | C |
| ATOM | 108 | O   | ALA | A | 934 | −16.860 | 12.537 | −12.659 | 1.00 | 12.42 A | O |
| ATOM | 109 | N   | VAL | A | 935 | −15.950 | 10.925 | −11.363 | 1.00 | 15.01 A | N |
| ATOM | 110 | CA  | VAL | A | 935 | −15.293 | 10.255 | −12.454 | 1.00 | 16.06 A | C |
| ATOM | 111 | CB  | VAL | A | 935 | −14.100 | 9.344  | −11.960 | 1.00 | 14.40 A | C |
| ATOM | 112 | CG1 | VAL | A | 935 | −13.619 | 8.465  | −13.090 | 1.00 | 14.69 A | C |
| ATOM | 113 | CG2 | VAL | A | 935 | −12.945 | 10.194 | −11.391 | 1.00 | 14.75 A | C |
| ATOM | 114 | C   | VAL | A | 935 | −16.296 | 9.481  | −13.327 | 1.00 | 16.60 A | C |
| ATOM | 115 | O   | VAL | A | 935 | −16.187 | 9.492  | −14.549 | 1.00 | 15.55 A | O |
| ATOM | 116 | N   | ILE | A | 936 | −17.258 | 8.932  | −12.785 | 1.00 | 17.48 A | N |
| ATOM | 117 | CA  | ILE | A | 936 | −18.338 | 8.228  | −13.546 | 1.00 | 18.57 A | C |
| ATOM | 118 | CB  | ILE | A | 936 | −19.311 | 7.455  | −12.602 | 1.00 | 18.91 A | C |
| ATOM | 119 | CG2 | ILE | A | 936 | −20.495 | 6.895  | −13.393 | 1.00 | 21.03 A | C |
| ATOM | 120 | CG1 | ILE | A | 936 | −18.574 | 6.336  | −11.863 | 1.00 | 20.31 A | C |
| ATOM | 121 | CD1 | ILE | A | 936 | −19.334 | 5.623  | −10.713 | 1.00 | 17.98 A | C |
| ATOM | 122 | C   | ILE | A | 936 | −19.099 | 9.195  | −14.484 | 1.00 | 19.21 A | C |
| ATOM | 123 | O   | ILE | A | 936 | −19.315 | 8.918  | −15.682 | 1.00 | 16.27 A | O |
| ATOM | 124 | N   | GLU | A | 937 | −19.440 | 10.281 | −13.883 | 1.00 | 18.56 A | N |
| ATOM | 125 | CA  | GLU | A | 937 | −20.100 | 11.339 | −14.634 | 1.00 | 20.58 A | C |
| ATOM | 126 | CB  | GLU | A | 937 | −20.547 | 12.444 | −13.684 | 1.00 | 19.23 A | C |
| ATOM | 127 | CG  | GLU | A | 937 | −21.592 | 11.956 | −12.630 | 1.00 | 21.21 A | C |
| ATOM | 128 | CD  | GLU | A | 937 | −21.726 | 12.916 | −11.407 | 1.00 | 21.46 A | C |
| ATOM | 129 | OE1 | GLU | A | 937 | −22.588 | 12.792 | −10.498 | 1.00 | 21.51 A | O |
| ATOM | 130 | OE2 | GLU | A | 937 | −20.875 | 13.800 | −11.285 | 1.00 | 17.84 A | O |
| ATOM | 131 | C   | GLU | A | 937 | −19.293 | 11.908 | −15.777 | 1.00 | 21.27 A | C |
| ATOM | 132 | O   | GLU | A | 937 | −19.810 | 12.078 | −16.858 | 1.00 | 21.65 A | O |
| ATOM | 133 | N   | MET | A | 938 | −18.014 | 12.220 | −15.538 | 1.00 | 23.03 A | N |
| ATOM | 134 | CA  | MET | A | 938 | −17.119 | 12.613 | −16.627 | 1.00 | 24.52 A | C |
| ATOM | 135 | CB  | MET | A | 938 | −15.704 | 12.917 | −16.093 | 1.00 | 24.97 A | C |
| ATOM | 136 | CG  | MET | A | 938 | −14.880 | 13.788 | −17.032 | 1.00 | 29.98 A | C |
| ATOM | 137 | SD  | MET | A | 938 | −13.110 | 13.624 | −16.658 | 1.00 | 31.53 A | S |
| ATOM | 138 | CE  | MET | A | 938 | −12.511 | 12.952 | −18.208 | 1.00 | 32.64 A | C |
| ATOM | 139 | C   | MET | A | 938 | −17.004 | 11.555 | −17.742 | 1.00 | 25.66 A | C |
| ATOM | 140 | O   | MET | A | 938 | −16.991 | 11.891 | −18.923 | 1.00 | 24.39 A | O |
| ATOM | 141 | N   | SER | A | 939 | −16.922 | 10.289 | −17.347 | 1.00 | 27.00 A | N |
| ATOM | 142 | CA  | SER | A | 939 | −16.673 | 9.206  | −18.292 | 1.00 | 28.99 A | C |
| ATOM | 143 | CB  | SER | A | 939 | −16.248 | 7.936  | −17.551 | 1.00 | 29.57 A | C |
| ATOM | 144 | OG  | SER | A | 939 | −15.090 | 8.166  | −16.767 | 1.00 | 33.47 A | O |
| ATOM | 145 | C   | SER | A | 939 | −17.904 | 8.927  | −19.147 | 1.00 | 29.40 A | C |
| ATOM | 146 | O   | SER | A | 939 | −17.789 | 8.565  | −20.318 | 1.00 | 29.72 A | O |
| ATOM | 147 | N   | SER | A | 940 | −19.081 | 9.097  | −18.554 | 1.00 | 30.15 A | N |
| ATOM | 148 | CA  | SER | A | 940 | −20.327 | 9.100  | −19.312 | 1.00 | 32.56 A | C |
| ATOM | 149 | CB  | SER | A | 940 | −21.521 | 9.316  | −18.379 | 1.00 | 32.16 A | C |
| ATOM | 150 | OG  | SER | A | 940 | −21.627 | 8.264  | −17.435 | 1.00 | 34.65 A | O |
| ATOM | 151 | C   | SER | A | 940 | −20.310 | 10.171 | −20.397 | 1.00 | 33.35 A | C |
| ATOM | 152 | O   | SER | A | 940 | −20.768 | 9.942  | −21.516 | 1.00 | 35.62 A | O |
| ATOM | 153 | N   | LYS | A | 941 | −19.778 | 11.341 | −20.058 | 1.00 | 34.29 A | N |
| ATOM | 154 | CA  | LYS | A | 941 | −20.300 | 12.599 | −20.578 | 1.00 | 35.08 A | C |
| ATOM | 155 | CB  | LYS | A | 941 | −20.527 | 13.596 | −19.440 | 1.00 | 35.59 A | C |
| ATOM | 156 | CG  | LYS | A | 941 | −21.947 | 13.607 | −18.898 | 1.00 | 38.55 A | C |
| ATOM | 157 | CD  | LYS | A | 941 | −22.175 | 14.791 | −17.972 | 1.00 | 39.01 A | C |
| ATOM | 158 | CE  | LYS | A | 941 | −21.760 | 14.465 | −16.547 | 1.00 | 40.62 A | C |
| ATOM | 159 | NZ  | LYS | A | 941 | −21.837 | 15.658 | −15.659 | 1.00 | 40.98 A | N |
| ATOM | 160 | C   | LYS | A | 941 | −19.359 | 13.197 | −21.619 | 1.00 | 35.21 A | C |
| ATOM | 161 | O   | LYS | A | 941 | −19.721 | 14.131 | −22.334 | 1.00 | 33.83 A | O |
| ATOM | 162 | N   | ILE | A | 942 | −18.149 | 12.652 | −21.698 | 1.00 | 35.15 A | N |
| ATOM | 163 | CA  | ILE | A | 942 | −17.008 | 13.392 | −22.222 | 1.00 | 36.51 A | C |
| ATOM | 164 | CB  | ILE | A | 942 | −15.677 | 12.820 | −21.701 | 1.00 | 36.99 A | C |
| ATOM | 165 | CG2 | ILE | A | 942 | −15.481 | 11.394 | −22.193 | 1.00 | 36.78 A | C |
| ATOM | 166 | CG1 | ILE | A | 942 | −14.508 | 13.707 | −22.136 | 1.00 | 37.48 A | C |
| ATOM | 167 | CD1 | ILE | A | 942 | −14.431 | 15.022 | −21.392 | 1.00 | 38.67 A | C |
| ATOM | 168 | C   | ILE | A | 942 | −16.995 | 13.377 | −23.747 | 1.00 | 36.54 A | C |
| ATOM | 169 | O   | ILE | A | 942 | −16.555 | 14.336 | −24.383 | 1.00 | 35.50 A | O |
| ATOM | 170 | N   | GLN | A | 943 | −17.479 | 12.284 | −24.328 | 1.00 | 38.24 A | N |

TABLE 2-continued (atomic coordinates disclosed as SEQ ID NO: 7)

| ATOM | 171 | CA | GLN | A | 943 | −17.389 | 12.078 | −25.768 | 1.00 | 39.56 A | C |
|---|---|---|---|---|---|---|---|---|---|---|---|
| ATOM | 172 | CB | GLN | A | 943 | −18.152 | 10.817 | −26.178 | 1.00 | 43.10 A | C |
| ATOM | 173 | CG | GLN | A | 943 | −17.618 | 10.149 | −27.435 | 1.00 | 47.07 A | C |
| ATOM | 174 | CD | GLN | A | 943 | −18.114 | 8.725 | −27.593 | 1.00 | 49.46 A | C |
| ATOM | 175 | OE1 | GLN | A | 943 | −17.440 | 7.773 | −27.201 | 1.00 | 50.54 A | O |
| ATOM | 176 | NE2 | GLN | A | 943 | −19.300 | 8.573 | −28.172 | 1.00 | 52.23 A | N |
| ATOM | 177 | C | GLN | A | 943 | −17.924 | 13.285 | −26.532 | 1.00 | 39.16 A | C |
| ATOM | 178 | O | GLN | A | 943 | −17.204 | 13.903 | −27.317 | 1.00 | 39.06 A | O |
| ATOM | 179 | N | PRO | A | 944 | −19.190 | 13.614 | −26.298 | 1.00 | 38.44 A | N |
| ATOM | 180 | CD | PRO | A | 944 | −20.101 | 12.941 | −25.356 | 1.00 | 37.81 A | C |
| ATOM | 181 | CA | PRO | A | 944 | −19.858 | 14.685 | −27.044 | 1.00 | 37.97 A | C |
| ATOM | 182 | CB | PRO | A | 944 | −21.336 | 14.462 | −26.717 | 1.00 | 38.08 A | C |
| ATOM | 183 | CG | PRO | A | 944 | −21.326 | 13.811 | −25.380 | 1.00 | 39.10 A | C |
| ATOM | 184 | C | PRO | A | 944 | −19.419 | 16.066 | −26.569 | 1.00 | 36.65 A | C |
| ATOM | 185 | O | PRO | A | 944 | −19.490 | 17.030 | −27.331 | 1.00 | 37.78 A | O |
| ATOM | 186 | N | ALA | A | 945 | −18.971 | 16.153 | −25.321 | 1.00 | 34.59 A | N |
| ATOM | 187 | CA | ALA | A | 945 | −18.827 | 17.439 | −24.646 | 1.00 | 34.33 A | C |
| ATOM | 188 | CB | ALA | A | 945 | −18.584 | 17.218 | −23.159 | 1.00 | 32.24 A | C |
| ATOM | 189 | C | ALA | A | 945 | −17.765 | 18.357 | −25.235 | 1.00 | 33.85 A | C |
| ATOM | 190 | O | ALA | A | 945 | −16.637 | 17.931 | −25.494 | 1.00 | 34.34 A | O |
| ATOM | 191 | N | PRO | A | 946 | −18.117 | 19.636 | −25.441 | 1.00 | 33.96 A | N |
| ATOM | 192 | CD | PRO | A | 946 | −19.466 | 20.224 | −25.394 | 1.00 | 33.39 A | C |
| ATOM | 193 | CA | PRO | A | 946 | −17.112 | 20.646 | −25.739 | 1.00 | 34.50 A | C |
| ATOM | 194 | CB | PRO | A | 946 | −17.964 | 21.812 | −26.248 | 1.00 | 35.16 A | C |
| ATOM | 195 | CG | PRO | A | 946 | −19.188 | 21.707 | −25.441 | 1.00 | 34.84 A | C |
| ATOM | 196 | C | PRO | A | 946 | −16.378 | 21.030 | −24.448 | 1.00 | 33.44 A | C |
| ATOM | 197 | O | PRO | A | 946 | −16.761 | 20.565 | −23.388 | 1.00 | 32.61 A | O |
| ATOM | 198 | N | PRO | A | 947 | −15.305 | 21.824 | −24.547 | 1.00 | 33.93 A | N |
| ATOM | 199 | CD | PRO | A | 947 | −14.709 | 22.215 | −25.838 | 1.00 | 34.22 A | C |
| ATOM | 200 | CA | PRO | A | 947 | −14.520 | 22.336 | −23.406 | 1.00 | 34.33 A | C |
| ATOM | 201 | CB | PRO | A | 947 | −13.516 | 23.278 | −24.073 | 1.00 | 34.49 A | C |
| ATOM | 202 | CG | PRO | A | 947 | −13.388 | 22.718 | −25.465 | 1.00 | 33.72 A | C |
| ATOM | 203 | C | PRO | A | 947 | −15.317 | 23.085 | −22.317 | 1.00 | 34.42 A | C |
| ATOM | 204 | O | PRO | A | 947 | −15.048 | 22.897 | −21.108 | 1.00 | 32.28 A | O |
| ATOM | 205 | N | GLU | A | 948 | −16.267 | 23.926 | −22.744 | 1.00 | 35.20 A | N |
| ATOM | 206 | CA | GLU | A | 948 | −17.245 | 24.529 | −21.827 | 1.00 | 35.78 A | C |
| ATOM | 207 | CB | GLU | A | 948 | −18.261 | 25.433 | −22.581 | 1.00 | 38.56 A | C |
| ATOM | 208 | CG | GLU | A | 948 | −17.779 | 26.902 | −22.627 | 1.00 | 43.76 A | C |
| ATOM | 209 | CD | GLU | A | 948 | −18.551 | 27.842 | −23.602 | 1.00 | 46.99 A | C |
| ATOM | 210 | OE1 | GLU | A | 948 | −19.817 | 27.864 | −23.570 | 1.00 | 48.04 A | O |
| ATOM | 211 | OE2 | GLU | A | 948 | −17.870 | 28.585 | −24.379 | 1.00 | 47.63 A | O |
| ATOM | 212 | C | GLU | A | 948 | −17.959 | 23.519 | −20.906 | 1.00 | 35.01 A | C |
| ATOM | 213 | O | GLU | A | 948 | −18.379 | 23.890 | −19.794 | 1.00 | 35.99 A | O |
| ATOM | 214 | N | GLU | A | 949 | −18.088 | 22.265 | −21.338 | 1.00 | 33.16 A | N |
| ATOM | 215 | CA | GLU | A | 949 | −18.670 | 21.232 | −20.481 | 1.00 | 32.18 A | C |
| ATOM | 216 | CB | GLU | A | 949 | −19.591 | 20.327 | −21.294 | 1.00 | 35.77 A | C |
| ATOM | 217 | CG | GLU | A | 949 | −20.963 | 20.110 | −20.680 | 1.00 | 40.95 A | C |
| ATOM | 218 | CD | GLU | A | 949 | −21.948 | 19.375 | −21.606 | 1.00 | 43.81 A | C |
| ATOM | 219 | OE1 | GLU | A | 949 | −21.793 | 18.140 | −21.819 | 1.00 | 46.07 A | O |
| ATOM | 220 | OE2 | GLU | A | 949 | −22.892 | 20.032 | −22.095 | 1.00 | 45.78 A | O |
| ATOM | 221 | C | GLU | A | 949 | −17.628 | 20.400 | −19.703 | 1.00 | 30.19 A | C |
| ATOM | 222 | O | GLU | A | 949 | −17.698 | 20.328 | −18.475 | 1.00 | 29.89 A | O |
| ATOM | 223 | N | TYR | A | 950 | −16.673 | 19.770 | −20.397 | 1.00 | 26.12 A | N |
| ATOM | 224 | CA | TYR | A | 950 | −15.664 | 18.984 | −19.695 | 1.00 | 23.80 A | C |
| ATOM | 225 | CB | TYR | A | 950 | −14.956 | 17.984 | −20.616 | 1.00 | 21.09 A | C |
| ATOM | 226 | CG | TYR | A | 950 | −14.038 | 18.545 | −21.649 | 1.00 | 20.16 A | C |
| ATOM | 227 | CD1 | TYR | A | 950 | −12.831 | 19.136 | −21.290 | 1.00 | 19.15 A | C |
| ATOM | 228 | CE1 | TYR | A | 950 | −11.937 | 19.618 | −22.280 | 1.00 | 20.11 A | C |
| ATOM | 229 | CD2 | TYR | A | 950 | −14.347 | 18.429 | −23.049 | 1.00 | 18.80 A | C |
| ATOM | 230 | CE2 | TYR | A | 950 | −13.430 | 18.897 | −24.033 | 1.00 | 18.97 A | C |
| ATOM | 231 | CZ | TYR | A | 950 | −12.242 | 19.480 | −23.632 | 1.00 | 19.23 A | C |
| ATOM | 232 | OH | TYR | A | 950 | −11.354 | 19.987 | −24.565 | 1.00 | 19.78 A | O |
| ATOM | 233 | C | TYR | A | 950 | −14.655 | 19.688 | −18.766 | 1.00 | 22.44 A | C |
| ATOM | 234 | O | TYR | A | 950 | −14.133 | 19.054 | −17.848 | 1.00 | 21.66 A | O |
| ATOM | 235 | N | VAL | A | 951 | −14.368 | 20.967 | −18.961 | 1.00 | 22.37 A | N |
| ATOM | 236 | CA | VAL | A | 951 | −13.492 | 21.647 | −17.991 | 1.00 | 22.26 A | C |
| ATOM | 237 | CB | VAL | A | 951 | −12.993 | 23.058 | −18.505 | 1.00 | 23.74 A | C |
| ATOM | 238 | CG1 | VAL | A | 951 | −12.336 | 23.884 | −17.373 | 1.00 | 22.47 A | C |
| ATOM | 239 | CG2 | VAL | A | 951 | −12.041 | 22.846 | −19.672 | 1.00 | 22.28 A | C |
| ATOM | 240 | C | VAL | A | 951 | −14.107 | 21.648 | −16.561 | 1.00 | 22.23 A | C |
| ATOM | 241 | O | VAL | A | 951 | −13.432 | 21.262 | −15.613 | 1.00 | 21.96 A | O |
| ATOM | 242 | N | PRO | A | 952 | −15.373 | 22.082 | −16.402 | 1.00 | 21.23 A | N |
| ATOM | 243 | CD | PRO | A | 952 | −16.261 | 22.740 | −17.389 | 1.00 | 22.78 A | C |
| ATOM | 244 | CA | PRO | A | 952 | −15.987 | 21.995 | −15.082 | 1.00 | 20.89 A | C |
| ATOM | 245 | CB | PRO | A | 952 | −17.393 | 22.570 | −15.295 | 1.00 | 20.12 A | C |
| ATOM | 246 | CG | PRO | A | 952 | −17.264 | 23.455 | −16.534 | 1.00 | 22.95 A | C |
| ATOM | 247 | C | PRO | A | 952 | −16.106 | 20.564 | −14.524 | 1.00 | 19.82 A | C |
| ATOM | 248 | O | PRO | A | 952 | −16.171 | 20.428 | −13.313 | 1.00 | 17.65 A | O |

TABLE 2-continued (atomic coordinates disclosed as SEQ ID NO: 7)

| ATOM | 249 | N   | MET | A | 953 | −16.148 | 19.541 | −15.393 | 1.00 | 19.49 | A | N |
|------|-----|-----|-----|---|-----|---------|--------|---------|------|-------|---|---|
| ATOM | 250 | CA  | MET | A | 953 | −16.124 | 18.128 | −14.968 | 1.00 | 20.58 | A | C |
| ATOM | 251 | CB  | MET | A | 953 | −16.393 | 17.195 | −16.157 | 1.00 | 22.56 | A | C |
| ATOM | 252 | CG  | MET | A | 953 | −17.847 | 17.234 | −16.634 | 1.00 | 24.98 | A | C |
| ATOM | 253 | SD  | MET | A | 953 | −18.095 | 16.075 | −18.000 | 1.00 | 32.64 | A | S |
| ATOM | 254 | CE  | MET | A | 953 | −18.837 | 17.095 | −19.291 | 1.00 | 32.19 | A | C |
| ATOM | 255 | C   | MET | A | 953 | −14.762 | 17.803 | −14.379 | 1.00 | 18.78 | A | C |
| ATOM | 256 | O   | MET | A | 953 | −14.667 | 17.183 | −13.333 | 1.00 | 18.61 | A | O |
| ATOM | 257 | N   | VAL | A | 954 | −13.702 | 18.258 | −15.034 | 1.00 | 18.86 | A | N |
| ATOM | 258 | CA  | VAL | A | 954 | −12.389 | 18.075 | −14.447 | 1.00 | 17.62 | A | C |
| ATOM | 259 | CB  | VAL | A | 954 | −11.244 | 18.393 | −15.443 | 1.00 | 17.31 | A | C |
| ATOM | 260 | CG1 | VAL | A | 954 | −9.833  | 18.379 | −14.699 | 1.00 | 17.39 | A | C |
| ATOM | 261 | CG2 | VAL | A | 954 | −11.298 | 17.409 | −16.650 | 1.00 | 14.02 | A | C |
| ATOM | 262 | C   | VAL | A | 954 | −12.271 | 18.836 | −13.096 | 1.00 | 16.89 | A | C |
| ATOM | 263 | O   | VAL | A | 954 | −11.695 | 18.318 | −12.169 | 1.00 | 17.38 | A | O |
| ATOM | 264 | N   | LYS | A | 955 | −12.799 | 20.059 | −12.990 | 1.00 | 16.39 | A | N |
| ATOM | 265 | CA  | LYS | A | 955 | −12.683 | 20.849 | −11.771 | 1.00 | 16.90 | A | C |
| ATOM | 266 | CB  | LYS | A | 955 | −13.205 | 22.276 | −12.039 | 1.00 | 18.69 | A | C |
| ATOM | 267 | CG  | LYS | A | 955 | −13.493 | 23.109 | −10.801 | 1.00 | 24.22 | A | C |
| ATOM | 268 | CD  | LYS | A | 955 | −14.038 | 24.495 | −11.233 | 1.00 | 26.91 | A | C |
| ATOM | 269 | CE  | LYS | A | 955 | −14.395 | 25.405 | −10.005 | 1.00 | 28.87 | A | C |
| ATOM | 270 | NZ  | LYS | A | 955 | −15.722 | 25.121 | −9.400  | 1.00 | 31.63 | A | N |
| ATOM | 271 | C   | LYS | A | 955 | −13.408 | 20.169 | −10.603 | 1.00 | 15.62 | A | C |
| ATOM | 272 | O   | LYS | A | 955 | −12.956 | 20.157 | −9.442  | 1.00 | 13.00 | A | O |
| ATOM | 273 | N   | GLU | A | 956 | −14.557 | 19.595 | −10.915 | 1.00 | 15.06 | A | N |
| ATOM | 274 | CA  | GLU | A | 956 | −15.309 | 18.795 | −9.958  | 1.00 | 15.51 | A | C |
| ATOM | 275 | CB  | GLU | A | 956 | −16.580 | 18.280 | −10.622 | 1.00 | 15.35 | A | C |
| ATOM | 276 | CG  | GLU | A | 956 | −17.516 | 17.715 | −9.554  | 1.00 | 19.90 | A | C |
| ATOM | 277 | CD  | GLU | A | 956 | −18.635 | 16.853 | −10.076 | 1.00 | 18.83 | A | C |
| ATOM | 278 | OE1 | GLU | A | 956 | −18.985 | 16.825 | −11.255 | 1.00 | 18.32 | A | O |
| ATOM | 279 | OE2 | GLU | A | 956 | −19.204 | 16.159 | −9.237  | 1.00 | 18.35 | A | O |
| ATOM | 280 | C   | GLU | A | 956 | −14.488 | 17.601 | −9.411  | 1.00 | 14.11 | A | C |
| ATOM | 281 | O   | GLU | A | 956 | −14.466 | 17.316 | −8.218  | 1.00 | 11.72 | A | O |
| ATOM | 282 | N   | VAL | A | 957 | −13.836 | 16.880 | −10.308 | 1.00 | 14.54 | A | N |
| ATOM | 283 | CA  | VAL | A | 957 | −12.960 | 15.755 | −9.917  | 1.00 | 15.34 | A | C |
| ATOM | 284 | CB  | VAL | A | 957 | −12.397 | 15.039 | −11.219 | 1.00 | 14.80 | A | C |
| ATOM | 285 | CG1 | VAL | A | 957 | −11.256 | 13.995 | −10.871 | 1.00 | 16.19 | A | C |
| ATOM | 286 | CG2 | VAL | A | 957 | −13.492 | 14.336 | −11.922 | 1.00 | 14.68 | A | C |
| ATOM | 287 | C   | VAL | A | 957 | −11.836 | 16.285 | −9.025  | 1.00 | 14.54 | A | C |
| ATOM | 288 | O   | VAL | A | 957 | −11.576 | 15.760 | −7.958  | 1.00 | 12.94 | A | O |
| ATOM | 289 | N   | GLY | A | 958 | −11.163 | 17.343 | −9.463  | 1.00 | 15.37 | A | N |
| ATOM | 290 | CA  | GLY | A | 958 | −10.055 | 17.914 | −8.700  | 1.00 | 15.71 | A | C |
| ATOM | 291 | C   | GLY | A | 958 | −10.505 | 18.386 | −7.322  | 1.00 | 16.41 | A | C |
| ATOM | 292 | O   | GLY | A | 958 | −9.834  | 18.129 | −6.303  | 1.00 | 15.55 | A | O |
| ATOM | 293 | N   | LEU | A | 959 | −11.669 | 19.023 | −7.252  | 1.00 | 16.85 | A | N |
| ATOM | 294 | CA  | LEU | A | 959 | −12.160 | 19.448 | −5.936  | 1.00 | 18.41 | A | C |
| ATOM | 295 | CB  | LEU | A | 959 | −13.353 | 20.366 | −6.081  | 1.00 | 20.33 | A | C |
| ATOM | 296 | CG  | LEU | A | 959 | −13.130 | 21.849 | −6.264  | 1.00 | 22.00 | A | C |
| ATOM | 297 | CD1 | LEU | A | 959 | −11.722 | 22.290 | −6.376  | 1.00 | 23.84 | A | C |
| ATOM | 298 | CD2 | LEU | A | 959 | −14.028 | 22.457 | −7.265  | 1.00 | 21.93 | A | C |
| ATOM | 299 | C   | LEU | A | 959 | −12.527 | 18.280 | −5.002  | 1.00 | 17.31 | A | C |
| ATOM | 300 | O   | LEU | A | 959 | −12.242 | 18.343 | −3.795  | 1.00 | 17.87 | A | O |
| ATOM | 301 | N   | ALA | A | 960 | −13.197 | 17.268 | −5.548  | 1.00 | 18.07 | A | N |
| ATOM | 302 | CA  | ALA | A | 960 | −13.502 | 16.044 | −4.807  | 1.00 | 18.22 | A | C |
| ATOM | 303 | CB  | ALA | A | 960 | −14.268 | 15.071 | −5.705  | 1.00 | 18.68 | A | C |
| ATOM | 304 | C   | ALA | A | 960 | −12.216 | 15.415 | −4.266  | 1.00 | 17.19 | A | C |
| ATOM | 305 | O   | ALA | A | 960 | −12.172 | 14.965 | −3.116  | 1.00 | 16.20 | A | O |
| ATOM | 306 | N   | LEU | A | 961 | −11.180 | 15.385 | −5.099  | 1.00 | 18.11 | A | N |
| ATOM | 307 | CA  | LEU | A | 961 | −9.876  | 14.873 | −4.684  | 1.00 | 16.89 | A | C |
| ATOM | 308 | CB  | LEU | A | 961 | −8.869  | 14.731 | −5.834  | 1.00 | 16.74 | A | C |
| ATOM | 309 | CG  | LEU | A | 961 | −7.516  | 14.186 | −5.317  | 1.00 | 17.11 | A | C |
| ATOM | 310 | CD1 | LEU | A | 961 | −7.693  | 12.807 | −4.728  | 1.00 | 16.42 | A | C |
| ATOM | 311 | CD2 | LEU | A | 961 | −6.358  | 14.229 | −6.362  | 1.00 | 15.93 | A | C |
| ATOM | 312 | C   | LEU | A | 961 | −9.296  | 15.734 | −3.569  | 1.00 | 18.52 | A | C |
| ATOM | 313 | O   | LEU | A | 961 | −8.781  | 15.166 | −2.576  | 1.00 | 17.76 | A | O |
| ATOM | 314 | N   | ARG | A | 962 | −9.404  | 17.068 | −3.670  | 1.00 | 20.28 | A | N |
| ATOM | 315 | CA  | ARG | A | 962 | −8.900  | 17.947 | −2.599  | 1.00 | 21.40 | A | C |
| ATOM | 316 | CB  | ARG | A | 962 | −9.034  | 19.431 | −2.931  | 1.00 | 26.68 | A | C |
| ATOM | 317 | CG  | ARG | A | 962 | −7.922  | 20.049 | −3.823  | 1.00 | 35.41 | A | C |
| ATOM | 318 | CD  | ARG | A | 962 | −6.515  | 19.903 | −3.204  | 1.00 | 42.31 | A | C |
| ATOM | 319 | NE  | ARG | A | 962 | −5.418  | 20.024 | −4.183  | 1.00 | 47.79 | A | N |
| ATOM | 320 | CZ  | ARG | A | 962 | −4.975  | 19.055 | −4.999  | 1.00 | 49.24 | A | C |
| ATOM | 321 | NH1 | ARG | A | 962 | −5.550  | 17.858 | −5.026  | 1.00 | 49.38 | A | N |
| ATOM | 322 | NH2 | ARG | A | 962 | −3.955  | 19.310 | −5.821  | 1.00 | 49.69 | A | N |
| ATOM | 323 | C   | ARG | A | 962 | −9.590  | 17.692 | −1.261  | 1.00 | 20.28 | A | C |
| ATOM | 324 | O   | ARG | A | 962 | −8.960  | 17.731 | −0.195  | 1.00 | 18.62 | A | O |
| ATOM | 325 | N   | THR | A | 963 | −10.899 | 17.458 | −1.327  | 1.00 | 18.13 | A | N |
| ATOM | 326 | CA  | THR | A | 963 | −11.712 | 17.078 | −0.153  | 1.00 | 18.44 | A | C |

TABLE 2-continued (atomic coordinates disclosed as SEQ ID NO: 7)

| ATOM | 327 | CB | THR | A | 963 | −13.217 | 17.112 | −0.553 | 1.00 | 18.61 | A | C |
|---|---|---|---|---|---|---|---|---|---|---|---|---|
| ATOM | 328 | OG1 | THR | A | 963 | −13.528 | 18.446 | −0.978 | 1.00 | 19.52 | A | O |
| ATOM | 329 | CG2 | THR | A | 963 | −14.139 | 16.726 | 0.616 | 1.00 | 18.43 | A | C |
| ATOM | 330 | C | THR | A | 963 | −11.277 | 15.715 | 0.482 | 1.00 | 18.41 | A | C |
| ATOM | 331 | O | THR | A | 963 | −11.048 | 15.608 | 1.711 | 1.00 | 16.88 | A | O |
| ATOM | 332 | N | LEU | A | 964 | −11.147 | 14.694 | −0.357 | 1.00 | 16.55 | A | N |
| ATOM | 333 | CA | LEU | A | 964 | −10.577 | 13.430 | 0.077 | 1.00 | 17.31 | A | C |
| ATOM | 334 | CB | LEU | A | 964 | −10.453 | 12.459 | −1.110 | 1.00 | 15.95 | A | C |
| ATOM | 335 | CG | LEU | A | 964 | −9.840 | 11.097 | −0.722 | 1.00 | 15.68 | A | C |
| ATOM | 336 | CD1 | LEU | A | 964 | −10.657 | 10.448 | 0.262 | 1.00 | 16.05 | A | C |
| ATOM | 337 | CD2 | LEU | A | 964 | −9.750 | 10.245 | −2.010 | 1.00 | 16.34 | A | C |
| ATOM | 338 | C | LEU | A | 964 | −9.243 | 13.567 | 0.771 | 1.00 | 18.14 | A | C |
| ATOM | 339 | O | LEU | A | 964 | −9.071 | 13.052 | 1.869 | 1.00 | 18.65 | A | O |
| ATOM | 340 | N | LEU | A | 965 | −8.306 | 14.293 | 0.186 | 1.00 | 18.76 | A | N |
| ATOM | 341 | CA | LEU | A | 965 | −6.968 | 14.338 | 0.738 | 1.00 | 18.27 | A | C |
| ATOM | 342 | CB | LEU | A | 965 | −5.996 | 14.915 | −0.288 | 1.00 | 21.16 | A | C |
| ATOM | 343 | CG | LEU | A | 965 | −5.773 | 14.057 | −1.550 | 1.00 | 22.17 | A | C |
| ATOM | 344 | CD1 | LEU | A | 965 | −4.814 | 14.831 | −2.461 | 1.00 | 22.99 | A | C |
| ATOM | 345 | CD2 | LEU | A | 965 | −5.238 | 12.648 | −1.348 | 1.00 | 23.80 | A | C |
| ATOM | 346 | C | LEU | A | 965 | −6.925 | 15.124 | 2.050 | 1.00 | 19.07 | A | C |
| ATOM | 347 | O | LEU | A | 965 | −6.118 | 14.812 | 2.915 | 1.00 | 17.66 | A | O |
| ATOM | 348 | N | ALA | A | 966 | −7.790 | 16.137 | 2.189 | 1.00 | 18.92 | A | N |
| ATOM | 349 | CA | ALA | A | 966 | −7.971 | 16.868 | 3.450 | 1.00 | 19.48 | A | C |
| ATOM | 350 | CB | ALA | A | 966 | −9.007 | 18.024 | 3.252 | 1.00 | 21.75 | A | C |
| ATOM | 351 | C | ALA | A | 966 | −8.444 | 15.940 | 4.557 | 1.00 | 19.65 | A | C |
| ATOM | 352 | O | ALA | A | 966 | −7.922 | 15.966 | 5.689 | 1.00 | 17.88 | A | O |
| ATOM | 353 | N | THR | A | 967 | −9.425 | 15.100 | 4.210 | 1.00 | 19.16 | A | N |
| ATOM | 354 | CA | THR | A | 967 | −10.008 | 14.163 | 5.129 | 1.00 | 20.70 | A | C |
| ATOM | 355 | CB | THR | A | 967 | −11.207 | 13.462 | 4.465 | 1.00 | 21.55 | A | C |
| ATOM | 356 | OG1 | THR | A | 967 | −12.299 | 14.409 | 4.302 | 1.00 | 25.60 | A | O |
| ATOM | 357 | CG2 | THR | A | 967 | −11.670 | 12.282 | 5.300 | 1.00 | 23.07 | A | C |
| ATOM | 358 | C | THR | A | 967 | −8.931 | 13.173 | 5.572 | 1.00 | 19.50 | A | C |
| ATOM | 359 | O | THR | A | 967 | −8.839 | 12.827 | 6.762 | 1.00 | 19.84 | A | O |
| ATOM | 360 | N | VAL | A | 968 | −8.121 | 12.720 | 4.621 | 1.00 | 19.96 | A | N |
| ATOM | 361 | CA | VAL | A | 968 | −7.123 | 11.691 | 4.890 | 1.00 | 21.09 | A | C |
| ATOM | 362 | CB | VAL | A | 968 | −6.513 | 11.142 | 3.587 | 1.00 | 20.22 | A | C |
| ATOM | 363 | CG1 | VAL | A | 968 | −5.274 | 10.313 | 3.890 | 1.00 | 21.59 | A | C |
| ATOM | 364 | CG2 | VAL | A | 968 | −7.541 | 10.318 | 2.827 | 1.00 | 19.75 | A | C |
| ATOM | 365 | C | VAL | A | 968 | −6.005 | 12.227 | 5.777 | 1.00 | 22.65 | A | C |
| ATOM | 366 | O | VAL | A | 968 | −5.417 | 11.488 | 6.567 | 1.00 | 23.22 | A | O |
| ATOM | 367 | N | ASP | A | 969 | −5.715 | 13.517 | 5.642 | 1.00 | 24.11 | A | N |
| ATOM | 368 | CA | ASP | A | 969 | −4.669 | 14.155 | 6.433 | 1.00 | 26.59 | A | C |
| ATOM | 369 | CB | ASP | A | 969 | −4.284 | 15.504 | 5.823 | 1.00 | 28.79 | A | C |
| ATOM | 370 | CG | ASP | A | 969 | −3.330 | 15.364 | 4.653 | 1.00 | 31.69 | A | C |
| ATOM | 371 | OD1 | ASP | A | 969 | −2.544 | 14.393 | 4.639 | 1.00 | 30.98 | A | O |
| ATOM | 372 | OD2 | ASP | A | 969 | −3.366 | 16.224 | 3.749 | 1.00 | 36.56 | A | O |
| ATOM | 373 | C | ASP | A | 969 | −5.109 | 14.341 | 7.881 | 1.00 | 27.41 | A | C |
| ATOM | 374 | O | ASP | A | 969 | −4.280 | 14.404 | 8.789 | 1.00 | 28.59 | A | O |
| ATOM | 375 | N | GLU | A | 970 | −6.419 | 14.427 | 8.090 | 1.00 | 28.06 | A | N |
| ATOM | 376 | CA | GLU | A | 970 | −6.972 | 14.594 | 9.429 | 1.00 | 29.91 | A | C |
| ATOM | 377 | CB | GLU | A | 970 | −8.247 | 15.438 | 9.380 | 1.00 | 33.44 | A | C |
| ATOM | 378 | CG | GLU | A | 970 | −9.529 | 14.623 | 9.315 | 1.00 | 38.33 | A | C |
| ATOM | 379 | CD | GLU | A | 970 | −10.769 | 15.492 | 9.245 | 1.00 | 42.71 | A | C |
| ATOM | 380 | OE1 | GLU | A | 970 | −11.153 | 15.894 | 8.127 | 1.00 | 44.19 | A | O |
| ATOM | 381 | OE2 | GLU | A | 970 | −11.360 | 15.773 | 10.309 | 1.00 | 44.71 | A | O |
| ATOM | 382 | C | GLU | A | 970 | −7.261 | 13.245 | 10.079 | 1.00 | 29.27 | A | C |
| ATOM | 383 | O | GLU | A | 970 | −7.454 | 13.158 | 11.291 | 1.00 | 30.73 | A | O |
| ATOM | 384 | N | THR | A | 971 | −7.288 | 12.195 | 9.264 | 1.00 | 27.21 | A | N |
| ATOM | 385 | CA | THR | A | 971 | −7.289 | 10.816 | 9.779 | 1.00 | 25.82 | A | C |
| ATOM | 386 | CB | THR | A | 971 | −7.914 | 9.781 | 8.728 | 1.00 | 25.47 | A | C |
| ATOM | 387 | OG1 | THR | A | 971 | −9.187 | 10.279 | 8.247 | 1.00 | 25.62 | A | O |
| ATOM | 388 | CG2 | THR | A | 971 | −8.080 | 8.368 | 9.350 | 1.00 | 26.02 | A | C |
| ATOM | 389 | C | THR | A | 971 | −5.893 | 10.360 | 10.193 | 1.00 | 25.16 | A | C |
| ATOM | 390 | O | THR | A | 971 | −5.740 | 9.697 | 11.216 | 1.00 | 24.29 | A | O |
| ATOM | 391 | N | ILE | A | 972 | −4.857 | 10.642 | 9.531 | 1.00 | 24.58 | A | N |
| ATOM | 392 | CA | ILE | A | 972 | −3.481 | 10.120 | 9.821 | 1.00 | 25.30 | A | C |
| ATOM | 393 | CB | ILE | A | 972 | −2.447 | 10.702 | 8.798 | 1.00 | 24.62 | A | C |
| ATOM | 394 | CG2 | ILE | A | 972 | −1.050 | 10.313 | 9.155 | 1.00 | 25.79 | A | C |
| ATOM | 395 | CG1 | ILE | A | 972 | −2.778 | 10.224 | 7.393 | 1.00 | 24.73 | A | C |
| ATOM | 396 | CD1 | ILE | A | 972 | −1.991 | 10.904 | 6.246 | 1.00 | 24.50 | A | C |
| ATOM | 397 | C | ILE | A | 972 | −3.022 | 10.220 | 11.344 | 1.00 | 25.41 | A | C |
| ATOM | 398 | O | ILE | A | 972 | −2.545 | 9.229 | 11.933 | 1.00 | 23.91 | A | O |
| ATOM | 399 | N | PRO | A | 973 | −3.192 | 11.317 | 11.897 | 1.00 | 26.33 | A | N |
| ATOM | 400 | CD | PRO | A | 973 | −3.651 | 12.617 | 11.355 | 1.00 | 26.59 | A | C |
| ATOM | 401 | CA | PRO | A | 973 | −2.877 | 11.476 | 13.334 | 1.00 | 27.10 | A | C |
| ATOM | 402 | CB | PRO | A | 973 | −3.652 | 12.761 | 13.691 | 1.00 | 28.28 | A | C |
| ATOM | 403 | CG | PRO | A | 973 | −3.460 | 13.571 | 12.534 | 1.00 | 27.16 | A | C |
| ATOM | 404 | C | PRO | A | 973 | −3.393 | 10.371 | 14.231 | 1.00 | 27.17 | A | C |

TABLE 2-continued (atomic coordinates disclosed as SEQ ID NO: 7)

| ATOM | 405 | O   | PRO | A | 973 | −2.733 | 10.000 | 15.207 | 1.00 | 27.61 | A | O |
|------|-----|-----|-----|---|-----|--------|--------|--------|------|-------|---|---|
| ATOM | 406 | N   | LEU | A | 974 | −4.575 | 9.859  | 13.902 | 1.00 | 25.65 | A | N |
| ATOM | 407 | CA  | LEU | A | 974 | −5.203 | 8.835  | 14.694 | 1.00 | 24.02 | A | C |
| ATOM | 408 | CB  | LEU | A | 974 | −6.711 | 8.964  | 14.539 | 1.00 | 25.40 | A | C |
| ATOM | 409 | CG  | LEU | A | 974 | −7.196 | 10.418 | 14.522 | 1.00 | 26.92 | A | C |
| ATOM | 410 | CD1 | LEU | A | 974 | −8.647 | 10.492 | 14.074 | 1.00 | 28.17 | A | C |
| ATOM | 411 | CD2 | LEU | A | 974 | −7.015 | 11.108 | 15.885 | 1.00 | 26.75 | A | C |
| ATOM | 412 | C   | LEU | A | 974 | −4.734 | 7.401  | 14.392 | 1.00 | 23.39 | A | C |
| ATOM | 413 | O   | LEU | A | 974 | −5.144 | 6.467  | 15.083 | 1.00 | 23.91 | A | O |
| ATOM | 414 | N   | LEU | A | 975 | −3.895 | 7.190  | 13.382 | 1.00 | 20.49 | A | N |
| ATOM | 415 | CA  | LEU | A | 975 | −3.538 | 5.809  | 13.001 | 1.00 | 20.15 | A | C |
| ATOM | 416 | CB  | LEU | A | 975 | −3.701 | 5.654  | 11.482 | 1.00 | 19.79 | A | C |
| ATOM | 417 | CG  | LEU | A | 975 | −5.043 | 6.121  | 10.929 | 1.00 | 18.48 | A | C |
| ATOM | 418 | CD1 | LEU | A | 975 | −4.960 | 6.232  | 9.374  | 1.00 | 20.62 | A | C |
| ATOM | 419 | CD2 | LEU | A | 975 | −6.103 | 5.142  | 11.367 | 1.00 | 16.14 | A | C |
| ATOM | 420 | C   | LEU | A | 975 | −2.099 | 5.488  | 13.453 | 1.00 | 19.57 | A | C |
| ATOM | 421 | O   | LEU | A | 975 | −1.306 | 6.407  | 13.557 | 1.00 | 20.08 | A | O |
| ATOM | 422 | N   | PRO | A | 976 | −1.749 | 4.204  | 13.726 | 1.00 | 20.50 | A | N |
| ATOM | 423 | CD  | PRO | A | 976 | −2.573 | 2.979  | 13.692 | 1.00 | 21.87 | A | C |
| ATOM | 424 | CA  | PRO | A | 976 | −0.331 | 3.913  | 14.105 | 1.00 | 21.08 | A | C |
| ATOM | 425 | CB  | PRO | A | 976 | −0.284 | 2.374  | 14.241 | 1.00 | 21.58 | A | C |
| ATOM | 426 | CG  | PRO | A | 976 | −1.670 | 1.902  | 14.287 | 1.00 | 22.68 | A | C |
| ATOM | 427 | C   | PRO | A | 976 | 0.701  | 4.396  | 13.059 | 1.00 | 19.88 | A | C |
| ATOM | 428 | O   | PRO | A | 976 | 0.523  | 4.234  | 11.838 | 1.00 | 19.72 | A | O |
| ATOM | 429 | N   | ALA | A | 977 | 1.761  | 5.020  | 13.542 | 1.00 | 20.27 | A | N |
| ATOM | 430 | CA  | ALA | A | 977 | 2.829  | 5.531  | 12.697 | 1.00 | 18.16 | A | C |
| ATOM | 431 | CB  | ALA | A | 977 | 4.039  | 5.975  | 13.590 | 1.00 | 18.99 | A | C |
| ATOM | 432 | C   | ALA | A | 977 | 3.264  | 4.506  | 11.694 | 1.00 | 18.50 | A | C |
| ATOM | 433 | O   | ALA | A | 977 | 3.632  | 4.885  | 10.574 | 1.00 | 14.03 | A | O |
| ATOM | 434 | N   | SER | A | 978 | 3.196  | 3.201  | 12.038 | 1.00 | 16.78 | A | N |
| ATOM | 435 | CA  | SER | A | 978 | 3.693  | 2.149  | 11.115 | 1.00 | 18.84 | A | C |
| ATOM | 436 | CB  | SER | A | 978 | 3.670  | 0.765  | 11.775 | 1.00 | 19.88 | A | C |
| ATOM | 437 | OG  | SER | A | 978 | 2.341  | 0.398  | 12.025 | 1.00 | 23.53 | A | O |
| ATOM | 438 | C   | SER | A | 978 | 2.879  | 2.019  | 9.837  | 1.00 | 19.30 | A | C |
| ATOM | 439 | O   | SER | A | 978 | 3.294  | 1.353  | 8.877  | 1.00 | 18.09 | A | O |
| ATOM | 440 | N   | THR | A | 979 | 1.700  | 2.637  | 9.831  | 1.00 | 17.83 | A | N |
| ATOM | 441 | CA  | THR | A | 979 | 0.825  | 2.552  | 8.653  | 1.00 | 16.88 | A | C |
| ATOM | 442 | CB  | THR | A | 979 | −0.677 | 2.493  | 9.058  | 1.00 | 17.25 | A | C |
| ATOM | 443 | OG1 | THR | A | 979 | −1.058 | 3.706  | 9.721  | 1.00 | 15.04 | A | O |
| ATOM | 444 | CG2 | THR | A | 979 | −0.914 | 1.334  | 9.991  | 1.00 | 17.06 | A | C |
| ATOM | 445 | C   | THR | A | 979 | 1.012  | 3.749  | 7.726  | 1.00 | 17.27 | A | C |
| ATOM | 446 | O   | THR | A | 979 | 0.460  | 3.748  | 6.636  | 1.00 | 16.68 | A | O |
| ATOM | 447 | N   | HIS | A | 980 | 1.721  | 4.788  | 8.167  | 1.00 | 16.41 | A | N |
| ATOM | 448 | CA  | HIS | A | 980 | 1.549  | 6.088  | 7.500  | 1.00 | 18.00 | A | C |
| ATOM | 449 | CB  | HIS | A | 980 | 2.073  | 7.252  | 8.368  | 1.00 | 17.98 | A | C |
| ATOM | 450 | CG  | HIS | A | 980 | 1.289  | 7.480  | 9.618  | 1.00 | 17.82 | A | C |
| ATOM | 451 | CD2 | HIS | A | 980 | 0.290  | 6.774  | 10.199 | 1.00 | 18.15 | A | C |
| ATOM | 452 | ND1 | HIS | A | 980 | 1.486  | 8.566  | 10.421 | 1.00 | 18.65 | A | N |
| ATOM | 453 | CE1 | HIS | A | 980 | 0.679  | 8.525  | 11.469 | 1.00 | 19.11 | A | C |
| ATOM | 454 | NE2 | HIS | A | 980 | −0.082 | 7.460  | 11.333 | 1.00 | 18.85 | A | N |
| ATOM | 455 | C   | HIS | A | 980 | 2.255  | 6.142  | 6.170  | 1.00 | 18.52 | A | C |
| ATOM | 456 | O   | HIS | A | 980 | 1.829  | 6.870  | 5.284  | 1.00 | 18.72 | A | O |
| ATOM | 457 | N   | ARG | A | 981 | 3.375  | 5.430  | 6.062  | 1.00 | 18.11 | A | N |
| ATOM | 458 | CA  | ARG | A | 981 | 4.161  | 5.407  | 4.795  | 1.00 | 18.71 | A | C |
| ATOM | 459 | CB  | ARG | A | 981 | 5.371  | 4.479  | 4.946  | 1.00 | 22.86 | A | C |
| ATOM | 460 | CG  | ARG | A | 981 | 6.784  | 5.109  | 5.000  | 1.00 | 28.93 | A | C |
| ATOM | 461 | CD  | ARG | A | 981 | 7.008  | 6.367  | 5.913  | 1.00 | 30.92 | A | C |
| ATOM | 462 | NE  | ARG | A | 981 | 6.455  | 7.614  | 5.355  | 1.00 | 34.02 | A | N |
| ATOM | 463 | CZ  | ARG | A | 981 | 6.812  | 8.169  | 4.187  | 1.00 | 31.96 | A | C |
| ATOM | 464 | NH1 | ARG | A | 981 | 7.735  | 7.613  | 3.403  | 1.00 | 30.64 | A | N |
| ATOM | 465 | NH2 | ARG | A | 981 | 6.238  | 9.300  | 3.805  | 1.00 | 33.02 | A | N |
| ATOM | 466 | C   | ARG | A | 981 | 3.325  | 4.932  | 3.639  | 1.00 | 16.94 | A | C |
| ATOM | 467 | O   | ARG | A | 981 | 3.312  | 5.536  | 2.554  | 1.00 | 14.12 | A | O |
| ATOM | 468 | N   | GLU | A | 982 | 2.585  | 3.845  | 3.860  | 1.00 | 15.45 | A | N |
| ATOM | 469 | CA  | GLU | A | 982 | 1.774  | 3.281  | 2.776  | 1.00 | 16.83 | A | C |
| ATOM | 470 | CB  | GLU | A | 982 | 1.195  | 1.920  | 3.214  | 1.00 | 17.74 | A | C |
| ATOM | 471 | CG  | GLU | A | 982 | 0.356  | 1.253  | 2.177  | 1.00 | 20.96 | A | C |
| ATOM | 472 | CD  | GLU | A | 982 | 1.087  | 0.973  | 0.911  | 1.00 | 25.45 | A | C |
| ATOM | 473 | OE1 | GLU | A | 982 | 2.313  | 0.653  | 0.975  | 1.00 | 26.54 | A | O |
| ATOM | 474 | OE2 | GLU | A | 982 | 0.431  | 1.051  | −0.170 | 1.00 | 29.27 | A | O |
| ATOM | 475 | C   | GLU | A | 982 | 0.631  | 4.267  | 2.386  | 1.00 | 16.75 | A | C |
| ATOM | 476 | O   | GLU | A | 982 | 0.327  | 4.452  | 1.201  | 1.00 | 14.27 | A | O |
| ATOM | 477 | N   | ILE | A | 983 | 0.041  | 4.918  | 3.388  | 1.00 | 15.18 | A | N |
| ATOM | 478 | CA  | ILE | A | 983 | −1.013 | 5.923  | 3.147  | 1.00 | 17.73 | A | C |
| ATOM | 479 | CB  | ILE | A | 983 | −1.651 | 6.392  | 4.476  | 1.00 | 16.16 | A | C |
| ATOM | 480 | CG2 | ILE | A | 983 | −2.492 | 7.691  | 4.217  | 1.00 | 18.71 | A | C |
| ATOM | 481 | CG1 | ILE | A | 983 | −2.504 | 5.246  | 5.069  | 1.00 | 16.09 | A | C |
| ATOM | 482 | CD1 | ILE | A | 983 | −2.654 | 5.321  | 6.576  | 1.00 | 13.77 | A | C |

TABLE 2-continued (atomic coordinates disclosed as SEQ ID NO: 7)

| ATOM | 483 | C | ILE | A | 983 | −0.457 | 7.122 | 2.362 | 1.00 | 17.87 | A | C |
|---|---|---|---|---|---|---|---|---|---|---|---|---|
| ATOM | 484 | O | ILE | A | 983 | −1.039 | 7.547 | 1.372 | 1.00 | 18.98 | A | O |
| ATOM | 485 | N | GLU | A | 984 | 0.698 | 7.628 | 2.803 | 1.00 | 19.76 | A | N |
| ATOM | 486 | CA | GLU | A | 984 | 1.382 | 8.692 | 2.099 | 1.00 | 20.38 | A | C |
| ATOM | 487 | CB | GLU | A | 984 | 2.611 | 9.177 | 2.887 | 1.00 | 24.07 | A | C |
| ATOM | 488 | CG | GLU | A | 984 | 3.421 | 10.293 | 2.198 | 1.00 | 29.28 | A | C |
| ATOM | 489 | CD | GLU | A | 984 | 3.032 | 11.738 | 2.623 | 1.00 | 33.60 | A | C |
| ATOM | 490 | OE1 | GLU | A | 984 | 3.176 | 12.092 | 3.816 | 1.00 | 33.47 | A | O |
| ATOM | 491 | OE2 | GLU | A | 984 | 2.632 | 12.550 | 1.737 | 1.00 | 37.88 | A | O |
| ATOM | 492 | C | GLU | A | 984 | 1.756 | 8.312 | 0.653 | 1.00 | 19.09 | A | C |
| ATOM | 493 | O | GLU | A | 984 | 1.546 | 9.133 | −0.247 | 1.00 | 18.62 | A | O |
| ATOM | 494 | N | MET | A | 985 | 2.216 | 7.095 | 0.386 | 1.00 | 19.34 | A | N |
| ATOM | 495 | CA | MET | A | 985 | 2.456 | 6.717 | −1.011 | 1.00 | 20.13 | A | C |
| ATOM | 496 | CB | MET | A | 985 | 3.061 | 5.324 | −1.172 | 1.00 | 24.72 | A | C |
| ATOM | 497 | CG | MET | A | 985 | 4.456 | 5.061 | −0.589 | 1.00 | 27.94 | A | C |
| ATOM | 498 | SD | MET | A | 985 | 5.786 | 6.094 | −1.198 | 1.00 | 35.81 | A | S |
| ATOM | 499 | CE | MET | A | 985 | 6.042 | 5.421 | −2.852 | 1.00 | 32.12 | A | C |
| ATOM | 500 | C | MET | A | 985 | 1.146 | 6.741 | −1.820 | 1.00 | 20.03 | A | C |
| ATOM | 501 | O | MET | A | 985 | 1.146 | 7.126 | −2.995 | 1.00 | 19.64 | A | O |
| ATOM | 502 | N | ALA | A | 986 | 0.048 | 6.284 | −1.193 | 1.00 | 20.00 | A | N |
| ATOM | 503 | CA | ALA | A | 986 | −1.257 | 6.217 | −1.863 | 1.00 | 19.18 | A | C |
| ATOM | 504 | CB | ALA | A | 986 | −2.246 | 5.333 | −1.068 | 1.00 | 18.03 | A | C |
| ATOM | 505 | C | ALA | A | 986 | −1.817 | 7.588 | −2.205 | 1.00 | 19.50 | A | C |
| ATOM | 506 | O | ALA | A | 986 | −2.393 | 7.751 | −3.281 | 1.00 | 21.09 | A | O |
| ATOM | 507 | N | GLN | A | 987 | −1.636 | 8.565 | −1.307 | 1.00 | 19.81 | A | N |
| ATOM | 508 | CA | GLN | A | 987 | −1.933 | 9.962 | −1.554 | 1.00 | 21.49 | A | C |
| ATOM | 509 | CB | GLN | A | 987 | −1.663 | 10.815 | −0.313 | 1.00 | 20.71 | A | C |
| ATOM | 510 | CG | GLN | A | 987 | −2.726 | 10.691 | 0.790 | 1.00 | 25.57 | A | C |
| ATOM | 511 | CD | GLN | A | 987 | −2.576 | 11.812 | 1.846 | 1.00 | 28.37 | A | C |
| ATOM | 512 | OE1 | GLN | A | 987 | −1.543 | 11.923 | 2.502 | 1.00 | 31.00 | A | O |
| ATOM | 513 | NE2 | GLN | A | 987 | −3.597 | 12.623 | 1.997 | 1.00 | 29.50 | A | N |
| ATOM | 514 | C | GLN | A | 987 | −1.177 | 10.593 | −2.714 | 1.00 | 21.36 | A | C |
| ATOM | 515 | O | GLN | A | 987 | −1.782 | 11.276 | −3.566 | 1.00 | 19.30 | A | O |
| ATOM | 516 | N | LYS | A | 988 | 0.148 | 10.424 | −2.719 | 1.00 | 21.97 | A | N |
| ATOM | 517 | CA | LYS | A | 988 | 1.012 | 10.956 | −3.796 | 1.00 | 22.78 | A | C |
| ATOM | 518 | CB | LYS | A | 988 | 2.487 | 10.607 | −3.584 | 1.00 | 24.99 | A | C |
| ATOM | 519 | CG | LYS | A | 988 | 3.161 | 11.079 | −2.300 | 1.00 | 27.95 | A | C |
| ATOM | 520 | CD | LYS | A | 988 | 4.607 | 10.471 | −2.256 | 1.00 | 29.49 | A | C |
| ATOM | 521 | CE | LYS | A | 988 | 5.281 | 10.753 | −0.967 | 1.00 | 33.14 | A | C |
| ATOM | 522 | NZ | LYS | A | 988 | 6.382 | 9.760 | −0.749 | 1.00 | 34.74 | A | N |
| ATOM | 523 | C | LYS | A | 988 | 0.605 | 10.420 | −5.168 | 1.00 | 21.75 | A | C |
| ATOM | 524 | O | LYS | A | 988 | 0.705 | 11.124 | −6.186 | 1.00 | 20.25 | A | O |
| ATOM | 525 | N | LEU | A | 989 | 0.175 | 9.170 | −5.207 | 1.00 | 21.61 | A | N |
| ATOM | 526 | CA | LEU | A | 989 | −0.307 | 8.566 | −6.451 | 1.00 | 20.62 | A | C |
| ATOM | 527 | CB | LEU | A | 989 | −0.729 | 7.119 | −6.232 | 1.00 | 20.99 | A | C |
| ATOM | 528 | CG | LEU | A | 989 | −0.319 | 6.066 | −7.253 | 1.00 | 25.33 | A | C |
| ATOM | 529 | CD1 | LEU | A | 989 | −1.250 | 4.859 | −7.231 | 1.00 | 24.96 | A | C |
| ATOM | 530 | CD2 | LEU | A | 989 | −0.167 | 6.598 | −8.693 | 1.00 | 24.93 | A | C |
| ATOM | 531 | C | LEU | A | 989 | −1.520 | 9.315 | −6.984 | 1.00 | 20.16 | A | C |
| ATOM | 532 | O | LEU | A | 989 | −1.599 | 9.593 | −8.177 | 1.00 | 18.15 | A | O |
| ATOM | 533 | N | LEU | A | 990 | −2.489 | 9.581 | −6.111 | 1.00 | 18.17 | A | N |
| ATOM | 534 | CA | LEU | A | 990 | −3.665 | 10.383 | −6.499 | 1.00 | 18.17 | A | C |
| ATOM | 535 | CB | LEU | A | 990 | −4.623 | 10.538 | −5.297 | 1.00 | 18.41 | A | C |
| ATOM | 536 | CG | LEU | A | 990 | −5.272 | 9.182 | −4.936 | 1.00 | 16.12 | A | C |
| ATOM | 537 | CD1 | LEU | A | 990 | −6.017 | 9.261 | −3.668 | 1.00 | 20.14 | A | C |
| ATOM | 538 | CD2 | LEU | A | 990 | −6.279 | 8.750 | −6.106 | 1.00 | 19.22 | A | C |
| ATOM | 539 | C | LEU | A | 990 | −3.327 | 11.750 | −7.087 | 1.00 | 18.99 | A | C |
| ATOM | 540 | O | LEU | A | 990 | −3.894 | 12.164 | −8.086 | 1.00 | 17.76 | A | O |
| ATOM | 541 | N | ASN | A | 991 | −2.421 | 12.458 | −6.434 | 1.00 | 19.32 | A | N |
| ATOM | 542 | CA | ASN | A | 991 | −1.929 | 13.725 | −6.958 | 1.00 | 21.56 | A | C |
| ATOM | 543 | CB | ASN | A | 991 | −0.960 | 14.352 | −5.944 | 1.00 | 24.00 | A | C |
| ATOM | 544 | CG | ASN | A | 991 | −1.680 | 14.831 | −4.708 | 1.00 | 27.40 | A | C |
| ATOM | 545 | OD1 | ASN | A | 991 | −1.182 | 14.727 | −3.584 | 1.00 | 31.01 | A | O |
| ATOM | 546 | ND2 | ASN | A | 991 | −2.872 | 15.360 | −4.908 | 1.00 | 29.83 | A | N |
| ATOM | 547 | C | ASN | A | 991 | −1.311 | 13.651 | −8.345 | 1.00 | 20.66 | A | C |
| ATOM | 548 | O | ASN | A | 991 | −1.563 | 14.496 | −9.176 | 1.00 | 19.91 | A | O |
| ATOM | 549 | N | SER | A | 992 | −0.456 | 12.666 | −8.558 | 1.00 | 20.50 | A | N |
| ATOM | 550 | CA | SER | A | 992 | 0.056 | 12.348 | −9.889 | 1.00 | 21.52 | A | C |
| ATOM | 551 | CB | SER | A | 992 | 1.039 | 11.170 | −9.823 | 1.00 | 23.06 | A | C |
| ATOM | 552 | OG | SER | A | 992 | 2.025 | 11.512 | −8.839 | 1.00 | 28.32 | A | O |
| ATOM | 553 | C | SER | A | 992 | −1.039 | 12.038 | −10.903 | 1.00 | 20.75 | A | C |
| ATOM | 554 | O | SER | A | 992 | −0.969 | 12.545 | −12.019 | 1.00 | 21.02 | A | O |
| ATOM | 555 | N | ASP | A | 993 | −2.007 | 11.190 | −10.530 | 1.00 | 20.44 | A | N |
| ATOM | 556 | CA | ASP | A | 993 | −3.113 | 10.855 | −11.442 | 1.00 | 20.14 | A | C |
| ATOM | 557 | CB | ASP | A | 993 | −4.094 | 9.894 | −10.759 | 1.00 | 23.90 | A | C |
| ATOM | 558 | CG | ASP | A | 993 | −3.534 | 8.499 | −10.535 | 1.00 | 27.36 | A | C |
| ATOM | 559 | OD1 | ASP | A | 993 | −2.637 | 8.034 | −11.284 | 1.00 | 30.53 | A | O |
| ATOM | 560 | OD2 | ASP | A | 993 | −4.043 | 7.809 | −9.618 | 1.00 | 29.74 | A | O |

TABLE 2-continued (atomic coordinates disclosed as SEQ ID NO: 7)

| ATOM | 561 | C | ASP | A | 993 | −3.865 | 12.136 | −11.874 | 1.00 | 18.63 | A | C |
|---|---|---|---|---|---|---|---|---|---|---|---|---|
| ATOM | 562 | O | ASP | A | 993 | −4.215 | 12.327 | −13.070 | 1.00 | 16.12 | A | O |
| ATOM | 563 | N | LEU | A | 994 | −4.102 | 13.022 | −10.907 | 1.00 | 18.79 | A | N |
| ATOM | 564 | CA | LEU | A | 994 | −4.802 | 14.281 | −11.188 | 1.00 | 18.36 | A | C |
| ATOM | 565 | CB | LEU | A | 994 | −5.155 | 15.040 | −9.909 | 1.00 | 19.13 | A | C |
| ATOM | 566 | CG | LEU | A | 994 | −5.926 | 16.346 | −10.146 | 1.00 | 21.01 | A | C |
| ATOM | 567 | CD1 | LEU | A | 994 | −7.249 | 16.134 | −10.946 | 1.00 | 21.20 | A | C |
| ATOM | 568 | CD2 | LEU | A | 994 | −6.232 | 17.045 | −8.854 | 1.00 | 22.09 | A | C |
| ATOM | 569 | C | LEU | A | 994 | −3.975 | 15.177 | −12.116 | 1.00 | 18.48 | A | C |
| ATOM | 570 | O | LEU | A | 994 | −4.541 | 15.804 | −13.000 | 1.00 | 17.64 | A | O |
| ATOM | 571 | N | GLY | A | 995 | −2.644 | 15.199 | −11.901 | 1.00 | 19.21 | A | N |
| ATOM | 572 | CA | GLY | A | 995 | −1.695 | 15.947 | −12.719 | 1.00 | 18.35 | A | C |
| ATOM | 573 | C | GLY | A | 995 | −1.847 | 15.485 | −14.161 | 1.00 | 19.93 | A | C |
| ATOM | 574 | O | GLY | A | 995 | −1.890 | 16.313 | −15.089 | 1.00 | 18.58 | A | O |
| ATOM | 575 | N | GLU | A | 996 | −1.929 | 14.174 | −14.377 | 1.00 | 20.89 | A | N |
| ATOM | 576 | CA | GLU | A | 996 | −2.007 | 13.761 | −15.766 | 1.00 | 21.04 | A | C |
| ATOM | 577 | CB | GLU | A | 996 | −1.457 | 12.356 | −16.049 | 1.00 | 25.68 | A | C |
| ATOM | 578 | CG | GLU | A | 996 | 0.141 | 12.223 | −15.953 | 1.00 | 31.98 | A | C |
| ATOM | 579 | CD | GLU | A | 996 | 0.974 | 12.703 | −17.189 | 1.00 | 35.42 | A | C |
| ATOM | 580 | OE1 | GLU | A | 996 | 2.026 | 12.059 | −17.472 | 1.00 | 39.09 | A | O |
| ATOM | 581 | OE2 | GLU | A | 996 | 0.621 | 13.717 | −17.863 | 1.00 | 37.76 | A | O |
| ATOM | 582 | C | GLU | A | 996 | −3.399 | 14.037 | −16.341 | 1.00 | 20.00 | A | C |
| ATOM | 583 | O | GLU | A | 996 | −3.484 | 14.537 | −17.488 | 1.00 | 17.79 | A | O |
| ATOM | 584 | N | LEU | A | 997 | −4.476 | 13.830 | −15.568 | 1.00 | 17.54 | A | N |
| ATOM | 585 | CA | LEU | A | 997 | −5.804 | 14.270 | −16.045 | 1.00 | 16.36 | A | C |
| ATOM | 586 | CB | LEU | A | 997 | −6.883 | 14.118 | −14.959 | 1.00 | 16.30 | A | C |
| ATOM | 587 | CG | LEU | A | 997 | −8.308 | 14.603 | −15.301 | 1.00 | 16.10 | A | C |
| ATOM | 588 | CD1 | LEU | A | 997 | −8.761 | 14.029 | −16.652 | 1.00 | 17.03 | A | C |
| ATOM | 589 | CD2 | LEU | A | 997 | −9.272 | 14.208 | −14.183 | 1.00 | 15.11 | A | C |
| ATOM | 590 | C | LEU | A | 997 | −5.772 | 15.747 | −16.486 | 1.00 | 16.64 | A | C |
| ATOM | 591 | O | LEU | A | 997 | −6.187 | 16.069 | −17.595 | 1.00 | 16.14 | A | O |
| ATOM | 592 | N | ILE | A | 998 | −5.265 | 16.635 | −15.634 | 1.00 | 15.96 | A | N |
| ATOM | 593 | CA | ILE | A | 998 | −5.243 | 18.073 | −15.940 | 1.00 | 18.87 | A | C |
| ATOM | 594 | CB | ILE | A | 998 | −4.768 | 18.926 | −14.685 | 1.00 | 18.92 | A | C |
| ATOM | 595 | CG2 | ILE | A | 998 | −4.368 | 20.366 | −15.092 | 1.00 | 21.37 | A | C |
| ATOM | 596 | CG1 | ILE | A | 998 | −5.861 | 18.922 | −13.597 | 1.00 | 21.52 | A | C |
| ATOM | 597 | CD1 | ILE | A | 998 | −5.407 | 19.420 | −12.228 | 1.00 | 23.82 | A | C |
| ATOM | 598 | C | ILE | A | 998 | −4.410 | 18.330 | −17.228 | 1.00 | 18.27 | A | C |
| ATOM | 599 | O | ILE | A | 998 | −4.843 | 19.085 | −18.119 | 1.00 | 16.58 | A | O |
| ATOM | 600 | N | ASN | A | 999 | −3.244 | 17.681 | −17.313 | 1.00 | 18.84 | A | N |
| ATOM | 601 | CA | ASN | A | 999 | −2.368 | 17.740 | −18.498 | 1.00 | 19.79 | A | C |
| ATOM | 602 | CB | ASN | A | 999 | −1.119 | 16.874 | −18.300 | 1.00 | 23.56 | A | C |
| ATOM | 603 | CG | ASN | A | 999 | −0.082 | 17.505 | −17.376 | 1.00 | 28.11 | A | C |
| ATOM | 604 | OD1 | ASN | A | 999 | −0.040 | 18.728 | −17.141 | 1.00 | 31.65 | A | O |
| ATOM | 605 | ND2 | ASN | A | 999 | 0.789 | 16.659 | −16.858 | 1.00 | 31.29 | A | N |
| ATOM | 606 | C | ASN | A | 999 | −3.083 | 17.310 | −19.801 | 1.00 | 18.25 | A | C |
| ATOM | 607 | O | ASN | A | 999 | −3.003 | 18.001 | −20.831 | 1.00 | 17.84 | A | O |
| ATOM | 608 | N | LYS | A | 1000 | −3.825 | 16.205 | −19.754 | 1.00 | 18.72 | A | N |
| ATOM | 609 | CA | LYS | A | 1000 | −4.580 | 15.769 | −20.936 | 1.00 | 18.09 | A | C |
| ATOM | 610 | CB | LYS | A | 1000 | −5.085 | 14.316 | −20.811 | 1.00 | 17.42 | A | C |
| ATOM | 611 | CG | LYS | A | 1000 | −4.000 | 13.244 | −20.570 | 1.00 | 20.47 | A | C |
| ATOM | 612 | CD | LYS | A | 1000 | −2.732 | 13.415 | −21.429 | 1.00 | 20.84 | A | C |
| ATOM | 613 | CE | LYS | A | 1000 | −1.627 | 12.374 | −21.036 | 1.00 | 23.24 | A | C |
| ATOM | 614 | NZ | LYS | A | 1000 | −0.224 | 12.826 | −21.442 | 1.00 | 25.76 | A | N |
| ATOM | 615 | C | LYS | A | 1000 | −5.737 | 16.709 | −21.264 | 1.00 | 17.30 | A | C |
| ATOM | 616 | O | LYS | A | 1000 | −6.005 | 16.982 | −22.439 | 1.00 | 16.83 | A | O |
| ATOM | 617 | N | MET | A | 1000 | −6.401 | 17.229 | −20.231 | 1.00 | 16.98 | A | N |
| ATOM | 618 | CA | MET | A | 1001 | −7.439 | 18.260 | −20.433 | 1.00 | 17.96 | A | C |
| ATOM | 619 | CB | MET | A | 1001 | −7.942 | 18.757 | −19.078 | 1.00 | 18.23 | A | C |
| ATOM | 620 | CG | MET | A | 1001 | −9.122 | 19.691 | −19.189 | 1.00 | 20.90 | A | C |
| ATOM | 621 | SD | MET | A | 1001 | −9.396 | 20.570 | −17.643 | 1.00 | 23.58 | A | S |
| ATOM | 622 | CE | MET | A | 1001 | −8.063 | 21.760 | −17.556 | 1.00 | 25.10 | A | C |
| ATOM | 623 | C | MET | A | 1001 | −6.910 | 19.484 | −21.217 | 1.00 | 17.62 | A | C |
| ATOM | 624 | O | MET | A | 1001 | −7.552 | 19.979 | −22.126 | 1.00 | 15.61 | A | O |
| ATOM | 625 | N | LYS | A | 1002 | −5.755 | 19.975 | −20.812 | 1.00 | 19.09 | A | N |
| ATOM | 626 | CA | LYS | A | 1002 | −5.154 | 21.180 | −21.429 | 1.00 | 18.95 | A | C |
| ATOM | 627 | CB | LYS | A | 1002 | −3.873 | 21.588 | −20.716 | 1.00 | 19.57 | A | C |
| ATOM | 628 | CG | LYS | A | 1002 | −4.093 | 22.237 | −19.350 | 1.00 | 21.50 | A | C |
| ATOM | 629 | CD | LYS | A | 1002 | −2.716 | 22.457 | −18.714 | 1.00 | 25.63 | A | C |
| ATOM | 630 | CE | LYS | A | 1002 | −2.776 | 22.950 | −17.243 | 1.00 | 25.96 | A | C |
| ATOM | 631 | NZ | LYS | A | 1002 | −3.051 | 24.397 | −17.225 | 1.00 | 30.26 | A | N |
| ATOM | 632 | C | LYS | A | 1002 | −4.855 | 20.901 | −22.892 | 1.00 | 17.80 | A | C |
| ATOM | 633 | O | LYS | A | 1002 | −5.122 | 21.750 | −23.763 | 1.00 | 18.43 | A | O |
| ATOM | 634 | N | LEU | A | 1003 | −4.360 | 19.699 | −23.175 | 1.00 | 18.45 | A | N |
| ATOM | 635 | CA | LEU | A | 1003 | −4.171 | 19.264 | −24.594 | 1.00 | 18.10 | A | C |
| ATOM | 636 | CB | LEU | A | 1003 | −3.319 | 18.002 | −24.680 | 1.00 | 19.93 | A | C |
| ATOM | 637 | CG | LEU | A | 1003 | −1.844 | 18.234 | −24.273 | 1.00 | 18.86 | A | C |
| ATOM | 638 | CD1 | LEU | A | 1003 | −1.165 | 16.890 | −23.975 | 1.00 | 20.64 | A | C |

TABLE 2-continued (atomic coordinates disclosed as SEQ ID NO: 7)

| ATOM | 639 | CD2 | LEU | A | 1003 | −1.048 | 19.042 | −25.298 | 1.00 | 22.08 | A | C |
|------|-----|-----|-----|---|------|--------|--------|---------|------|-------|---|---|
| ATOM | 640 | C | LEU | A | 1003 | −5.438 | 19.137 | −25.426 | 1.00 | 18.42 | A | C |
| ATOM | 641 | O | LEU | A | 1003 | −5.514 | 19.711 | −26.529 | 1.00 | 17.42 | A | O |
| ATOM | 642 | N | ALA | A | 1004 | −6.450 | 18.437 | −24.879 | 1.00 | 18.65 | A | N |
| ATOM | 643 | CA | ALA | A | 1004 | −7.785 | 18.427 | −25.431 | 1.00 | 19.05 | A | C |
| ATOM | 644 | CB | ALA | A | 1004 | −8.710 | 17.733 | −24.514 | 1.00 | 17.93 | A | C |
| ATOM | 645 | C | ALA | A | 1004 | −8.308 | 19.843 | −25.765 | 1.00 | 19.13 | A | C |
| ATOM | 646 | O | ALA | A | 1004 | −8.891 | 20.048 | −26.866 | 1.00 | 16.54 | A | O |
| ATOM | 647 | N | GLN | A | 1005 | −8.099 | 20.793 | −24.827 | 1.00 | 19.54 | A | N |
| ATOM | 648 | CA | GLN | A | 1005 | −8.528 | 22.200 | −25.011 | 1.00 | 20.49 | A | C |
| ATOM | 649 | CB | GLN | A | 1005 | −8.360 | 23.039 | −23.749 | 1.00 | 22.46 | A | C |
| ATOM | 650 | CG | GLN | A | 1005 | −9.246 | 22.694 | −22.565 | 1.00 | 23.70 | A | C |
| ATOM | 651 | CD | GLN | A | 1005 | −8.978 | 23.612 | −21.364 | 1.00 | 26.28 | A | C |
| ATOM | 652 | OE1 | GLN | A | 1005 | −8.270 | 23.226 | −20.435 | 1.00 | 27.77 | A | O |
| ATOM | 653 | NE2 | GLN | A | 1005 | −9.527 | 24.831 | −21.388 | 1.00 | 26.13 | A | N |
| ATOM | 654 | C | GLN | A | 1005 | −7.700 | 22.836 | −26.104 | 1.00 | 21.16 | A | C |
| ATOM | 655 | O | GLN | A | 1005 | −8.216 | 23.596 | −26.923 | 1.00 | 19.86 | A | O |
| ATOM | 656 | N | GLN | A | 1006 | −6.402 | 22.569 | −26.100 | 1.00 | 20.27 | A | N |
| ATOM | 657 | CA | GLN | A | 1006 | −5.527 | 23.132 | −27.155 | 1.00 | 20.87 | A | C |
| ATOM | 658 | CB | GLN | A | 1006 | −4.074 | 22.711 | −26.960 | 1.00 | 20.53 | A | C |
| ATOM | 659 | CG | GLN | A | 1006 | −3.065 | 23.219 | −28.063 | 1.00 | 21.04 | A | C |
| ATOM | 660 | CD | GLN | A | 1006 | −1.608 | 23.019 | −27.681 | 1.00 | 22.34 | A | C |
| ATOM | 661 | OE1 | GLN | A | 1006 | −1.296 | 22.520 | −26.576 | 1.00 | 22.66 | A | O |
| ATOM | 662 | NE2 | GLN | A | 1006 | −0.685 | 23.437 | −28.581 | 1.00 | 22.33 | A | N |
| ATOM | 663 | C | GLN | A | 1006 | −5.983 | 22.716 | −28.542 | 1.00 | 21.57 | A | C |
| ATOM | 664 | O | GLN | A | 1006 | −5.934 | 23.517 | −29.448 | 1.00 | 20.00 | A | O |
| ATOM | 665 | N | TYR | A | 1007 | −6.420 | 21.469 | −28.686 | 1.00 | 23.49 | A | N |
| ATOM | 666 | CA | TYR | A | 1007 | −6.765 | 20.925 | −29.994 | 1.00 | 24.65 | A | C |
| ATOM | 667 | CB | TYR | A | 1007 | −6.088 | 19.569 | −30.206 | 1.00 | 28.11 | A | C |
| ATOM | 668 | CG | TYR | A | 1007 | −4.588 | 19.654 | −30.381 | 1.00 | 30.72 | A | C |
| ATOM | 669 | CD1 | TYR | A | 1007 | −3.739 | 19.624 | −29.283 | 1.00 | 32.70 | A | C |
| ATOM | 670 | CE1 | TYR | A | 1007 | −2.368 | 19.702 | −29.438 | 1.00 | 34.78 | A | C |
| ATOM | 671 | CD2 | TYR | A | 1007 | −4.022 | 19.764 | −31.644 | 1.00 | 32.80 | A | C |
| ATOM | 672 | CE2 | TYR | A | 1007 | −2.652 | 19.841 | −31.809 | 1.00 | 34.03 | A | C |
| ATOM | 673 | CZ | TYR | A | 1007 | −1.830 | 19.810 | −30.703 | 1.00 | 35.15 | A | C |
| ATOM | 674 | OH | TYR | A | 1007 | −0.466 | 19.887 | −30.862 | 1.00 | 36.17 | A | O |
| ATOM | 675 | C | TYR | A | 1007 | −8.276 | 20.786 | −30.152 | 1.00 | 25.70 | A | C |
| ATOM | 676 | O | TYR | A | 1007 | −8.756 | 19.931 | −30.896 | 1.00 | 23.37 | A | O |
| ATOM | 677 | N | VAL | A | 1008 | −9.019 | 21.632 | −29.446 | 1.00 | 25.97 | A | N |
| ATOM | 678 | CA | VAL | A | 1008 | −10.394 | 21.941 | −29.823 | 1.00 | 28.11 | A | C |
| ATOM | 679 | CB | VAL | A | 1008 | −10.897 | 23.217 | −29.123 | 1.00 | 27.70 | A | C |
| ATOM | 680 | CG1 | VAL | A | 1008 | −10.819 | 23.059 | −27.612 | 1.00 | 31.16 | A | C |
| ATOM | 681 | CG2 | VAL | A | 1008 | −10.096 | 24.425 | −29.582 | 1.00 | 30.18 | A | C |
| ATOM | 682 | C | VAL | A | 1008 | −10.526 | 22.114 | −31.332 | 1.00 | 29.60 | A | C |
| ATOM | 683 | O | VAL | A | 1008 | −9.722 | 22.802 | −31.960 | 1.00 | 29.50 | A | O |
| ATOM | 684 | N | MET | A | 1009 | −11.546 | 21.485 | −31.907 | 1.00 | 32.09 | A | N |
| ATOM | 685 | CA | MET | A | 1009 | −11.840 | 21.642 | −33.327 | 1.00 | 35.48 | A | C |
| ATOM | 686 | CB | MET | A | 1009 | −12.121 | 23.110 | −33.656 | 1.00 | 37.69 | A | C |
| ATOM | 687 | CG | MET | A | 1009 | −13.441 | 23.627 | −33.107 | 1.00 | 41.07 | A | C |
| ATOM | 688 | SD | MET | A | 1009 | −13.634 | 25.407 | −33.322 | 1.00 | 44.32 | A | S |
| ATOM | 689 | CE | MET | A | 1009 | −15.257 | 25.483 | −34.076 | 1.00 | 42.60 | A | C |
| ATOM | 690 | C | MET | A | 1009 | −10.695 | 21.122 | −34.189 | 1.00 | 35.97 | A | C |
| ATOM | 691 | O | MET | A | 1009 | −10.382 | 21.694 | −35.233 | 1.00 | 36.79 | A | O |
| ATOM | 692 | N | THR | A | 1010 | −10.074 | 20.034 | −33.745 | 1.00 | 35.84 | A | N |
| ATOM | 693 | CA | THR | A | 1010 | −9.451 | 19.082 | −34.657 | 1.00 | 35.89 | A | C |
| ATOM | 694 | CB | THR | A | 1010 | −7.937 | 19.334 | −34.788 | 1.00 | 36.69 | A | C |
| ATOM | 695 | OG1 | THR | A | 1010 | −7.244 | 18.650 | −33.736 | 1.00 | 37.23 | A | O |
| ATOM | 696 | CG2 | THR | A | 1010 | −7.636 | 20.822 | −34.704 | 1.00 | 37.94 | A | C |
| ATOM | 697 | C | THR | A | 1010 | −9.680 | 17.647 | −34.196 | 1.00 | 35.39 | A | C |
| ATOM | 698 | O | THR | A | 1010 | −10.235 | 17.411 | −33.123 | 1.00 | 35.05 | A | O |
| ATOM | 699 | N | SER | A | 1010 | −9.250 | 16.692 | −35.014 | 1.00 | 34.12 | A | N |
| ATOM | 700 | CA | SER | A | 1010 | −9.492 | 15.274 | −34.736 | 1.00 | 33.86 | A | C |
| ATOM | 701 | CB | SER | A | 1011 | −9.098 | 14.403 | −35.938 | 1.00 | 33.72 | A | C |
| ATOM | 702 | OG | SER | A | 1011 | −7.727 | 14.612 | −36.236 | 1.00 | 34.78 | A | O |
| ATOM | 703 | C | SER | A | 1011 | −8.752 | 14.815 | −33.488 | 1.00 | 32.99 | A | C |
| ATOM | 704 | O | SER | A | 1011 | −9.126 | 13.817 | −32.902 | 1.00 | 33.60 | A | O |
| ATOM | 705 | N | LEU | A | 1012 | −7.707 | 15.541 | −33.087 | 1.00 | 32.08 | A | N |
| ATOM | 706 | CA | LEU | A | 1012 | −6.922 | 15.245 | −31.852 | 1.00 | 30.96 | A | C |
| ATOM | 707 | CB | LEU | A | 1012 | −5.611 | 16.032 | −31.849 | 1.00 | 30.75 | A | C |
| ATOM | 708 | CG | LEU | A | 1012 | −4.414 | 15.424 | −32.575 | 1.00 | 30.44 | A | C |
| ATOM | 709 | CD1 | LEU | A | 1012 | −3.280 | 16.390 | −32.593 | 1.00 | 32.11 | A | C |
| ATOM | 710 | CD2 | LEU | A | 1012 | −3.997 | 14.170 | −31.844 | 1.00 | 31.12 | A | C |
| ATOM | 711 | C | LEU | A | 1012 | −7.663 | 15.488 | −30.519 | 1.00 | 30.85 | A | C |
| ATOM | 712 | O | LEU | A | 1012 | −7.347 | 14.842 | −29.515 | 1.00 | 29.63 | A | O |
| ATOM | 713 | N | GLN | A | 1013 | −8.640 | 16.405 | −30.509 | 1.00 | 29.91 | A | N |
| ATOM | 714 | CA | GLN | A | 1013 | −9.450 | 16.603 | −29.308 | 1.00 | 30.28 | A | C |
| ATOM | 715 | CB | GLN | A | 1013 | −10.625 | 17.552 | −29.517 | 1.00 | 29.91 | A | C |
| ATOM | 716 | CG | GLN | A | 1013 | −11.304 | 17.828 | −28.155 | 1.00 | 31.67 | A | C |

TABLE 2-continued (atomic coordinates disclosed as SEQ ID NO: 7)

| ATOM | 717 | CD | GLN | A | 1013 | −12.446 | 18.783 | −28.232 | 1.00 | 32.42 | A | C |
|---|---|---|---|---|---|---|---|---|---|---|---|---|
| ATOM | 718 | OE1 | GLN | A | 1013 | −13.162 | 18.837 | −29.239 | 1.00 | 33.77 | A | O |
| ATOM | 719 | NE2 | GLN | A | 1013 | −12.632 | 19.563 | −27.170 | 1.00 | 31.93 | A | N |
| ATOM | 720 | C | GLN | A | 1013 | −10.007 | 15.273 | −28.800 | 1.00 | 30.65 | A | C |
| ATOM | 721 | O | GLN | A | 1013 | −9.985 | 15.029 | −27.609 | 1.00 | 28.51 | A | O |
| ATOM | 722 | N | GLN | A | 1014 | −10.479 | 14.417 | −29.704 | 1.00 | 30.92 | A | N |
| ATOM | 723 | CA | GLN | A | 1014 | −10.976 | 13.110 | −29.289 | 1.00 | 32.16 | A | C |
| ATOM | 724 | CB | GLN | A | 1014 | −12.026 | 12.497 | −30.276 | 1.00 | 34.24 | A | C |
| ATOM | 725 | CG | GLN | A | 1014 | −11.523 | 12.095 | −31.660 | 1.00 | 37.48 | A | C |
| ATOM | 726 | CD | GLN | A | 1014 | −11.244 | 10.580 | −31.789 | 1.00 | 39.67 | A | C |
| ATOM | 727 | OE1 | GLN | A | 1014 | −11.617 | 9.951 | −32.791 | 1.00 | 41.14 | A | O |
| ATOM | 728 | NE2 | GLN | A | 1014 | −10.601 | 9.997 | −30.768 | 1.00 | 40.43 | A | N |
| ATOM | 729 | C | GLN | A | 1014 | −9.865 | 12.164 | −28.762 | 1.00 | 32.26 | A | C |
| ATOM | 730 | O | GLN | A | 1014 | −10.081 | 11.530 | −27.730 | 1.00 | 32.04 | A | O |
| ATOM | 731 | N | GLU | A | 1015 | −8.681 | 12.126 | −29.372 | 1.00 | 32.55 | A | N |
| ATOM | 732 | CA | GLU | A | 1015 | −7.527 | 11.373 | −28.796 | 1.00 | 32.50 | A | C |
| ATOM | 733 | CB | GLU | A | 1015 | −6.231 | 11.590 | −29.600 | 1.00 | 36.00 | A | C |
| ATOM | 734 | CG | GLU | A | 1015 | −4.943 | 10.775 | −29.131 | 1.00 | 41.44 | A | C |
| ATOM | 735 | CD | GLU | A | 1015 | −3.642 | 11.070 | −29.946 | 1.00 | 44.84 | A | C |
| ATOM | 736 | OE1 | GLU | A | 1015 | −3.184 | 10.224 | −30.782 | 1.00 | 47.68 | A | O |
| ATOM | 737 | OE2 | GLU | A | 1015 | −3.040 | 12.149 | −29.755 | 1.00 | 46.95 | A | O |
| ATOM | 738 | C | GLU | A | 1015 | −7.262 | 11.821 | −27.336 | 1.00 | 30.80 | A | C |
| ATOM | 739 | O | GLU | A | 1015 | −6.941 | 11.025 | −26.458 | 1.00 | 28.63 | A | O |
| ATOM | 740 | N | TYR | A | 1016 | −7.349 | 13.112 | −27.097 | 1.00 | 27.99 | A | N |
| ATOM | 741 | CA | TYR | A | 1016 | −6.956 | 13.603 | −25.782 | 1.00 | 26.12 | A | C |
| ATOM | 742 | CB | TYR | A | 1016 | −6.496 | 15.038 | −25.852 | 1.00 | 25.92 | A | C |
| ATOM | 743 | CG | TYR | A | 1016 | −5.157 | 15.167 | −26.501 | 1.00 | 28.77 | A | C |
| ATOM | 744 | CD1 | TYR | A | 1016 | −4.030 | 14.655 | −25.892 | 1.00 | 28.95 | A | C |
| ATOM | 745 | CE1 | TYR | A | 1016 | −2.796 | 14.792 | −26.462 | 1.00 | 32.26 | A | C |
| ATOM | 746 | CD2 | TYR | A | 1016 | −5.006 | 15.846 | −27.716 | 1.00 | 29.36 | A | C |
| ATOM | 747 | CE2 | TYR | A | 1016 | −3.757 | 15.995 | −28.292 | 1.00 | 31.53 | A | C |
| ATOM | 748 | CZ | TYR | A | 1016 | −2.663 | 15.463 | −27.659 | 1.00 | 32.59 | A | C |
| ATOM | 749 | OH | TYR | A | 1016 | −1.411 | 15.581 | −28.197 | 1.00 | 34.40 | A | O |
| ATOM | 750 | C | TYR | A | 1016 | −8.032 | 13.390 | −24.730 | 1.00 | 24.51 | A | C |
| ATOM | 751 | O | TYR | A | 1016 | −7.710 | 13.136 | −23.558 | 1.00 | 23.44 | A | O |
| ATOM | 752 | N | LYS | A | 1017 | −9.285 | 13.438 | −25.144 | 1.00 | 22.37 | A | N |
| ATOM | 753 | CA | LYS | A | 1017 | −10.381 | 13.092 | −24.220 | 1.00 | 22.82 | A | C |
| ATOM | 754 | CB | LYS | A | 1017 | −11.730 | 13.346 | −24.866 | 1.00 | 23.90 | A | C |
| ATOM | 755 | CG | LYS | A | 1017 | −12.147 | 14.730 | −25.058 | 1.00 | 22.47 | A | C |
| ATOM | 756 | CD | LYS | A | 1017 | −13.426 | 14.624 | −25.898 | 1.00 | 24.68 | A | C |
| ATOM | 757 | CE | LYS | A | 1017 | −14.211 | 15.872 | −25.811 | 1.00 | 25.00 | A | C |
| ATOM | 758 | NZ | LYS | A | 1017 | −15.448 | 15.718 | −26.582 | 1.00 | 26.39 | A | N |
| ATOM | 759 | C | LYS | A | 1017 | −10.299 | 11.616 | −23.858 | 1.00 | 22.39 | A | C |
| ATOM | 760 | O | LYS | A | 1017 | −10.629 | 11.238 | −22.752 | 1.00 | 21.02 | A | O |
| ATOM | 761 | N | LYS | A | 1018 | −9.902 | 10.767 | −24.810 | 1.00 | 23.06 | A | N |
| ATOM | 762 | CA | LYS | A | 1018 | −9.600 | 9.349 | −24.473 | 1.00 | 24.10 | A | C |
| ATOM | 763 | CB | LYS | A | 1018 | −9.387 | 8.531 | −25.742 | 1.00 | 26.38 | A | C |
| ATOM | 764 | CG | LYS | A | 1018 | −10.716 | 8.477 | −26.549 | 1.00 | 29.42 | A | C |
| ATOM | 765 | CD | LYS | A | 1018 | −10.541 | 8.045 | −28.010 | 1.00 | 31.94 | A | C |
| ATOM | 766 | CE | LYS | A | 1018 | −11.784 | 7.265 | −28.556 | 1.00 | 34.81 | A | C |
| ATOM | 767 | NZ | LYS | A | 1018 | −13.111 | 7.980 | −28.807 | 1.00 | 35.94 | A | N |
| ATOM | 768 | C | LYS | A | 1018 | −8.477 | 9.192 | −23.442 | 1.00 | 23.06 | A | C |
| ATOM | 769 | O | LYS | A | 1018 | −8.585 | 8.382 | −22.506 | 1.00 | 23.24 | A | O |
| ATOM | 770 | N | GLN | A | 1019 | −7.447 | 10.033 | −23.549 | 1.00 | 22.06 | A | N |
| ATOM | 771 | CA | GLN | A | 1019 | −6.358 | 10.014 | −22.586 | 1.00 | 21.95 | A | C |
| ATOM | 772 | CB | GLN | A | 1019 | −5.161 | 10.784 | −23.133 | 1.00 | 22.57 | A | C |
| ATOM | 773 | CG | GLN | A | 1019 | −4.587 | 10.168 | −24.426 | 1.00 | 26.58 | A | C |
| ATOM | 774 | CD | GLN | A | 1019 | −3.332 | 10.851 | −24.912 | 1.00 | 28.88 | A | C |
| ATOM | 775 | OE1 | GLN | A | 1019 | −2.711 | 11.623 | −24.185 | 1.00 | 30.81 | A | O |
| ATOM | 776 | NE2 | GLN | A | 1019 | −2.942 | 10.568 | −26.161 | 1.00 | 31.95 | A | N |
| ATOM | 777 | C | GLN | A | 1019 | −6.830 | 10.581 | −21.226 | 1.00 | 21.75 | A | C |
| ATOM | 778 | O | GLN | A | 1019 | −6.407 | 10.102 | −20.172 | 1.00 | 20.66 | A | O |
| ATOM | 779 | N | MET | A | 1020 | −7.751 | 11.538 | −21.268 | 1.00 | 19.76 | A | N |
| ATOM | 780 | CA | MET | A | 1020 | −8.400 | 12.071 | −20.069 | 1.00 | 18.91 | A | C |
| ATOM | 781 | CB | MET | A | 1020 | −9.398 | 13.183 | −20.450 | 1.00 | 18.39 | A | C |
| ATOM | 782 | CG | MET | A | 1020 | −8.751 | 14.586 | −20.693 | 1.00 | 17.87 | A | C |
| ATOM | 783 | SD | MET | A | 1020 | −10.018 | 15.791 | −21.211 | 1.00 | 19.50 | A | S |
| ATOM | 784 | CE | MET | A | 1020 | −10.907 | 15.978 | −19.721 | 1.00 | 19.30 | A | C |
| ATOM | 785 | C | MET | A | 1020 | −9.131 | 10.973 | −19.310 | 1.00 | 19.38 | A | C |
| ATOM | 786 | O | MET | A | 1020 | −8.924 | 10.792 | −18.103 | 1.00 | 16.75 | A | O |
| ATOM | 787 | N | LEU | A | 1021 | −9.999 | 10.251 | −20.014 | 1.00 | 19.65 | A | N |
| ATOM | 788 | CA | LEU | A | 1021 | −10.676 | 9.087 | −19.435 | 1.00 | 21.36 | A | C |
| ATOM | 789 | CB | LEU | A | 1021 | −11.576 | 8.360 | −20.475 | 1.00 | 23.75 | A | C |
| ATOM | 790 | CG | LEU | A | 1021 | −12.988 | 8.969 | −20.614 | 1.00 | 26.27 | A | C |
| ATOM | 791 | CD1 | LEU | A | 1021 | −14.005 | 7.908 | −21.012 | 1.00 | 26.76 | A | C |
| ATOM | 792 | CD2 | LEU | A | 1021 | −13.415 | 9.597 | −19.291 | 1.00 | 27.64 | A | C |
| ATOM | 793 | C | LEU | A | 1021 | −9.732 | 8.094 | −18.825 | 1.00 | 21.32 | A | C |
| ATOM | 794 | O | LEU | A | 1021 | −9.971 | 7.612 | −17.714 | 1.00 | 20.52 | A | O |

TABLE 2-continued (atomic coordinates disclosed as SEQ ID NO: 7)

| ATOM | 795 | N | THR | A | 1022 | −8.670 | 7.748 | −19.542 | 1.00 | 21.47 | A | N |
|---|---|---|---|---|---|---|---|---|---|---|---|---|
| ATOM | 796 | CA | THR | A | 1022 | −7.626 | 6.925 | −18.970 | 1.00 | 21.77 | A | C |
| ATOM | 797 | CB | THR | A | 1022 | −6.481 | 6.683 | −19.986 | 1.00 | 22.35 | A | C |
| ATOM | 798 | OG1 | THR | A | 1022 | −7.059 | 6.045 | −21.127 | 1.00 | 24.96 | A | O |
| ATOM | 799 | CG2 | THR | A | 1022 | −5.394 | 5.763 | −19.442 | 1.00 | 24.24 | A | C |
| ATOM | 800 | C | THR | A | 1022 | −7.116 | 7.441 | −17.624 | 1.00 | 20.80 | A | C |
| ATOM | 801 | O | THR | A | 1022 | −7.082 | 6.657 | −16.644 | 1.00 | 18.76 | A | O |
| ATOM | 802 | N | ALA | A | 1023 | −6.718 | 8.720 | −17.556 | 1.00 | 18.94 | A | N |
| ATOM | 803 | CA | ALA | A | 1023 | −6.122 | 9.243 | −16.302 | 1.00 | 19.00 | A | C |
| ATOM | 804 | CB | ALA | A | 1023 | −5.527 | 10.599 | −16.496 | 1.00 | 18.97 | A | C |
| ATOM | 805 | C | ALA | A | 1023 | −7.179 | 9.259 | −15.202 | 1.00 | 16.62 | A | C |
| ATOM | 806 | O | ALA | A | 1023 | −6.877 | 9.000 | −14.037 | 1.00 | 14.48 | A | O |
| ATOM | 807 | N | ALA | A | 1024 | −8.419 | 9.534 | −15.579 | 1.00 | 16.44 | A | N |
| ATOM | 808 | CA | ALA | A | 1024 | −9.486 | 9.666 | −14.585 | 1.00 | 17.19 | A | C |
| ATOM | 809 | CB | ALA | A | 1024 | −10.728 | 10.370 | −15.165 | 1.00 | 18.08 | A | C |
| ATOM | 810 | C | ALA | A | 1024 | −9.825 | 8.302 | −14.077 | 1.00 | 17.19 | A | C |
| ATOM | 811 | O | ALA | A | 1024 | −10.040 | 8.116 | −12.879 | 1.00 | 16.13 | A | O |
| ATOM | 812 | N | HIS | A | 1025 | −9.864 | 7.329 | −14.981 | 1.00 | 19.59 | A | N |
| ATOM | 813 | CA | HIS | A | 1025 | −10.052 | 5.971 | −14.518 | 1.00 | 20.59 | A | C |
| ATOM | 814 | CB | HIS | A | 1025 | −10.399 | 4.966 | −15.639 | 1.00 | 24.36 | A | C |
| ATOM | 815 | CG | HIS | A | 1025 | −11.188 | 3.839 | −15.081 | 1.00 | 30.65 | A | C |
| ATOM | 816 | CD2 | HIS | A | 1025 | −12.488 | 3.496 | −15.223 | 1.00 | 34.15 | A | C |
| ATOM | 817 | ND1 | HIS | A | 1025 | −10.692 | 3.040 | −14.070 | 1.00 | 33.26 | A | N |
| ATOM | 818 | CE1 | HIS | A | 1025 | −11.632 | 2.210 | −13.660 | 1.00 | 34.62 | A | C |
| ATOM | 819 | NE2 | HIS | A | 1025 | −12.722 | 2.437 | −14.369 | 1.00 | 36.58 | A | N |
| ATOM | 820 | C | HIS | A | 1025 | −8.955 | 5.455 | −13.552 | 1.00 | 19.10 | A | C |
| ATOM | 821 | O | HIS | A | 1025 | −9.260 | 4.878 | −12.518 | 1.00 | 17.03 | A | O |
| ATOM | 822 | N | ALA | A | 1026 | −7.700 | 5.781 | −13.813 | 1.00 | 18.54 | A | N |
| ATOM | 823 | CA | ALA | A | 1026 | −6.616 | 5.449 | −12.881 | 1.00 | 17.87 | A | C |
| ATOM | 824 | CB | ALA | A | 1026 | −5.232 | 5.874 | −13.475 | 1.00 | 18.24 | A | C |
| ATOM | 825 | C | ALA | A | 1026 | −6.838 | 6.116 | −11.510 | 1.00 | 16.60 | A | C |
| ATOM | 826 | O | ALA | A | 1026 | −6.634 | 5.495 | −10.467 | 1.00 | 15.58 | A | O |
| ATOM | 827 | N | LEU | A | 1027 | −7.286 | 7.379 | −11.541 | 1.00 | 15.96 | A | N |
| ATOM | 828 | CA | LEU | A | 1027 | −7.591 | 8.156 | −10.334 | 1.00 | 15.81 | A | C |
| ATOM | 829 | CB | LEU | A | 1027 | −8.063 | 9.594 | −10.763 | 1.00 | 17.01 | A | C |
| ATOM | 830 | CG | LEU | A | 1027 | −8.185 | 10.715 | −9.746 | 1.00 | 21.57 | A | C |
| ATOM | 831 | CD1 | LEU | A | 1027 | −8.240 | 12.107 | −10.402 | 1.00 | 21.99 | A | C |
| ATOM | 832 | CD2 | LEU | A | 1027 | −9.413 | 10.506 | −8.961 | 1.00 | 23.36 | A | C |
| ATOM | 833 | C | LEU | A | 1027 | −8.611 | 7.397 | −9.469 | 1.00 | 14.84 | A | C |
| ATOM | 834 | O | LEU | A | 1027 | −8.428 | 7.278 | −8.264 | 1.00 | 13.34 | A | O |
| ATOM | 835 | N | ALA | A | 1028 | −9.690 | 6.896 | −10.087 | 1.00 | 14.43 | A | N |
| ATOM | 836 | CA | ALA | A | 1028 | −10.751 | 6.186 | −9.413 | 1.00 | 14.08 | A | C |
| ATOM | 837 | CB | ALA | A | 1028 | −11.896 | 5.883 | −10.398 | 1.00 | 14.76 | A | C |
| ATOM | 838 | C | ALA | A | 1028 | −10.218 | 4.881 | −8.796 | 1.00 | 13.77 | A | C |
| ATOM | 839 | O | ALA | A | 1028 | −10.496 | 4.573 | −7.635 | 1.00 | 13.62 | A | O |
| ATOM | 840 | N | VAL | A | 1029 | −9.433 | 4.131 | −9.569 | 1.00 | 14.81 | A | N |
| ATOM | 841 | CA | VAL | A | 1029 | −8.803 | 2.899 | −9.045 | 1.00 | 16.95 | A | C |
| ATOM | 842 | CB | VAL | A | 1029 | −8.147 | 2.104 | −10.158 | 1.00 | 17.76 | A | C |
| ATOM | 843 | CG1 | VAL | A | 1029 | −7.280 | 0.939 | −9.602 | 1.00 | 17.18 | A | C |
| ATOM | 844 | CG2 | VAL | A | 1029 | −9.208 | 1.564 | −11.057 | 1.00 | 19.26 | A | C |
| ATOM | 845 | C | VAL | A | 1029 | −7.857 | 3.168 | −7.872 | 1.00 | 16.76 | A | C |
| ATOM | 846 | O | VAL | A | 1029 | −7.881 | 2.471 | −6.868 | 1.00 | 19.12 | A | O |
| ATOM | 847 | N | ASP | A | 1030 | −7.052 | 4.210 | −7.982 | 1.00 | 17.70 | A | N |
| ATOM | 848 | CA | ASP | A | 1030 | −6.123 | 4.604 | −6.935 | 1.00 | 18.21 | A | C |
| ATOM | 849 | CB | ASP | A | 1030 | −5.101 | 5.576 | −7.520 | 1.00 | 21.43 | A | C |
| ATOM | 850 | CG | ASP | A | 1030 | −4.145 | 4.848 | −8.525 | 1.00 | 23.80 | A | C |
| ATOM | 851 | OD1 | ASP | A | 1030 | −4.077 | 3.584 | −8.449 | 1.00 | 27.02 | A | O |
| ATOM | 852 | OD2 | ASP | A | 1030 | −3.478 | 5.516 | −9.357 | 1.00 | 24.96 | A | O |
| ATOM | 853 | C | ASP | A | 1030 | −6.821 | 5.159 | −5.724 | 1.00 | 17.89 | A | C |
| ATOM | 854 | O | ASP | A | 1030 | −6.341 | 4.989 | −4.617 | 1.00 | 16.05 | A | O |
| ATOM | 855 | N | ALA | A | 1031 | −7.994 | 5.772 | −5.923 | 1.00 | 15.57 | A | N |
| ATOM | 856 | CA | ALA | A | 1031 | −8.799 | 6.252 | −4.796 | 1.00 | 15.46 | A | C |
| ATOM | 857 | CB | ALA | A | 1031 | −9.890 | 7.213 | −5.285 | 1.00 | 16.43 | A | C |
| ATOM | 858 | C | ALA | A | 1031 | −9.385 | 5.054 | −3.993 | 1.00 | 15.13 | A | C |
| ATOM | 859 | O | ALA | A | 1031 | −9.378 | 5.054 | −2.749 | 1.00 | 13.29 | A | O |
| ATOM | 860 | N | LYS | A | 1032 | −9.869 | 4.003 | −4.679 | 1.00 | 16.18 | A | N |
| ATOM | 861 | CA | LYS | A | 1032 | −10.290 | 2.771 | −3.937 | 1.00 | 17.78 | A | C |
| ATOM | 862 | CB | LYS | A | 1032 | −11.048 | 2.759 | −4.834 | 1.00 | 20.23 | A | C |
| ATOM | 863 | CG | LYS | A | 1032 | −11.929 | 0.783 | −3.993 | 1.00 | 24.85 | A | C |
| ATOM | 864 | CD | LYS | A | 1032 | −11.850 | −0.682 | −4.496 | 1.00 | 28.44 | A | C |
| ATOM | 865 | CE | LYS | A | 1032 | −12.628 | −1.596 | −3.567 | 1.00 | 29.91 | A | C |
| ATOM | 866 | NZ | LYS | A | 1032 | −11.841 | −2.191 | −2.426 | 1.00 | 31.39 | A | N |
| ATOM | 867 | C | LYS | A | 1032 | −9.108 | 2.052 | −3.276 | 1.00 | 18.06 | A | C |
| ATOM | 868 | O | LYS | A | 1032 | −9.243 | 1.529 | −2.176 | 1.00 | 16.46 | A | O |
| ATOM | 869 | N | ASN | A | 1033 | −7.947 | 2.018 | −3.935 | 1.00 | 18.81 | A | N |
| ATOM | 870 | CA | ASN | A | 1033 | −6.758 | 1.550 | −3.250 | 1.00 | 19.77 | A | C |
| ATOM | 871 | CB | ASN | A | 1033 | −5.509 | 1.632 | −4.121 | 1.00 | 24.13 | A | C |
| ATOM | 872 | CG | ASN | A | 1033 | −4.314 | 1.043 | −3.418 | 1.00 | 27.65 | A | C |

TABLE 2-continued (atomic coordinates disclosed as SEQ ID NO: 7)

| ATOM | 873 | OD1 | ASN | A | 1033 | −4.372 | −0.108 | −2.963 | 1.00 | 30.19 | A | O |
|---|---|---|---|---|---|---|---|---|---|---|---|---|
| ATOM | 874 | ND2 | ASN | A | 1033 | −3.259 | 1.849 | −3.227 | 1.00 | 30.91 | A | N |
| ATOM | 875 | C | ASN | A | 1033 | −6.506 | 2.322 | −1.935 | 1.00 | 19.49 | A | C |
| ATOM | 876 | O | ASN | A | 1033 | −6.215 | 1.721 | −0.913 | 1.00 | 17.37 | A | O |
| ATOM | 877 | N | LEU | A | 1034 | −6.626 | 3.646 | −1.980 | 1.00 | 18.36 | A | N |
| ATOM | 878 | CA | LEU | A | 1034 | −6.375 | 4.478 | −0.805 | 1.00 | 18.20 | A | C |
| ATOM | 879 | CB | LEU | A | 1034 | −6.384 | 5.979 | −1.165 | 1.00 | 17.69 | A | C |
| ATOM | 880 | CG | LEU | A | 1034 | −6.265 | 6.963 | 0.018 | 1.00 | 20.85 | A | C |
| ATOM | 881 | CD1 | LEU | A | 1034 | −4.980 | 6.816 | 0.779 | 1.00 | 22.21 | A | C |
| ATOM | 882 | CD2 | LEU | A | 1034 | −6.455 | 8.371 | −0.391 | 1.00 | 19.15 | A | C |
| ATOM | 883 | C | LEU | A | 1034 | −7.361 | 4.112 | 0.313 | 1.00 | 16.19 | A | C |
| ATOM | 884 | O | LEU | A | 1034 | −6.973 | 3.978 | 1.491 | 1.00 | 13.85 | A | O |
| ATOM | 885 | N | LEU | A | 1035 | −8.619 | 3.966 | −0.064 | 1.00 | 15.77 | A | N |
| ATOM | 886 | CA | LEU | A | 1035 | −9.670 | 3.488 | 0.866 | 1.00 | 16.16 | A | C |
| ATOM | 887 | CB | LEU | A | 1035 | −11.031 | 3.358 | 0.161 | 1.00 | 16.76 | A | C |
| ATOM | 888 | CG | LEU | A | 1035 | −12.148 | 2.884 | 1.128 | 1.00 | 16.46 | A | C |
| ATOM | 889 | CD1 | LEU | A | 1035 | −12.619 | 4.018 | 1.946 | 1.00 | 20.82 | A | C |
| ATOM | 890 | CD2 | LEU | A | 1035 | −13.296 | 2.283 | 0.357 | 1.00 | 20.70 | A | C |
| ATOM | 891 | C | LEU | A | 1035 | −9.333 | 2.161 | 1.574 | 1.00 | 15.43 | A | C |
| ATOM | 892 | O | LEU | A | 1035 | −9.477 | 2.069 | 2.789 | 1.00 | 16.09 | A | O |
| ATOM | 893 | N | ASP | A | 1036 | −8.897 | 1.155 | 0.807 | 1.00 | 16.76 | A | N |
| ATOM | 894 | CA | ASP | A | 1036 | −8.495 | −0.157 | 1.345 | 1.00 | 18.39 | A | C |
| ATOM | 895 | CB | ASP | A | 1036 | −8.070 | −1.081 | 0.175 | 1.00 | 23.22 | A | C |
| ATOM | 896 | CG | ASP | A | 1036 | −9.262 | −1.513 | −0.713 | 1.00 | 26.36 | A | C |
| ATOM | 897 | OD1 | ASP | A | 1036 | −10.435 | −1.186 | −0.374 | 1.00 | 31.81 | A | O |
| ATOM | 898 | OD2 | ASP | A | 1036 | −9.063 | −2.145 | −1.762 | 1.00 | 29.02 | A | O |
| ATOM | 899 | C | ASP | A | 1036 | −7.356 | −0.023 | 2.357 | 1.00 | 16.50 | A | C |
| ATOM | 900 | O | ASP | A | 1036 | −7.370 | −0.629 | 3.400 | 1.00 | 16.14 | A | O |
| ATOM | 901 | N | VAL | A | 1037 | −6.375 | 0.808 | 2.022 | 1.00 | 15.01 | A | N |
| ATOM | 902 | CA | VAL | A | 1037 | −5.201 | 0.973 | 2.830 | 1.00 | 14.87 | A | C |
| ATOM | 903 | CB | VAL | A | 1037 | −4.109 | 1.824 | 2.065 | 1.00 | 15.75 | A | C |
| ATOM | 904 | CG1 | VAL | A | 1037 | −3.024 | 2.245 | 2.990 | 1.00 | 18.28 | A | C |
| ATOM | 905 | CG2 | VAL | A | 1037 | −3.521 | 1.009 | 0.930 | 1.00 | 16.61 | A | C |
| ATOM | 906 | C | VAL | A | 1037 | −5.575 | 1.615 | 4.149 | 1.00 | 13.38 | A | C |
| ATOM | 907 | O | VAL | A | 1037 | −5.163 | 1.147 | 5.222 | 1.00 | 11.69 | A | O |
| ATOM | 908 | N | ILE | A | 1038 | −6.398 | 2.669 | 4.076 | 1.00 | 11.53 | A | N |
| ATOM | 909 | CA | ILE | A | 1038 | −6.810 | 3.367 | 5.291 | 1.00 | 11.26 | A | C |
| ATOM | 910 | CB | ILE | A | 1038 | −7.519 | 4.648 | 4.944 | 1.00 | 13.49 | A | C |
| ATOM | 911 | CG2 | ILE | A | 1038 | −8.291 | 5.224 | 6.158 | 1.00 | 16.47 | A | C |
| ATOM | 912 | CG1 | ILE | A | 1038 | −6.477 | 5.692 | 4.459 | 1.00 | 15.21 | A | C |
| ATOM | 913 | CD1 | ILE | A | 1038 | −5.538 | 6.304 | 5.517 | 1.00 | 23.18 | A | C |
| ATOM | 914 | C | ILE | A | 1038 | −7.698 | 2.469 | 6.133 | 1.00 | 13.95 | A | C |
| ATOM | 915 | O | ILE | A | 1038 | −7.630 | 2.480 | 7.363 | 1.00 | 14.32 | A | O |
| ATOM | 916 | N | ASP | A | 1039 | −8.452 | 1.876 | 5.357 | 1.00 | 15.46 | A | N |
| ATOM | 917 | CA | ASP | A | 1039 | −9.316 | 0.906 | 6.067 | 1.00 | 18.72 | A | C |
| ATOM | 918 | CB | ASP | A | 1039 | −10.113 | 0.212 | 5.003 | 1.00 | 20.76 | A | C |
| ATOM | 919 | CG | ASP | A | 1039 | −11.126 | −0.723 | 5.549 | 1.00 | 24.20 | A | C |
| ATOM | 920 | OD1 | ASP | A | 1039 | −10.925 | −1.941 | 5.447 | 1.00 | 24.48 | A | O |
| ATOM | 921 | OD2 | ASP | A | 1039 | −12.121 | −0.243 | 6.062 | 1.00 | 27.28 | A | O |
| ATOM | 922 | C | ASP | A | 1039 | −8.442 | −0.101 | 6.870 | 1.00 | 19.53 | A | C |
| ATOM | 923 | O | ASP | A | 1039 | −8.651 | −0.332 | 8.058 | 1.00 | 17.55 | A | O |
| ATOM | 924 | N | GLN | A | 1040 | −7.548 | −0.783 | 6.326 | 1.00 | 21.21 | A | N |
| ATOM | 925 | CA | GLN | A | 1040 | −6.570 | −1.689 | 6.983 | 1.00 | 22.34 | A | C |
| ATOM | 926 | CB | GLN | A | 1040 | −5.504 | −2.175 | 5.981 | 1.00 | 26.50 | A | C |
| ATOM | 927 | CG | GLN | A | 1040 | −6.054 | −2.695 | 4.624 | 1.00 | 34.27 | A | C |
| ATOM | 928 | CD | GLN | A | 1040 | −5.146 | −3.745 | 3.930 | 1.00 | 38.55 | A | C |
| ATOM | 929 | OE1 | GLN | A | 1040 | −4.790 | −4.790 | 4.529 | 1.00 | 41.20 | A | O |
| ATOM | 930 | NE2 | GLN | A | 1040 | −4.790 | −3.480 | 2.664 | 1.00 | 39.75 | A | N |
| ATOM | 931 | C | GLN | A | 1040 | −5.895 | −1.043 | 8.188 | 1.00 | 20.69 | A | C |
| ATOM | 932 | O | GLN | A | 1040 | −5.825 | −1.646 | 9.249 | 1.00 | 18.86 | A | O |
| ATOM | 933 | N | ALA | A | 1041 | −5.428 | 0.192 | 8.026 | 1.00 | 18.23 | A | N |
| ATOM | 934 | CA | ALA | A | 1041 | −4.825 | 0.934 | 9.133 | 1.00 | 15.25 | A | C |
| ATOM | 935 | CB | ALA | A | 1041 | −4.290 | 2.267 | 8.663 | 1.00 | 16.89 | A | C |
| ATOM | 936 | C | ALA | A | 1041 | −5.792 | 1.177 | 10.297 | 1.00 | 15.26 | A | C |
| ATOM | 937 | O | ALA | A | 1041 | −5.359 | 1.177 | 11.460 | 1.00 | 15.00 | A | O |
| ATOM | 938 | N | ARG | A | 1042 | −7.070 | 1.456 | 10.016 | 1.00 | 16.10 | A | N |
| ATOM | 939 | CA | ARG | A | 1042 | −8.033 | 1.686 | 11.121 | 1.00 | 17.79 | A | C |
| ATOM | 940 | CB | ARG | A | 1042 | −9.400 | 2.218 | 10.645 | 1.00 | 20.99 | A | C |
| ATOM | 941 | CG | ARG | A | 1042 | −9.416 | 3.488 | 9.784 | 1.00 | 24.81 | A | C |
| ATOM | 942 | CD | ARG | A | 1042 | −10.887 | 3.923 | 9.389 | 1.00 | 29.22 | A | C |
| ATOM | 943 | NE | ARG | A | 1042 | −11.307 | 5.179 | 10.065 | 1.00 | 35.20 | A | N |
| ATOM | 944 | CZ | ARG | A | 1042 | −11.515 | 6.354 | 9.443 | 1.00 | 35.67 | A | C |
| ATOM | 945 | NH1 | ARG | A | 1042 | −11.369 | 6.467 | 8.133 | 1.00 | 35.09 | A | N |
| ATOM | 946 | NH2 | ARG | A | 1042 | −11.900 | 7.421 | 10.125 | 1.00 | 39.11 | A | N |
| ATOM | 947 | C | ARG | A | 1042 | −8.220 | 0.405 | 11.940 | 1.00 | 17.53 | A | C |
| ATOM | 948 | O | ARG | A | 1042 | −8.279 | 0.466 | 13.156 | 1.00 | 17.47 | A | O |
| ATOM | 949 | N | LEU | A | 1043 | −8.210 | −0.753 | 11.263 | 1.00 | 18.45 | A | N |
| ATOM | 950 | CA | LEU | A | 1043 | −8.230 | −2.075 | 11.909 | 1.00 | 20.27 | A | C |

TABLE 2-continued (atomic coordinates disclosed as SEQ ID NO: 7)

| ATOM | 951 | CB | LEU | A | 1043 | −8.234 | −3.177 | 10.814 | 1.00 | 22.08 | A | C |
|---|---|---|---|---|---|---|---|---|---|---|---|---|
| ATOM | 952 | CG | LEU | A | 1043 | −8.963 | −4.509 | 10.876 | 1.00 | 23.83 | A | C |
| ATOM | 953 | CD1 | LEU | A | 1043 | −8.093 | −5.633 | 10.226 | 1.00 | 22.57 | A | C |
| ATOM | 954 | CD2 | LEU | A | 1043 | −9.474 | −4.913 | 12.248 | 1.00 | 22.67 | A | C |
| ATOM | 955 | C | LEU | A | 1043 | −6.998 | −2.263 | 12.784 | 1.00 | 20.35 | A | C |
| ATOM | 956 | O | LEU | A | 1043 | −7.083 | −2.676 | 13.938 | 1.00 | 19.06 | A | O |
| ATOM | 957 | N | LYS | A | 1044 | −5.835 | −1.930 | 12.232 | 1.00 | 21.90 | A | N |
| ATOM | 958 | CA | LYS | A | 1044 | −4.589 | −1.927 | 13.012 | 1.00 | 23.99 | A | C |
| ATOM | 959 | CB | LYS | A | 1044 | −3.402 | −1.560 | 12.127 | 1.00 | 26.60 | A | C |
| ATOM | 960 | CG | LYS | A | 1044 | −2.997 | −2.713 | 11.267 | 1.00 | 30.71 | A | C |
| ATOM | 961 | CD | LYS | A | 1044 | −1.728 | −2.465 | 10.573 | 1.00 | 33.68 | A | C |
| ATOM | 962 | CE | LYS | A | 1044 | −1.232 | −3.798 | 9.993 | 1.00 | 37.21 | A | C |
| ATOM | 963 | NZ | LYS | A | 1044 | −0.021 | −3.569 | 9.160 | 1.00 | 36.60 | A | N |
| ATOM | 964 | C | LYS | A | 1044 | −4.623 | −1.003 | 14.214 | 1.00 | 23.98 | A | C |
| ATOM | 965 | O | LYS | A | 1044 | −4.099 | −1.348 | 15.247 | 1.00 | 23.36 | A | O |
| ATOM | 966 | N | MET | A | 1045 | −5.194 | 0.186 | 14.064 | 1.00 | 26.19 | A | N |
| ATOM | 967 | CA | MET | A | 1045 | −5.417 | 1.124 | 15.178 | 1.00 | 27.10 | A | C |
| ATOM | 968 | CB | MET | A | 1045 | −6.185 | 2.373 | 14.684 | 1.00 | 28.91 | A | C |
| ATOM | 969 | CG | MET | A | 1045 | −6.495 | 3.466 | 15.739 | 1.00 | 31.74 | A | C |
| ATOM | 970 | SD | MET | A | 1045 | −7.760 | 4.700 | 15.207 | 1.00 | 36.78 | A | S |
| ATOM | 971 | CE | MET | A | 1045 | −9.277 | 3.697 | 15.312 | 1.00 | 33.78 | A | C |
| ATOM | 972 | C | MET | A | 1045 | −6.212 | 0.453 | 16.301 | 1.00 | 28.40 | A | C |
| ATOM | 973 | O | MET | A | 1045 | −5.977 | 0.745 | 17.473 | 1.00 | 28.11 | A | O |
| ATOM | 974 | N | LEU | A | 1046 | −7.160 | −0.422 | 15.960 | 1.00 | 29.67 | A | N |
| ATOM | 975 | CA | LEU | A | 1046 | −8.009 | −1.066 | 16.990 | 1.00 | 30.76 | A | C |
| ATOM | 976 | CB | LEU | A | 1046 | −9.209 | −1.781 | 16.363 | 1.00 | 31.19 | A | C |
| ATOM | 977 | CG | LEU | A | 1046 | −10.287 | −0.957 | 15.664 | 1.00 | 30.30 | A | C |
| ATOM | 978 | CD1 | LEU | A | 1046 | −11.304 | −1.940 | 15.086 | 1.00 | 30.38 | A | C |
| ATOM | 979 | CD2 | LEU | A | 1046 | −10.987 | 0.013 | 16.605 | 1.00 | 31.16 | A | C |
| ATOM | 980 | C | LEU | A | 1046 | −7.244 | −2.051 | 17.859 | 1.00 | 32.40 | A | C |
| ATOM | 981 | O | LEU | A | 1046 | −7.545 | −2.193 | 19.064 | 1.00 | 30.71 | A | O |
| ATOM | 982 | N | GLY | A | 1047 | −6.280 | −2.729 | 17.221 | 1.00 | 34.38 | A | N |
| ATOM | 983 | CA | GLY | A | 1047 | −5.392 | −3.714 | 17.836 | 1.00 | 38.71 | A | C |
| ATOM | 984 | C | GLY | A | 1047 | −4.312 | −3.032 | 18.650 | 1.00 | 41.51 | A | C |
| ATOM | 985 | O | GLY | A | 1047 | −3.600 | −3.684 | 19.399 | 1.00 | 42.12 | A | O |
| ATOM | 986 | N | GLN | A | 1048 | −4.234 | −1.713 | 18.494 | 1.00 | 43.65 | A | N |
| ATOM | 987 | CA | GLN | A | 1048 | −3.259 | −0.785 | 19.123 | 1.00 | 47.00 | A | C |
| ATOM | 988 | CB | GLN | A | 1048 | −3.500 | −0.616 | 20.645 | 1.00 | 47.75 | A | C |
| ATOM | 989 | CG | GLN | A | 1048 | −4.961 | −0.159 | 20.971 | 1.00 | 49.61 | A | C |
| ATOM | 990 | CD | GLN | A | 1048 | −5.162 | 0.237 | 22.438 | 1.00 | 51.52 | A | C |
| ATOM | 991 | OE1 | GLN | A | 1048 | −5.321 | 1.426 | 22.760 | 1.00 | 52.35 | A | O |
| ATOM | 992 | NE2 | GLN | A | 1048 | −5.137 | −0.750 | 23.333 | 1.00 | 51.14 | A | N |
| ATOM | 993 | C | GLN | A | 1048 | −1.793 | −1.038 | 18.730 | 1.00 | 48.43 | A | C |
| ATOM | 994 | O | GLN | A | 1048 | −1.350 | −0.504 | 17.691 | 1.00 | 49.24 | A | O |
| ATOM | 995 | OXT | GLN | A | 1048 | −1.124 | −1.774 | 19.486 | 1.00 | 49.94 | A | O |
| ATOM | 996 | C1 | C4C | B | 1 | −12.921 | 6.625 | −17.415 | 0.87 | 29.57 | B | C |
| ATOM | 997 | N3 | C4C | B | 1 | −13.756 | 5.515 | −17.848 | 0.87 | 27.04 | B | N |
| ATOM | 998 | C2 | C4C | B | 1 | −14.629 | 5.668 | −19.001 | 0.87 | 31.67 | B | C |
| ATOM | 999 | C3 | C4C | B | 1 | −13.717 | 4.252 | −17.127 | 0.87 | 27.88 | B | C |
| ATOM | 1000 | C4 | C4C | B | 1 | −12.958 | 3.704 | −17.781 | 0.87 | 22.83 | B | C |
| ATOM | 1001 | N1 | C4C | B | 1 | −11.792 | 3.191 | −17.996 | 0.87 | 13.84 | B | N |
| ATOM | 1002 | C12 | C4C | B | 1 | −11.212 | 2.369 | −17.022 | 0.87 | 22.12 | B | C |
| ATOM | 1003 | C13 | C4C | B | 1 | −9.917 | 2.623 | −16.585 | 0.87 | 28.93 | B | C |
| ATOM | 1004 | C14 | C4C | B | 1 | −9.349 | 1.804 | −15.619 | 0.87 | 31.14 | B | C |
| ATOM | 1005 | C15 | C4C | B | 1 | −10.094 | 0.747 | −15.111 | 0.87 | 29.91 | B | C |
| ATOM | 1006 | C16 | C4C | B | 1 | −11.385 | 0.532 | −15.578 | 0.87 | 31.54 | B | C |
| ATOM | 1007 | N2 | C4C | B | 1 | −11.915 | 1.334 | −16.511 | 0.87 | 29.58 | B | N |
| ATOM | 1008 | C5 | C4C | B | 1 | −11.061 | 3.898 | −18.740 | 0.87 | 25.70 | B | C |
| ATOM | 1009 | C6 | C4C | B | 1 | −9.762 | 3.372 | −19.218 | 0.87 | 28.05 | B | C |
| ATOM | 1010 | C11 | C4C | B | 1 | −9.326 | 2.074 | −18.847 | 0.87 | 30.37 | B | C |
| ATOM | 1011 | C10 | C4C | B | 1 | −8.101 | 1.493 | −19.257 | 0.87 | 32.64 | B | C |
| ATOM | 1012 | C7 | C4C | B | 1 | −8.943 | 4.142 | −20.041 | 0.87 | 31.21 | B | C |
| ATOM | 1013 | C8 | C4C | B | 1 | −7.606 | 3.521 | −20.372 | 0.87 | 32.67 | B | C |
| ATOM | 1014 | C9 | C4C | B | 1 | −7.323 | 2.298 | −20.074 | 0.87 | 32.83 | B | C |
| ATOM | 1015 | CL1 | C4C | B | 1 | −6.112 | 1.599 | −20.473 | 0.87 | 32.89 | B | C |
| ATOM | 1016 | OXT | ACT | C | 1 | 3.098 | 0.822 | −1.834 | 1.00 | 24.96 | C | O |
| ATOM | 1017 | C | ACT | C | 1 | 2.380 | −0.199 | −1.763 | 1.00 | 15.46 | C | C |
| ATOM | 1018 | O | ACT | C | 1 | 2.444 | −0.840 | −0.692 | 1.00 | 20.73 | C | O |
| ATOM | 1019 | CH3 | ACT | C | 1 | 1.496 | −0.629 | −2.895 | 1.00 | 22.43 | C | C |
| ATOM | 1020 | OXT | ACT | D | 1 | −2.105 | 15.839 | 1.379 | 1.00 | 41.00 | D | O |
| ATOM | 1021 | C | ACT | D | 1 | −1.701 | 16.585 | 2.297 | 1.00 | 39.78 | D | C |
| ATOM | 1022 | O | ACT | D | 1 | −0.892 | 16.075 | 3.102 | 1.00 | 40.59 | D | O |
| ATOM | 1023 | CH3 | ACT | D | 1 | −2.160 | 18.007 | 2.426 | 1.00 | 39.97 | D | C |
| ATOM | 1024 | ZN | ZN | E | 1 | −20.934 | 15.131 | −9.921 | 1.00 | 24.21 | E | Z |
| ATOM | 1025 | O | HOH | S | 1 | −14.637 | 13.904 | −2.022 | 1.00 | 23.76 | S | O |
| ATOM | 1026 | O | HOH | S | 2 | 3.065 | 1.659 | 5.947 | 1.00 | 15.12 | S | O |
| ATOM | 1027 | O | HOH | S | 3 | −19.483 | 13.452 | −6.104 | 1.00 | 18.58 | S | O |
| ATOM | 1028 | O | HOH | S | 4 | −3.635 | 5.489 | −4.282 | 1.00 | 23.70 | S | O |

TABLE 2-continued (atomic coordinates disclosed as SEQ ID NO: 7)

| ATOM | 1029 | O | HOH | S | 5 | 2.216 | 23.103 | −28.277 | 1.00 | 23.68 | S | O |
|---|---|---|---|---|---|---|---|---|---|---|---|---|
| ATOM | 1030 | O | HOH | S | 6 | −6.456 | 3.968 | −16.650 | 1.00 | 26.82 | S | O |
| ATOM | 1031 | O | HOH | S | 7 | −1.566 | 24.600 | −31.314 | 1.00 | 28.75 | S | O |
| ATOM | 1032 | O | HOH | S | 8 | −17.047 | 5.220 | −17.920 | 1.00 | 41.29 | S | O |
| ATOM | 1033 | O | HOH | S | 9 | −3.711 | 9.474 | −19.813 | 1.00 | 25.74 | S | O |
| ATOM | 1034 | O | HOH | S | 10 | −17.137 | 22.350 | −11.498 | 1.00 | 25.94 | S | O |
| ATOM | 1035 | O | HOH | S | 11 | −2.800 | −0.164 | 5.726 | 1.00 | 27.14 | S | O |
| ATOM | 1036 | O | HOH | S | 12 | 4.655 | 1.737 | 1.848 | 1.00 | 31.78 | S | O |
| ATOM | 1037 | O | HOH | S | 13 | −16.690 | 26.308 | −7.142 | 1.00 | 25.63 | S | O |
| ATOM | 1038 | O | HOH | S | 14 | 3.365 | 2.049 | 14.881 | 1.00 | 26.19 | S | O |
| ATOM | 1039 | O | HOH | S | 15 | −0.475 | 1.267 | 5.878 | 1.00 | 29.54 | S | O |
| ATOM | 1040 | O | HOH | S | 16 | 2.680 | 13.257 | −6.744 | 1.00 | 33.15 | S | O |
| ATOM | 1041 | O | HOH | S | 17 | −17.068 | 24.904 | −25.464 | 1.00 | 35.95 | S | O |
| ATOM | 1042 | O | HOH | S | 18 | −17.365 | 15.275 | −13.310 | 1.00 | 27.45 | S | O |
| ATOM | 1043 | O | HOH | S | 19 | −24.539 | 11.199 | −11.327 | 1.00 | 39.70 | S | O |
| ATOM | 1044 | O | HOH | S | 20 | −12.627 | −4.363 | −0.998 | 1.00 | 43.64 | S | O |
| ATOM | 1045 | O | HOH | S | 21 | −5.411 | 26.199 | −29.400 | 1.00 | 29.44 | S | O |
| ATOM | 1046 | O | HOH | S | 22 | 1.220 | 15.059 | −22.171 | 1.00 | 43.08 | S | O |
| ATOM | 1047 | O | HOH | S | 23 | −26.065 | 11.201 | −8.946 | 1.00 | 45.30 | S | O |
| ATOM | 1048 | O | HOH | S | 24 | −13.989 | 15.422 | −29.612 | 1.00 | 33.49 | S | O |
| ATOM | 1049 | O | HOH | S | 25 | 1.445 | 22.688 | −25.687 | 1.00 | 43.34 | S | O |
| ATOM | 1050 | O | HOH | S | 26 | −15.911 | 20.189 | −29.185 | 1.00 | 36.67 | S | O |
| ATOM | 1051 | O | HOH | S | 27 | −13.010 | −1.423 | 0.046 | 1.00 | 43.49 | S | O |
| ATOM | 1052 | O | HOH | S | 28 | −11.034 | 25.825 | −23.409 | 1.00 | 42.59 | S | O |
| ATOM | 1053 | O | HOH | S | 29 | 5.044 | 4.105 | 8.250 | 1.00 | 25.80 | S | O |
| ATOM | 1054 | O | HOH | S | 30 | −3.887 | 23.620 | −32.090 | 1.00 | 42.66 | S | O |
| ATOM | 1055 | O | HOH | S | 31 | 1.169 | 19.787 | −28.877 | 1.00 | 49.89 | S | O |
| ATOM | 1056 | O | HOH | S | 32 | −17.913 | 23.589 | −7.952 | 1.00 | 35.64 | S | O |
| ATOM | 1057 | O | HOH | S | 33 | −12.554 | 20.728 | −2.217 | 1.00 | 25.33 | S | O |
| ATOM | 1058 | O | HOH | S | 34 | −4.766 | 22.430 | −2.849 | 1.00 | 52.27 | S | O |
| ATOM | 1059 | O | HOH | S | 35 | 0.081 | 3.261 | −1.549 | 1.00 | 49.37 | S | O |
| ATOM | 1060 | O | HOH | S | 36 | −8.349 | 17.554 | −37.679 | 1.00 | 43.88 | S | O |
| ATOM | 1061 | O | HOH | S | 37 | 2.597 | 3.985 | 16.574 | 1.00 | 45.47 | S | O |
| ATOM | 1062 | O | HOH | S | 38 | −0.584 | 11.566 | −27.584 | 1.00 | 42.90 | S | O |
| ATOM | 1063 | O | HOH | S | 39 | −22.448 | 29.278 | −23.528 | 1.00 | 39.72 | S | O |
| ATOM | 1064 | O | HOH | S | 40 | −2.704 | 3.687 | −11.205 | 1.00 | 49.15 | S | O |
| ATOM | 1065 | O | HOH | S | 41 | −10.046 | −4.591 | 0.122 | 1.00 | 45.11 | S | O |
| ATOM | 1066 | O | HOH | S | 42 | −16.778 | 25.077 | −13.021 | 1.00 | 44.09 | S | O |
| ATOM | 1067 | O | HOH | S | 43 | 6.883 | 10.793 | 1.758 | 1.00 | 52.19 | S | O |
| ATOM | 1068 | O | HOH | S | 44 | −20.453 | 9.773 | −0.791 | 1.00 | 37.32 | S | O |
| ATOM | 1069 | O | HOH | S | 45 | −1.592 | −0.658 | −1.630 | 1.00 | 43.25 | S | O |
| ATOM | 1070 | O | HOH | S | 46 | −17.943 | 26.424 | −18.671 | 1.00 | 37.96 | S | O |
| ATOM | 1071 | O | HOH | S | 47 | −11.574 | 23.004 | −37.855 | 1.00 | 28.53 | S | O |
| ATOM | 1072 | O | HOH | S | 48 | −15.894 | 16.006 | 3.623 | 1.00 | 42.17 | S | O |
| ATOM | 1074 | O | HOH | S | 50 | 2.857 | 14.759 | 3.372 | 1.00 | 44.02 | S | O |
| ATOM | 1075 | O | HOH | S | 51 | −14.333 | 8.764 | 10.224 | 1.00 | 43.05 | S | O |
| ATOM | 1076 | O | HOH | S | 52 | −15.045 | 19.863 | −2.859 | 1.00 | 40.54 | S | O |
| ATOM | 1077 | O | HOH | S | 57 | 1.035 | −1.786 | 8.379 | 1.00 | 38.35 | S | O |
| ATOM | 1078 | O | HOH | S | 58 | 4.258 | 2.667 | −0.825 | 1.00 | 54.11 | S | O |
| ATOM | 1079 | O | HOH | S | 60 | 4.867 | −0.649 | −1.362 | 1.00 | 27.36 | S | O |
| ATOM | 1080 | O | HOH | S | 61 | −6.925 | 20.744 | −6.872 | 1.00 | 50.48 | S | O |
| ATOM | 1081 | O | HOH | S | 62 | −7.243 | 21.265 | −9.896 | 1.00 | 46.40 | S | O |
| ATOM | 1082 | O | HOH | S | 63 | −4.870 | 8.637 | −28.340 | 1.00 | 56.11 | S | O |
| ATOM | 1083 | O | HOH | S | 66 | −20.298 | 25.908 | −18.436 | 1.00 | 46.72 | S | O |
| ATOM | 1084 | O | HOH | S | 69 | −4.229 | 18.716 | −1.934 | 1.00 | 40.63 | S | O |
| ATOM | 1085 | O | HOH | S | 70 | −15.370 | 20.093 | 1.233 | 1.00 | 58.32 | S | O |
| ATOM | 1086 | O | HOH | S | 71 | −7.104 | 8.443 | −29.715 | 1.00 | 41.18 | S | O |
| ATOM | 1087 | O | HOH | S | 72 | −15.381 | 22.771 | 1.260 | 1.00 | 36.67 | S | O |
| ATOM | 1088 | O | HOH | S | 75 | −1.292 | 19.934 | −1.194 | 1.00 | 46.07 | S | O |
| ATOM | 1089 | O | HOH | S | 76 | −21.677 | 23.287 | −18.495 | 1.00 | 39.23 | S | O |
| ATOM | 1091 | O | HOH | S | 80 | −5.335 | 6.616 | −26.796 | 1.00 | 48.25 | S | O |
| END | | | | | | | | | | | | |

What is claimed is:

1. A method of inducing apoptosis in a cancer cell that expresses focal adhesion kinase (FAK) in a human comprising administering to the human identified as in need thereof a compound capable of inhibiting the binding interaction of focal adhesion kinase (FAK) with a second protein, wherein the compound is C4: N'-[(4-chlorophenyl)methyl]-N,N-dimethyl-N'-pyridin-2-yl-ethane-1,2-diamine.

2. The method of claim 1, wherein the second protein is VEGFR-3, RIP, or p53.

3. The method of claim 1, wherein the compound inhibits FAK binding at the focal adhesion targeting sequence (FAT) domain.

4. The method of claim 2, wherein the second protein is p53.

5. The method of claim 1, wherein the cancer is breast, colon, pancreatic, thyroid, lung, or melanoma.

6. A method of inhibiting a focal adhesion kinase (FAK) protein-protein binding interaction in a human identified as in need of cancer treatment, wherein the cancer cells express FAK, comprising administering to the human a compound identified as capable of inhibiting the FAK protein-protein binding interaction, wherein the compound is C4: N'-[(4-chlorophenyl)methyl]-N,N-dimethyl-N'-pyridin-2-yl-ethane-1,2-diamine.

7. A method of treating cancer in a human comprising administering to the human identified as in need thereof a compound capable of inhibiting the binding interaction of focal adhesion kinase (FAK) with a second protein that interacts with FAK, wherein the compound is C4: N'-[(4-chlorophenyl)methyl]-N,N-dimethyl-N'-pyridin-2-yl-ethane-1,2-diamine and wherein the cancer cells express FAK.

8. The method of claim 7, wherein the binding interaction with the second protein and FAK results in modulation of apoptosis or cellular proliferation of cancer cells.

9. The method of claim 7, wherein the cancer is breast, colon, pancreatic, thyroid, lung, or melanoma.

10. The method of claim 7, further comprising an additional therapeutic agent.

11. The method of claim 10, wherein the additional therapeutic agent is doxorubicin, cisplatin, taxol, 5-fluorouracil, gemcitabine or etoposid.

* * * * *

SEQUENCE LISTING

<160> NUMBER OF SEQ ID NOS: 7

<210> SEQ ID NO 1
<211> LENGTH: 12
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 1

Trp His Trp Gln Trp Thr Pro Trp Ser Ile Gln Pro
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp His Trp Arg Pro Trp Thr Pro Cys Lys Met Phe
 1               5                  10

<210> SEQ ID NO 3
<211> LENGTH: 7
<212> TYPE: PRT
<213> ORGANISM: Homo sapiens

<400> SEQUENCE: 3

Gln Met Ser Gly Ala Pro His
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Met Ser Ala Ala Pro Ala
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Met Pro Glu Ala Ala Pro
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Val Ser Gly Ala Pro Ala
 1               5

<210> SEQ ID NO 7
<211> LENGTH: 128
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 7

Asn Asp Lys Val Tyr Glu Asn Val Thr Gly Leu Val Lys Ala Val Ile
1               5                  10                  15

Glu Met Ser Ser Lys Ile Gln Pro Ala Pro Pro Glu Glu Tyr Val Pro
            20                  25                  30

Met Val Lys Glu Val Gly Leu Ala Leu Arg Thr Leu Leu Ala Thr Val
            35                  40                  45

Asp Glu Thr Ile Pro Leu Leu Pro Ala Ser Thr His Arg Glu Ile Glu
        50                  55                  60

Met Ala Gln Lys Leu Leu Asn Ser Asp Leu Gly Glu Leu Ile Asn Lys
65                  70                  75                  80

Met Lys Leu Ala Gln Gln Tyr Val Met Thr Ser Leu Gln Gln Glu Tyr
                85                  90                  95

Lys Lys Gln Met Leu Thr Ala Ala His Ala Leu Ala Val Asp Ala Lys
            100                 105                 110

Asn Leu Leu Asp Val Ile Asp Gln Ala Arg Leu Lys Met Leu Gly Gln
            115                 120                 125
```